United States Patent [19]
Johnson et al.

[11] Patent Number: 5,858,924
[45] Date of Patent: Jan. 12, 1999

[54] N-([1, 2, 4] TRIAZOLOAZINYL) BENZENESULFONAMIDE AND PYRIDINESULFONAMIDE COMPOUNDS AND THEIR USE AS HERBICIDES

[75] Inventors: Timothy C. Johnson; Robert J. Ehr, both of Indianapolis; Richard D. Johnston, Greenfield; William A. Kleschick, Indianapolis; Timothy P. Martin, Indianapolis; Mark A. Pobanz, Indianapolis; John C. Van Heertum, Indianapolis; Richard K. Mann, Franklin, all of Ind.

[73] Assignee: Dow AgroSciences LLC, Indianapolis, Ind.

[21] Appl. No.: 936,046

[22] Filed: Sep. 23, 1997

[51] Int. Cl.$^6$ .......................... A01N 43/90; C07D 487/04
[52] U.S. Cl. ............................. 504/241; 544/263
[58] Field of Search ............................ 544/263; 504/241

[56] References Cited

U.S. PATENT DOCUMENTS

| | | |
|---|---|---|
| 3,671,512 | 6/1972 | Mizzoni et al. . |
| 4,204,870 | 5/1980 | Chapman et al. . |
| 4,528,288 | 7/1985 | Wade . |
| 4,605,433 | 8/1986 | Pearson et al. . |
| 4,638,075 | 1/1987 | Kleschick et al. . |
| 4,666,501 | 5/1987 | Hay et al. . |
| 4,685,958 | 8/1987 | Pearson et al. . |
| 4,822,404 | 4/1989 | Kleschick . |
| 4,910,306 | 3/1990 | McKendry . |
| 5,163,995 | 11/1992 | Van Heertum et al. . |
| 5,459,138 | 10/1995 | Pirotte et al. . |
| 5,571,775 | 11/1996 | Van Heertum et al. . |

FOREIGN PATENT DOCUMENTS

| | | |
|---|---|---|
| 244948 | 12/1987 | European Pat. Off. . |
| 3539386 | 5/1987 | Germany . |

OTHER PUBLICATIONS

K. Saito, et al., *Chemical Abstracts*, 107, 77727 (1987) (Abstract of Yakugaku Zasshi, 106(11), 1008–1016 (1986)).
G. W. Miller et al., *J. Chemical Society*, 1963, 5642–5659.
G. W. Miller et al., *J. Chemical Society*, 1965, 3357–3368.
J. B. Medwid, et al., *Journal Medicinal Chemistry*, 33, 1230–1241 (1990).
K. T. Potts, et al., *Journal of Organic Chemistry*, 31, 265–273 (1966).
B. Vercek, et al., *Monatschefte fur Chemie*, 114, 789–798 (1983).

*Primary Examiner*—Patricia L. Morris
*Attorney, Agent, or Firm*—D. Wendell Osborne

[57] ABSTRACT

N-(Triazoloazinyl)arylsulfonamide compounds, such as 2,6-dimethoxy-N-(8-chloro-5-methoxy[1,2,4]-triazolo[1,5-c]pyrimidin-2-yl)benzenesulfonamide, 2-methoxy-4-(trifluoromethyl)-N-(5,8-dimethoxy[1,2,4]-triazolo[1,5-c]pyrimidin-2-yl)pyridine-3-sulfonamide, and 2-methoxy-6-methoxycarbonyl-N-(5,8-dimethoxy[1,2,4]triazolo[1,5-a]pyridin-2-yl)benzenesulfonamide were prepared from appropriately substituted 2-amino[1,2,4]triazolo-[1,5-c]pyrimidine and 2-amino[1,2,4]triazolo[1,5-a]-pyridine compounds and appropriately substituted benzene-sulfonyl chloride and pyridine-3-sulfonyl chloride compounds. The compounds were found to be useful as herbicides.

34 Claims, No Drawings

N-([1, 2, 4] TRIAZOLOAZINYL) BENZENESULFONAMIDE AND PYRIDINESULFONAMIDE COMPOUNDS AND THEIR USE AS HERBICIDES

CROSS-REFERENCE TO RELATED APPLICATIONS

This application claims the benefit of U.S. Provisional Application Number 60/026,556, filed Sep. 24, 1996.

BACKGROUND OF THE INVENTION

The present invention relates to substituted benzenesulfonamide and pyridinesulfonamide compounds, to herbicidal compositions containing the compounds, and to the utility of the compounds for the control of unwanted vegetation.

The control of unwanted vegetation by means of chemical agents, i.e., herbicides, is an important aspect of modern agriculture and land management. While many chemicals that are useful for the control of unwanted vegetation are known, new compounds that are more effective generally, are more effective for specific plant species, are less damaging to desirable vegetation, are safer to man or the environment, are less expensive to use, or have other advantageous attributes are desirable.

Many substituted benzenesulfonamide compounds are known and certain of them are known to possess herbicidal activity. For example, certain N-([1,2,4]triazolo[1,5-a]pyrimidin-2-yl)benzenesulfonamide compounds and their herbicidal utility were disclosed in U.S. Pat. No. 4,638,075 and certain N-([1,2,4]triazolo[1,3,5]-triazin-2-yl)benzenesulfonamide compounds were disclosed in U.S. Pat. No. 4,685,958. Certain N-phenyl arylsulfonamide compounds are also known and are known to possess herbicidal activity. For example, certain N-(substituted phenyl)[1,2,4]triazolo[1,5-c]pyrimidin-2-sulfonamide compounds were disclosed in U.S. Pat. No. 5,163,995 and certain N-(substituted phenyl)[1,2,4]triazolo[1,5-a]-pyridin-2-sulfonamide compounds were disclosed in U.S. Pat. No. 5,571,775, issued Nov. 5, 1996.

SUMMARY OF THE INVENTION

It has now been found that a class of novel N-(triazoloazinyl)arylsulfonamide compounds comprising N-([1,2,4]triazolo[1,5-c]pyrimidin-2-yl)benzenesulfonamide, N-([1,2,4]triazolo[1,5-c]pyrimidin-2-yl)pyridine-sulfonamide, N-([1,2,4]triazolo[1,5-a]pyridin-2-yl)-benzenesulfonamide, and N-([1,2,4]triazolo[1,5-a]pyridin-2-yl)pyridinesulfonamide compounds are potent herbicides for the control of unwanted vegetation by either pre-emergence or postemergence application. Many of the compounds have desirable selectivity to valuable crops and have favorable toxicological and environmental attributes.

The invention includes N-(triazoloazinyl)aryl-sulfonamide compounds of Formula I:

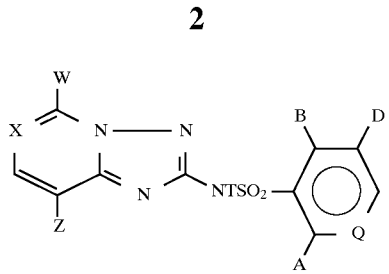

wherein

X represents N or C—Y;

W represents $O(C_1-C_3$ alkyl), Cl, Br, F, or H;

Y represents H, $OCH_3$, F, Cl, Br, I, or $CH_3$ optionally substituted with up to three fluorine atoms;

Z represents $O(C_1-C_3$ alkyl), H, F, Cl, Br, I, $S(C_1-C_3$ alkyl), or $CH_3$ optionally substituted with up to three fluorine atoms; with the proviso that at least one of W and Z represents $O(C_1-C_3$ alkyl);

Q represents C—H or N;

A represents F, Cl, Br, or I, or $CO_2(C_1-C_4$ alkyl) or represents $C_1-C_3$ alkyl, $O(C_1-C_4$ alkyl), $O(C_3-C_4$ alkenyl), $O(C_3-C_4$ alkynyl), or $S(C_1-C_3$ alkyl) each optionally substituted with one $O(C_1-C_3$ alkyl), $S(C_1-C_3$ alkyl), chloro, bromo, or cyano substituent or with up to the maximum possible number of fluorine atoms, or represents a 2-methyl-1,3-dioxolan-2-yl moiety, and, when Q represents N, H;

B represents H, F, Cl, Br, I, $NO_2$, CN, $CO_2(C_1-C_4$ alkyl), $NH(C_1-C_3$ alkyl), or $N(C_1-C_3$ alkyl)$_2$ or represents $O(C_1-C_4$ alkyl), $O(C_3-C_4$ alkenyl), $O(C_3-C_4$ alkynyl), $C_1-C_3$ alkyl, $S(C_1-C_3$ alkyl), $SO(C_1-C_3$ alkyl), $SO_2(C_1-C_3$ alkyl), $S(C_3-C_4$ alkenyl), $SO(C_3-C_4$ alkenyl), $SO_2(C_3-C_4$ alkenyl), $S(C_3-C_4$ alkynyl), $SO(C_3-C_4$ alkynyl), or $SO_2(C_3-C_4$ alkynyl) each optionally substituted with one $O(C_1-C_3$ alkyl), $S(C_1-C_3$ alkyl), chloro, bromo, or cyano substituent or with up to the maximum possible number of fluorine atoms; with the proviso that A and B do not simultaneously represent H;

D represents H, F, Cl, Br, I, $C_1-C_3$ alkyl, $OCH_3$, $OC_2H_5$, $CH_2F$, $CHF_2$, or $CF_3$; or B and D together represent a fragment of the formula O—$CH_2$—O, optionally substituted with one or two F or $CH_3$;

T represents H, $SO_2R$, C(O)R, C(O)OR, C(O)NR'$_2$, or $CH_2CH_2C(O)OR$;

R represents $C_1-C_4$ alkyl, $C_3-C_4$ alkenyl, or $C_3-C_4$ alkynyl each optionally possessing up to two chloro, bromo, $O(C_1-C_4)$alkyl, or phenyl substituents and up to the maximum possible number of fluoro substituents; and R' represents H, $C_1-C_4$ alkyl, $C_3-C_4$ alkenyl, or $C_3-C_4$ alkynyl;

and, when T represents H, the agriculturally acceptable salts thereof.

Compounds wherein X represents each of N and C—H and compounds wherein Q represents each of N and C—H are among the preferred compounds of the invention. Many of the preferred compounds of the invention possess a methoxy substituent in the 5-position (W) and a methoxy or halogen substituent in the 8-position (Z) of the triazoloazine ring. Some of the preferred compounds further possess an ortho methoxy substituent (A or B) in combination with a variety of substituents in the other ortho position (A or B) and hydrogen in the meta position; an ortho methoxy substituent (A) in combination with hydrogen or a meta methyl or chloro substituent (D) and no substituent in the other ortho position (B); or an ortho trifluoromethyl substituent (B) in combination with a variety of substituents in the other ortho position (A) and hydrogen in the meta position.

The invention further includes compositions containing herbicidal amounts of compounds of Formula I in combination with one or more agriculturally acceptable adjuvants or carriers and the use of the compounds of Formula I as herbicides. The use of suitable compounds of the invention to achieve either total vegetation control or the selective control of weeds in wheat, rice and oil-seed rape crops is generally preferred. Both grassy and broadleaf weeds can be controlled. Post-emergence application of the compounds to undesirable vegetation is generally preferred.

DETAILED DESCRIPTION OF THE INVENTION

The N-(triazoloazinyl)arylsulfonamide compounds of the invention can generally be described as substituted N-([1,2,4]triazolo[1,5-c]pyrimidin-2-yl)-benzenesulfonamide, N-([1,2,4]triazolo[1,5-c]pyrimidin-2-yl)pyridine-3-sulfonamide, N-([1,2,4]triazolo[1,5-a]-pyridin-2-yl) benzenesulfonamide, and N-([1,2,4]triazolo-[1,5-a]pyridin-2-yl)pyridine-3-sulfonamide compounds. They can be characterized as substituted benzenesulfonamide and pyridine-3-sulfonamide compounds possessing, on the amide nitrogen atom, a substituted [1,2,4]triazolo-[1,5-c] pyrimidin-2-yl or substituted [1,2,4]triazolo-[1,5-a]pyridin-2-yl moiety.

The herbicidal compounds of the invention are N-(triazoloazinyl)arylsulfonamide compounds of generic Formula I:

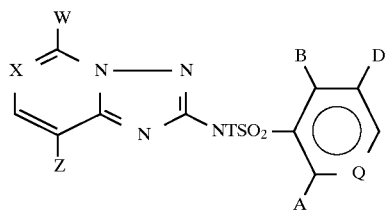

Such compounds in which X represents N contain a substituted N-([1,2,4]triazolo[1,5-c]pyrimidin-2-yl) moiety and those in which X represents C—Y contain a substituted N-([1,2,4]triazolo[1,5-a]pyridin-2-yl) moiety. Compounds in which Q represents N are pyridine-sulfonamide compounds and compounds in which Q represents C—H are benzenesulfonamide compounds. The compounds are further characterized by possessing a $C_1$–$C_3$ alkoxy substituent in one or both of the 5-and 8-positions (W and Z, respectively) of the triazoloazine ring and by possessing at least one ortho substituent (A) on the phenyl or pyridine ring.

The compounds of the invention include compounds of Formula I wherein X represents N or C—Y (wherein Y represents hydrogen, a halogen, methoxy, or methyl optionally substituted with up to three fluorine atoms). Compounds wherein X represents N are often preferred. Compounds wherein X represents C—H, however, are sometimes preferred. The compounds of the invention include compounds of Formula I wherein Q represents N or C—H. Each of these two options is sometimes preferred. Under many circumstances, compounds wherein X represents N and Q represents C—H are preferred but, under other circumstances, compounds wherein both X and Q represent N are preferred. On the other hand, under some circumstances, compounds wherein X represents C—Y and Q represents C—H are preferred.

The triazoloazine ring of the compounds of Formula I is at least mono substituted. The compounds of the invention include those wherein W represents methoxy, ethoxy, propoxy, 1-methylethoxy, cyclopropoxy, fluoro, chloro, bromo, or hydrogen and wherein Z represents methoxy, ethoxy, propoxy, 1-methylethoxy, cyclopropoxy, methylthio, ethylthio, 1-methylethylthio, cyclopropylthio, hydrogen, fluoro, chloro, bromo, iodo, or methyl optionally substituted with up to three fluorine atoms, with the proviso that at least one of W and Z represents one of the specified alkoxy moieties. Compounds wherein one of W and Z represents alkoxy, the other represents fluoro, chloro, bromo, methyl, methoxy, or ethoxy, and X represents N or C—H are often preferred. Such compounds wherein one or both of W and Z represents methoxy are often more preferred. Compounds of Formula I wherein W represents methoxy and Z represents methoxy, chloro, or bromo are often most preferred. Such compounds wherein X represents N are sometimes of special interest as are such compounds wherein X represents C—H and Z represents specifically methoxy.

The compounds of Formula I wherein Q represents C—H include those wherein A represents a halogen or ($C_1$–$C_4$ alkoxy)carbonyl or represents $C_1$–$C_3$ alkyl, $C_1$–$C_4$ alkoxy, $C_3$–$C_4$ alkenoxy, $C_3$–$C_4$ alkynoxy, or $C_1$–$C_3$ alkyl-thio each of which is optionally substituted with one $C_1$–$C_3$ alkoxy, $C_1$–$C_3$ alkylthio, chloro, bromo, or cyano substituent or with up to the maximum possible number of fluorine atoms. A may also represent a 2-methyl-1,3-dioxolan-2-yl moiety. When Q represents N, the compounds of Formula I also include those wherein A represents hydrogen. Methoxy, ethoxy, propoxy, 1-methylethoxy, methoxymethoxy, 2-fluoroethoxy, 2-chloroethoxy, 2,2-difluoroethoxy, 1-(fluoromethyl)-2-fluoroethoxy, trifluoromethoxy, chloro, and fluoro are often preferred. Methoxy, ethoxy, propoxy, or 1-methylethoxy, methoxymethoxy, methoxyethoxy, 2-fluoroethoxy, 2-chloroethoxy, 2,2-difluoroethoxy, and 1-(fluoromethyl)-2-fluoroethoxy are often more preferred. Methoxy is sometimes of special interest.

The compounds of Formula I further include those wherein B represents hydrogen, a halogen, nitro, cyano, ($C_1$–$C_4$ alkoxy)carbonyl, $C_1$–$C_3$ alkylamino, or di($C_1$–$C_3$ alkyl)amino or represents $C_1$–$C_3$ alkyl, $C_1$–$C_4$ alkoxy, $C_3$–$C_4$ alkenoxy, $C_3$–$C_4$ alkynoxy, $C_1$–$C_3$ alkylthio, $C_1$–$C_3$ alkanesulfinyl, $C_1$–$C_3$ alkanesulfonyl, $C_3$–$C_4$ alkenylthio, $C_3$–$C_4$ alkenesulfinyl, $C_3$–$C_4$ alkenesulfonyl, $C_3$–$C_4$ alkynylthio, $C_3$–$C_4$ alkynesulfinyl, or $C_3$–$C_4$ alkynesulfonyl each of which is optionally substituted with one $C_1$–$C_3$ alkoxy, $C_1$–$C_3$ alkylthio, chloro, bromo, or cyano substituent or with up to the maximum possible number of fluorine atoms. Such compounds wherein Q represents N and both A and B represent hydrogen are, however, excluded. Thus, whether Q represents N or C—H, at least one of A and B represents a substituent other than hydrogen. Hydrogen, methoxy, ethoxy, propoxy, 1-methylethoxy, methoxymethyl, methylthio, methyl, trifluoro-methyl, trifluoromethoxy, fluoro, chloro, and methoxy-carbonyl, are often preferred B substituents. Hydrogen, methoxy, ethoxy, propoxy, 1-methylethoxy, methoxymethyl, trifluoromethyl, fluoro, chloro, or methoxycarbonyl are typically more preferred when Q represents C—H and hydrogen, methoxy, ethoxy, propoxy, 1-methylethoxy, trifluoromethyl, and methoxycarbonyl are more preferred when Q represents N. Methoxy and trifluoromethyl are often, independently, B substituents of special interest.

The compounds of the invention still further include those wherein D represents hydrogen, a halogen, methyl, ethyl, 1-methylethyl, propyl, methoxy, ethoxy, fluoromethyl, difluoromethyl, or trifluoromethyl. They further include compounds wherein B and D together represent a methylenedioxy fragment optionally substituted with one or two fluorine or methyl groups. Compounds wherein D represents hydrogen, fluoro, bromo, chloro, or methyl are typically preferred. Compounds wherein D represents hydrogen, chloro, or methyl are often more preferred when Q represents C—H while those wherein D represents hydrogen or methyl more typically more preferred when Q represents N.

Compounds of Formula I wherein A represents methoxy, ethoxy, propoxy, 1-methylethoxy, methoxymethoxy, methoxyethoxy, 2-fluoroethoxy, 2-chloroethoxy, 2,2-difluoroethoxy, 1-(fluoromethyl)-2-fluoroethoxy, trifluoromethoxy, chloro, or fluoro; B represents hydrogen, methoxy, ethoxy, propoxy, 1-methylethoxy, methoxymethyl, methylthio, methyl, trifluoromethyl, trifluoromethoxy, fluoro, chloro, or methoxycarbonyl; and D represents hydrogen, fluoro, chloro, bromo, or methyl are often preferred. Such compounds wherein B represents methoxy and D represents hydrogen; wherein A represents methoxy and D represents hydrogen, methyl, or chloro; and wherein B represents trifluoromethyl and D represents hydrogen are often of special interest.

Compounds of Formula I wherein Q represents C—H and one or both of B and D represent hydrogen are often preferred. Compounds wherein Q represents C—H and A represents methoxy, ethoxy, propoxy, or 1-methylethoxy, methoxymethoxy, methoxyethoxy, 2-fluoroethoxy, 2-chloroethoxy, 2,2-difluoroethoxy, or 1-(fluoromethyl)-2fluroethoxy; B represents hydrogen, methoxy, ethoxy, propoxy, 1-methylethoxy, methoxymethyl, trifluoromethyl, fluoro, chloro, or methoxycarbonyl; and D represents hydrogen, chloro, or methyl are often more preferred. Such compounds wherein D represents hydrogen and either A and B each represent methoxy or A represents methoxy and B represents trifluoromethyl or methoxycarbonyl and are sometimes independently of interest. Compounds wherein Q represents C—H and A represents methoxy, ethoxy, propoxy, or 1-methylethoxy, B represents hydrogen; and D represents chloro or methyl are sometimes preferred.

Compounds of Formula I wherein Q represents N and A represents methoxy, ethoxy, propoxy, 1-methylethoxy, methoxymethoxy, methoxyethoxy, 2-fluoroethoxy, 2-chloroethoxy, 2,2-difluoroethoxy, or 1-(fluoromethyl)-2-fluoroethoxy; B represents hydrogen, methoxy, ethoxy, propoxy, 1-methylethoxy, trifluoromethyl, or methoxycarbonyl; and D represents hydrogen or methyl are typically preferred. Compounds wherein B represents trifluoromethyl and A represents methoxy, ethoxy, propoxy, 1-methylethoxy, methoxymethoxy, methoxyethoxy, 2-fluoroethoxy, 2-chloroethoxy, 2,2-difluoroethoxy, or 1-(fluoromethyl)-2-fluoroethoxy; and D represent hydrogen are typically more preferred.

The compounds of Formula I include those wherein T represents hydrogen, an alkylsulfonyl group ($SO_2R$), an acyl group (C(O)R), an alkoxycarbonyl group (C(O)OR), an aminocarbonyl group (C(O)NR'$_2$), or a 2-(alkoxycarbonyl) ethyl group ($CH_2CH_2C(O)OR$), wherein R represents $C_1$–$C_4$ alkyl, $C_3$–$C_4$ alkenyl, or $C_3$–$C_4$ alkynyl each optionally possessing up to two chloro, bromo, $C_1$–$C_4$ alkoxy, or phenyl substituents and up to the maximum possible number of fluoro substituents and R' represents H, $C_1$–$C_4$ alkyl, $C_3$–$C_4$ alkenyl, or $C_3$–$C_4$ alkynyl. Such compounds wherein T represents hydrogen are preferred. The invention further includes the agriculturally acceptable salts of compounds of the Formula I wherein T represents hydrogen.

Compounds of Formula I which possess each possible combination of preferred, more preferred, most preferred, desirable, and special interest substituents are, further, considered to be important embodiments of the invention.

The terms alkyl, alkenyl, and alkynyl (including when modified as in haloalkyl and alkoxy) as used herein include straight chain, branched chain, and cyclic groups. Thus, typical alkyl groups are methyl, ethyl, 1-methylethyl, propyl, 1,1-dimethylethyl, and cyclopropyl. Methyl and ethyl are often preferred. Alkyl groups are sometimes referred to herein as normal (n), iso (i), or secondary (s). Typical alkyl with up to the maximum possible number of fluoro substituents include trifluoromethyl, monofluoromethyl, 2,2,2-tri-fluoroethyl, 2,3-difluoropropyl, and the like; trifluoro-methyl is often preferred. The term halogen includes fluorine, chlorine, bromine, and iodine.

The term "agriculturally acceptable salts" is employed herein to denote compounds wherein the acidic sulfonamide proton of the compound of Formula I is replaced by a cation which itself is neither herbicidal to crop plants being treated nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula:

$R^6R^7R^8NH^+$ wherein $R^6$, $R^7$, and $R^8$ each, independently represents hydrogen or ($C_1$–$C_{12}$)alkyl, ($C_3$–$C_{12}$)cycloalkyl, or ($C_3$–$C_{12}$)alkenyl, each of which is optionally substituted by one or more hydroxy, ($C_1$–$C_8$)alkoxy, ($C_1$–$C_8$)alkylthio or phenyl groups; provided that $R^6$, $R^7$, and $R^8$ are sterically compatible. Additionally, any two of $R^6$, $R^7$, and $R^8$ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine.

The compounds of Table I are examples of the compounds of the invention. Some of the specifically preferred compounds of Formula I, which vary depending on the weed species to be controlled, the crop present (if any), and other factors, include the following compounds of Table 1: 1, 2, 10, 13, 14, 15, 18, 21, 23, 26, 27, 28, 32, 34, 36, 37, 38, 39, 41, 43, 46, 50, 52, 53, 54, 55, 60, 63, 65, 77, 80, 81, 92, 95, 96, 98, 105, 106, 109, 120, 122, 126, 139, 142, 167, 177, 184, 185, 187, 188, 190, 194, 195, 203, 208, 210, and 220. The following compounds are sometimes more preferred:2-methoxy-6-(trifluoromethyl)-N-(8-chloro-5-methoxy[1,2,4] triazolo-[1,5-c]pyrimidin2-yl)benzenesulfonamide (cpd. 34), 2,6-dimethoxy-N-(5,8-dimethoxy[1,2,4]triazolo[1,5-c]-pyrimidin-2-yl)benzenesulfonamide (cpd. 36), 2-methoxy-6-methoxycarbonyl-N-(5,8-dimethoxy[1,2,4]triazolo[1,5-a] -pyridin-2-yl) benzenesulfonamide (cpd. 98), 2-methoxy-5-methyl-N-(5,8-dimethoxy[1,2,4]triazolo[1,5-c]pyrimidin-2-yl) benzenesulfonamide (cpd. 105), 5-chloro-2-methoxy-N-(5,8-dimethoxy[1,2,4]triazolo[1,5-c]pyrimidin-2-yl)-benzenesulfonamide (cpd. 106), and2-methoxy-6-(trifluoromethyl)-N-(5,8-dimethoxy[1,2,4]triazolo[1,5-c]-pyrimidin-2-yl)pyridine-3-sulfonamide (cpd. 142), 2-(2- fluoroethoxy)-6-(trifluoromethyl)-N-(5,8-dimethoxy-[1,2,4]triazolo[1,5-c]pyrimidin-2-yl)benzenesulfonamide (cpd. 167), 2-(2-chloroethoxy)-6-(trifluoromethyl)-N-(5,8-dimethoxy[1,2,4]triazolo[1,5-c]pyrimidin-2-yl)-benzenesulfonamide (cpd. 203), 2-(2,2-difluoroethoxy)-6-(trifluoromethyl)-N-(5,8-dimethoxy[1,2,4]triazolo-[1,5-c]pyrimidin-2-yl)benzenesulfonamide (cpd. 190), and 2-(1-fluoromethyl-2-fluoroethoxy)-6-(trifluoromethyl)-N-(5,8-dimethoxy[1,2,4]triazolo[1,5-c]pyrimidin-2-yl)-benzenesulfonamide (cpd. 187).

TABLE 1

SULFONAMIDE COMPOUNDS

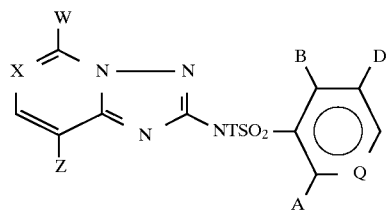

| Cpd. No. | X | W | Z | T | Q | A | B | D | Form | Melting Point, °C | Elem. Anal. Calc./Found % C | % H | % N |
|---|---|---|---|---|---|---|---|---|---|---|---|---|---|
| 1 | N | OCH$_3$ | F | H | C—H | Cl | H | H | white powder | 184–185 | 40.3 / 40.4 | 2.54 / 2.43 | 19.6 / 19.4 |
| 2 | N | OCH$_3$ | F | H | C—H | F | H | H | white powder | 226–228 | 42.2 / 42.4 | 2.66 / 2.43 | 20.5 / 20.2 |
| 3 | N | OCH$_3$ | F | H | C—H | CO$_2$CH$_3$ | H | H | white powder | 175–177 | 44.1 / 43.9 | 3.17 / 2.96 | 18.4 / 18.2 |
| 4 | N | OCH$_3$ | F | H | C—H | CF$_3$ | H | H | white powder | 185–187 | 39.9 / 40.2 | 2.32 / 2.19 | 17.9 / 17.7 |
| 5 | N | OCH$_3$ | F | H | C—H | OCH$_3$ | H | H | tan powder | 197–198 | 44.2 / 43.9 | 3.42 / 3.67 | 19.8 / 19.8 |
| 6 | N | OCH$_3$ | OCH$_3$ | H | C—H | Cl | H | H | white solid | 211–214 | 42.2 / 42.0 | 3.27 / 3.23 | 18.9 / 18.4 |
| 7 | N | OCH$_3$ | OCH$_3$ | H | C—H | F | H | H | white powder | 240–241 (d) | 44.2 / 43.7 | 3.42 / 3.30 | 19.8 / 19.2 |
| 8 | N | OCH$_3$ | OCH$_3$ | H | C—H | CO$_2$CH$_3$ | H | H | white powder | 189–191 | 45.8 / 46.0 | 3.84 / 3.75 | 17.8 / 17.0 |
| 9 | N | OCH$_3$ | OCH$_3$ | H | C—H | CF$_3$ | H | H | white powder | 189–191 | 39.9 / 43.3 | 3.09 / 3.22 | 17.9 / 16.5 |
| 10 | N | OCH$_3$ | OCH$_3$ | H | C—H | OCH$_3$ | H | H | tan powder | 231–233 | 46.0 / 46.2 | 4.14 / 4.00 | 19.2 / 19.0 |
| 11 | N | OCH$_3$ | OCH$_3$ | H | C—H | CH$_3$ | H | H | white powder | 188–191 | 48.1 / 49.0 | 4.33 / 4.28 | 20.1 / 19.3 |
| 12 | N | OCH$_3$ | OCH$_3$ | H | C—H | OCF$_3$ | H | H | white powder | 179–181 | 40.1 / 39.8 | 2.88 / 2.65 | 16.7 / 16.7 |
| 13 | N | OCH$_3$ | OCH$_3$ | H | C—H | OC$_2$H$_5$ | H | H | white powder | 224–226 | 47.5 / 47.1 | 4.52 / 4.67 | 18.5 / 18.5 |
| 14 | N | OCH$_3$ | OCH$_3$ | H | C—H | OC$_3$H$_7$(n) | H | H | tan powder | 222–224 | 48.9 / 48.8 | 4.87 / 4.93 | 17.8 / 17.6 |
| 15 | N | OCH$_3$ | OCH$_3$ | H | C—H | OC$_3$H$_7$(i) | H | H | tan powder | 172–174 | 48.9 / 48.9 | 4.87 / 5.09 | 17.8 / 17.6 |
| 16 | N | OCH$_3$ | OCH$_3$ | H | C—H | OCF$_2$CF$_2$H | H | H | white powder | 155–157 | 39.9 / 39.8 | 2.90 / 2.73 | 15.5 / 15.2 |
| 17 | N | OCH$_3$ | OCH$_3$ | H | C—H | SCH$_3$ | H | H | white powder | 213–215 | 44.1 / 43.8 | 3.96 / 4.17 | 18.4 / 18.1 |
| 18 | N | OCH$_3$ | I | H | C—H | OCH$_3$ | H | H | white powder | 219–220 (d) | 33.9 / 33.9 | 2.62 / 2.71 | 15.2 / 14.6 |
| 19 | N | OCH$_3$ | H | H | C—H | OCH$_3$ | H | H | white powder | 217–219 (d) | 37.7 / 37.8 | 2.92 / 2.91 | 16.9 / 17.0 |
| 20 | N | OCH$_3$ | H | H | C—H | Cl | Cl | H | tan powder | 225–226 | | | |
| 21 | N | OCH$_3$ | F | H | C—H | Cl | Cl | H | tan powder | 211–212 | 36.7 / 34.8 | 2.06 / 2.08 | 17.9 / 17.2 |
| 22 | N | OCH$_3$ | F | H | C—H | OCH$_3$ | CF$_3$ | H | tan powder | 220–223 | 39.9 / 40.3 | 2.63 / 2.95 | 16.6 / 17.0 |
| 23 | N | OCH$_3$ | OCH$_3$ | H | C—H | Cl | Cl | H | tan powder | 219–221 (d) | 38.6 / 38.6 | 2.74 / 2.81 | 17.3 / 17.4 |
| 24 | N | OCH$_3$ | OCH$_3$ | H | C—H | Cl | CH$_3$ | H | white powder | 221–223 (d) | 43.8 / 43.9 | 3.68 / 3.75 | 18.3 / 18.0 |
| 25 | N | OCH$_3$ | OCH$_3$ | H | C—H | F | F | H | white powder | 214–215 (d) | 42.1 / 42.2 | 2.99 / 3.08 | 18.9 / 18.6 |
| 26 | N | OCH$_3$ | OCH$_3$ | H | C—H | OCH$_3$ | Cl | H | white powder | 223–225 | 42.1 / 42.0 | 3.53 / 3.18 | 17.5 / 17.5 |
| 27 | N | OCH$_3$ | OCH$_3$ | H | C—H | OCH$_3$ | F | H | white | 239–240 | 43.9 | 3.68 | 18.3 |

TABLE 1-continued

SULFONAMIDE COMPOUNDS

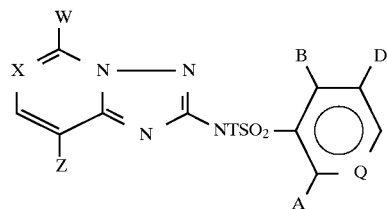

| Cpd. No. | X | W | Z | T | Q | A | B | D | Form | Melting Point, °C | Elem. Anal. Calc./Found % C | % H | % N |
|---|---|---|---|---|---|---|---|---|---|---|---|---|---|
| 28 | N | OCH₃ | OCH₃ | H | C—H | OCH₃ | CF₃ | H | white powder | 238–240 (d) | 43.4 41.6 41.5 | 4.05 3.26 3.20 | 16.4 16.2 16.3 |
| 29 | N | OCH₃ | OC₂H₅ | H | C—H | Cl | Cl | H | white powder | 217–218 | 40.2 40.1 | 3.13 3.13 | 16.7 16.8 |
| 30 | N | OCH₃ | I | H | C—H | Cl | Cl | H | tan powder | 210–212 (d) | 28.8 28.8 | 1.61 1.51 | 14.0 13.9 |
| 31 | N | OCH₃ | Br | H | C—H | Cl | Cl | H | white powder | 224–225 (d) | 31.8 32.0 | 1.78 1.74 | 15.5 15.3 |
| 32 | N | OCH₃ | CH₃ | H | C—H | Cl | Cl | H | white powder | 218–220 | 40.2 40.0 | 2.86 3.22 | 18.0 16.3 |
| 33 | N | OCH₃ | Cl | H | C—H | Cl | Cl | H | white powder | 214–216 (d) | 35.3 35.3 | 1.97 1.93 | 17.1 16.8 |
| 34 | N | OCH₃ | Cl | H | C—H | OCH₃ | CF₃ | H | white powder | 214–215 | 38.4 38.3 | 2.53 2.82 | 16.0 16.0 |
| 35 | N | OC₂H₅ | OCH₃ | H | C—H | OCH₃ | H | H | pink powder | 237–238 | 47.5 47.2 | 4.52 4.72 | 18.5 18.4 |
| 36 | N | OCH₃ | OCH₃ | H | C—H | OCH₃ | OCH₃ | H | tan solid | 239–241 | 45.6 45.7 | 4.33 4.19 | 17.7 16.6 |
| 37 | N | OCH₃ | Cl | H | C—H | OCH₃ | OCH₃ | H | yellow solid | 216–218 | 42.1 42.2 | 3.53 3.62 | 17.5 17.1 |
| 38 | N | OCH₃ | OCH₃ | H | C—H | OCH₃ | SCH₃ | H | tan solid | 232–234 | 43.8 43.0 | 4.16 4.11 | 17.0 16.4 |
| 39 | N | OCH₃ | Br | H | C—H | OCH₃ | CF₃ | H | white powder | 231–233 (d) | 34.9 34.6 | 14.5 14.3 | 2.30 2.17 |
| 40 | N | OCH₃ | OCH₃ | H | C—H | Cl | CF₃ | H | tan solid | 228–230 | 38.4 38.5 | 2.53 2.51 | 16.0 15.7 |
| 41 | N | OCH₃ | OCH₃ | H | C—H | OCH₃ | CH₃ | H | purple solid | 235–237 | 47.5 47.1 | 4.52 5.03 | 18.5 18.4 |
| 42 | N | OCH₃ | Cl | H | C—H | OCH₂CH₂F | CF₃ | H | white powder | 208–210 | 38.5 38.6 | 2.15 2.36 | 15.0 14.8 |
| 43 | N | OCH₃ | Cl | H | C—H | OC₃H₇(i) | CF₃ | H | tan powder | 210–213 (d) | 41.3 41.1 | 3.25 3.57 | 15.0 14.7 |
| 44 | N | OCH₃ | Cl | H | C—H | OC₂H₅ | CF₃ | H | white powder | 212–213 | 39.9 39.9 | 2.90 2.88 | 15.5 15.4 |
| 45 | N | OCH₃ | Cl | H | C—H | OC₃H₇(n) | CF₃ | H | yellow powder | 182–184 | 41.3 40.7 | 3.25 3.25 | 15.0 14.8 |
| 46 | N | OCH₃ | Cl | H | C—H | OCH₂CF₃ | CF₃ | H | tan powder | 202–203 | 35.6 35.7 | 1.99 1.94 | 13.9 13.1 |
| 47 | N | OCH₃ | OCH₃ | H | C—H | F | CF₃ | H | tan solid | 201–203 | 39.9 39.8 | 2.63 2.46 | 16.6 16.3 |
| 48 | N | OCH₃ | OCH₃ | H | C—H | SCH₃ | CF₃ | H | white solid | 127–129 | 40.1 40.1 | 3.14 3.11 | 15.6 15.2 |
| 49 | N | OCH₃ | OCH₃ | H | C—H | Cl | F | H | gray solid | 111–113 | 40.3 40.1 | 2.86 2.96 | 18.1 17.9 |
| 50 | N | OCH₃ | OCH₃ | H | C—H | OCH₃ | OC₂H₅ | H | pink solid | 233–234 (d) | 46.9 46.5 | 4.68 4.87 | 17.1 15.9 |
| 51 | N | OCH₃ | OCH₃ | H | C—H | OCH₃ | NO₂ | H | tan solid | 225–228 (d) | 41.0 38.8 | 3.33 3.60 | 20.5 19.1 |
| 52 | N | OCH₃ | OCH₃ | H | C—H | OC₂H₅ | CF₃ | H | white powder | 232–234 (d) | 43.0 42.9 | 3.60 3.51 | 15.7 15.7 |
| 53 | N | OCH₃ | OCH₃ | H | C—H | OCH₃ | CO₂CH₃ | H | white needles | 215–217 | 45.4 44.7 | 4.05 3.96 | 16.5 16.2 |
| 54 | N | OCH₃ | F | H | C—H | OCH₃ | OCH₃ | H | tan solid | 219–220 | 43.9 44.1 | 3.68 3.92 | 18.3 18.0 |
| 55 | N | OCH₃ | OCH₃ | H | C—H | OCH₃ | Br | H | tan solid | 226–228 | 37.9 37.8 | 3.18 3.39 | 15.8 15.8 |
| 56 | N | OCH₃ | Cl | H | C—H | OCH₃ | CO₂CH₃ | H | tan solid | 220–222 | 42.1 42.1 | 3.30 3.28 | 16.4 15.9 |
| 57 | N | OCH₃ | OCH₃ | H | C—H | OCH₃ | CO₂C₃H₇ | H | tan | 228–230 | 47.9 | 4.69 | 15.5 |

TABLE 1-continued

SULFONAMIDE COMPOUNDS

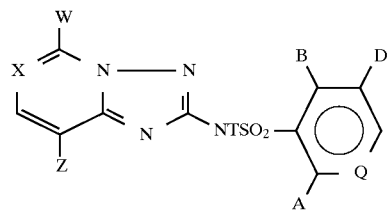

| Cpd. No. | X | W | Z | T | Q | A | B | D | Form | Melting Point, °C | %C | %H | %N |
|---|---|---|---|---|---|---|---|---|---|---|---|---|---|
| 58 | N | OCH₃ | OCH₃ | H | C—H | OCH₃ | CO₂C₂H₅ (i) | H | white solid | 215–217 | 47.9 46.7 46.2 | 4.89 4.38 3.70 | 15.8 16.0 14.4 |
| 59 | N | OCH₃ | OCH₃ | H | C—H | OC₂H₅ | OC₂H₅ | H | white solid | 211–213 (d) | 48.2 48.2 | 5.00 4.87 | 16.5 16.7 |
| 60 | N | OCH₃ | OCH₃ | H | C—H | OCH₃ | OC₃H₇(n) | H | white solid | 197–199 (d) | 48.1 48.6 | 5.22 4.94 | 16.5 16.1 |
| 61 | N | OCH₃ | OCH₃ | H | C—H | CF₃ | CF₃ | H | brown solid | 204–206 (d) | 38.2 38.2 | 2.35 2.03 | 14.9 14.7 |
| 62 | N | OCH₃ | OCH₃ | H | C—H | OC₂H₅ | CO₂CH₃ | H | white solid | 200–202 (d) | | | |
| 63 | N | OCH₃ | OC₂H₅ | H | C—H | OCH₃ | OCH₃ | H | white solid | 219–221 | 46.9 47.0 | 4.68 4.65 | 17.1 17.1 |
| 64 | N | OCH₃ | OCH₃ | H | C—H | Cl | CO₂CH₃ | H | tan powder | >270 | 42.1 42.2 | 3.30 3.20 | 16.4 16.2 |
| 65 | N | OCH₃ | I | H | C—H | OCH₃ | OCH₃ | H | tan powder | 230–232 (d) | 34.2 34.6 | 2.87 2.92 | 14.3 14.2 |
| 66 | N | OCH₃ | H | H | C—H | OCH₃ | OCH₃ | H | tan solid | 234–236 | 46.0 46.0 | 4.14 4.10 | 19.2 19.2 |
| 67 | N | OCH₃ | OC₂H₅ | H | C—H | OCH₃ | CF₃ | H | white solid | 222–224 | 43.0 42.4 | 3.60 3.60 | 15.7 15.1 |
| 68 | N | OCH₃ | CH₃ | H | C—H | OCH₃ | OCH₃ | H | tan solid | 224–227 | 47.5 47.0 | 4.52 4.87 | 18.5 16.4 |
| 69 | N | OCH₃ | OCH₃ | H | C—H | OCH₃ | SO₂CH₃ | H | white solid | 267–269 | 40.6 41.0 | 3.86 3.90 | 15.8 15.5 |
| 70 | N | OCH₃ | OCH₃ | H | C—H | OC₃H₇(i) | OC₃H₇(i) | H | off-wht solid | 193–195 (d) | 50.6 50.7 | 5.58 5.48 | 15.5 15.4 |
| 71 | N | OCH₃ | OCH₃ | H | C—H | OC₃H₇(n) | OC₃H₇(n) | H | peach solid | 158–159 (d) | 50.6 50.3 | 5.58 5.51 | 15.5 15.5 |
| 72 | N | OCH₃ | OCH₃ | H | C—H | OCH₃ | CH₂OCH₃ | H | tan solid | 211–213 | 46.9 46.8 | 4.68 4.68 | 17.1 16.9 |
| 73 | N | OCH₃ | OCH₃ | H | C—H | CO₂CH₃ | CH₃ | H | white solid | 188–190 | 47.2 47.2 | 4.21 3.95 | 17.2 17.1 |
| 74 | N | OCH₃ | OCH₃ | H | C—H | OCH₃ | OC₃H₇(i) | H | white solid | 204–205 | 48.2 47.7 | 5.00 5.01 | 16.5 16.3 |
| 75 | N | OCH₃ | I | H | C—H | OCH₃ | CF₃ | H | tan powder | 235–236 (d) | 31.8 31.6 | 2.10 2.06 | 13.2 12.4 |
| 76 | N | OCH₃ | I | H | C—H | OCH₃ | CO₂CH₃ | H | white solid | 215–217 (d) | | | |
| 77 | N | OCH₃ | Br | H | C—H | OCH₃ | OCH₃ | H | white solid | 229–231 (d) | 37.9 37.8 | 3.18 3.38 | 15.8 15.5 |
| 78 | N | OCH₃ | OCH₃ | H | C—H | OCH₂OCH₃ | OCH₂OCH₃ | H | tan solid | 148–150 (d) | 44.8 44.3 | 4.65 4.58 | 15.4 15.0 |
| 79 | N | OCH₃ | OCH₃ | H | C—H | F | CO₂CH₃ | H | white solid | 209–211 | 43.8 43.9 | 3.43 3.43 | 17.0 16.9 |
| 80 | N | OCH₃ | OCH₃ | H | C—H | OCH₃ | OCF₃ | H | white solid | 213–215 (d) | 40.1 39.9 | 3.14 3.54 | 15.6 15.6 |
| 81 | N | OCH₃ | OCH₃ | H | C—H | OCH₃ | OCH₂OCH₃ | H | white solid | 201–203 (d) | 45.2 45.3 | 4.50 4.49 | 16.5 16.0 |
| 82 | N | OCH₃ | Cl | H | C—H | OCH₃ | OCH₂OCH₃ | H | tan solid | 152–155 (d) | 41.9 41.7 | 3.75 3.80 | 16.3 15.7 |
| 83 | N | OCH₃ | Cl | COCH₃ | C—H | OCH₃ | CF₃ | H | white powder | 224–225 | 40.1 40.1 | 2.73 2.83 | 14.6 14.5 |
| 84 | N | OCH₃ | Cl | SO₂CH₃ | C—H | OCH₃ | CF₃ | H | white powder | 241–242 (d) | 34.9 35.4 | 2.54 2.74 | 13.6 12.9 |
| 85 | N | OCH₃ | Cl | CO₂C₂H₅ | C—H | OCH₃ | CF₃ | H | white powder | 230–232 (d) | 40.1 39.3 | 2.97 2.99 | 13.7 13.1 |
| 86 | C—CH₃ | H | OCH₃ | H | C—H | OCH₃ | OCH₃ | H | white solid | 274–276 (d) | 50.8 50.3 | 4.79 4.90 | 14.8 14.9 |
| 87 | C—H | H | OCH₃ | H | C—H | OCH₃ | OCH₃ | H | white | 279–281 | 49.5 | 4.43 | 15.4 |

TABLE 1-continued

SULFONAMIDE COMPOUNDS

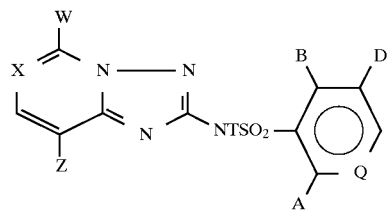

| Cpd. No. | X | W | Z | T | Q | A | B | D | Form | Melting Point, °C | %C | %H | %N |
|---|---|---|---|---|---|---|---|---|---|---|---|---|---|
| | | | | | | | | | solid | (d) | 49.4 | 4.42 | 15.3 |
| 88 | C—H | H | OCH₃ | H | C—H | OCH₃ | CF₃ | H | lt brn solid | 257–259 (d) | 44.8 44.5 | 3.26 3.27 | 13.9 14.0 |
| 89 | C—CH₃ | H | OCH₃ | H | C—H | OCH₃ | CF₃ | H | off-wht solid | 261–263 (d) | 46.2 46.3 | 3.63 3.57 | 13.5 13.5 |
| 90 | C—H | H | OCH₃ | H | C—H | OCH₃ | CO₂CH₃ | H | white solid | 278–280 (d) | 49.0 48.8 | 4.11 4.06 | 14.3 14.4 |
| 91 | C—CH₃ | H | OCH₃ | H | C—H | OCH₃ | CO₂CH₃ | H | white solid | 255–257 (d) | 50.2 50.2 | 4.46 4.37 | 13.8 13.6 |
| 92 | C—H | OCH₃ | OCH₃ | H | C—H | OCH₃ | OCH₃ | H | purple solid | 233–235 (d) | 48.7 48.8 | 4.60 4.57 | 14.2 14.2 |
| 93 | C—H | OCH₃ | Cl | H | C—H | OCH₃ | OCH₃ | H | off-wht solid | 248–249 (d) | 45.2 44.3 | 3.79 3.58 | 14.1 13.7 |
| 94 | C—H | Cl | OCH₃ | H | C—H | OCH₃ | OCH₃ | H | white solid | 252–254 (d) | 45.2 45.2 | 3.79 3.80 | 14.1 14.0 |
| 95 | C—H | Cl | OCH₃ | H | C—H | OCH₃ | CF₃ | H | white solid | 263–264 (d) | 41.3 41.1 | 2.77 2.81 | 12.8 13.0 |
| 96 | C—H | OCH₃ | OCH₃ | H | C—H | OCH₃ | CF₃ | H | off-wht solid | 256–258 (d) | 44.5 44.5 | 3.50 3.45 | 13.0 12.9 |
| 97 | C—H | Cl | OCH₃ | H | C—H | OCH₃ | CO₂CH₃ | H | white solid | 218–219 (d) | 45.0 44.9 | 3.54 3.39 | 13.1 12.8 |
| 98 | C—H | OCH₃ | OCH₃ | H | C—H | OCH₃ | CO₂CH₃ | H | off-wht solid | 274–276 (d) | 48.3 48.6 | 4.30 4.26 | 13.3 13.1 |
| 99 | C—H | OCH₃ | OCH₃ | H | C—H | Cl | Cl | H | lt tan powder | 235–236 (d) | | | |
| 100 | C—H | OCH₃ | Cl | H | C—H | Cl | Cl | H | gray solid | >270 | 38.3 3737 | 2.23 1.99 | 13.4 14.6 |
| 101 | C—H | OCH₃ | H | H | C—H | Cl | Cl | H | purple solid | 242–244 (d) | 41.8 41.5 | 2.70 2.58 | 15.0 14.7 |
| 102 | C—H | H | OCH₃ | H | C—H | Cl | Cl | H | white solid | 278–280 (d) | 41.8 41.9 | 2.70 2.77 | 15.0 15.2 |
| 103 | C—CF₃ | H | OCH₃ | H | C—H | Cl | Cl | H | white solid | 247–248 (d) | 38.1 38.2 | 2.06 2.05 | 7.27 7.30 |
| 104 | C—Cl | H | OCH₃ | H | C—H | Cl | Cl | H | off-wht solid | 266–269 (d) | | | |
| 105 | N | OCH₃ | OCH₃ | H | C—H | OCH₃ | H | CH₃ | white powder | 217–219 (d) | 47.5 47.7 | 4.52 4.61 | 18.5 18.3 |
| 106 | N | OCH₃ | OCH₃ | H | C—H | OCH₃ | H | Cl | white powder | 205–207 | 42.1 42.2 | 3.53 3.75 | 17.5 17.2 |
| 107 | N | OCH₃ | OCH₃ | H | C—H | OCH₃ | H | OCH₃ | white powder | 233–235 (d) | 45.6 45.7 | 4.33 4.57 | 17.7 17.5 |
| 108 | N | OCH₃ | OCH₃ | H | C—H | OCH₃ | H | Br | white powder | 225–227 | 37.9 38.1 | 3.18 3.38 | 15.8 15.3 |
| 109 | N | OCH₃ | OCH₃ | H | C—H | Cl | H | Cl | white powder | 219–221 (d) | 38.6 38.6 | 2.74 2.85 | 17.3 16.6 |
| 110 | N | OCH₃ | OCH₃ | H | C—H | CH₃ | H | F | white powder | 184–186 (d) | 45.8 46.0 | 3.84 3.92 | 19.1 18.8 |
| 111 | N | OCH₃ | OCH₃ | H | C—H | OC₂H₅ | H | CH₃ | white powder | 197–200 | 48.9 50.8 | 4.87 5.65 | 17.8 17.6 |
| 112 | N | OCH₃ | OCH₃ | H | C—H | OCH₃ | H | C₂H₅ | white powder | 200–202 | 48.9 48.7 | 4.87 4.81 | 17.8 17.9 |
| 113 | N | OCH₃ | OCH₃ | H | C—H | OCH₃ | H | C₃H₇ (i) | white powder | 199–201 | 50.1 50.0 | 5.20 5.69 | 17.2 17.4 |
| 114 | N | OCH₃ | OCH₃ | H | C—H | OC₂H₅ | H | F | white powder | 217–219 | 45.3 43.7 | 4.06 4.08 | 17.6 16.8 |
| 115 | N | OCH₃ | OCH₃ | H | C—H | OCH₃ | H | CF₃ | white powder | 215–216 | 41.6 41.3 | 3.26 3.51 | 16.2 16.0 |
| 116 | N | OCH₃ | OC₂H₅ | H | C—H | OCH₃ | H | CH₃ | white powder | 211–213 | 48.9 49.1 | 4.87 4.91 | 17.8 18.0 |
| 117 | N | OCH₃ | Br | H | C—H | OCH₃ | H | Cl | pink | 204–205 | 34.8 | 2.47 | 15.6 |

TABLE 1-continued

SULFONAMIDE COMPOUNDS

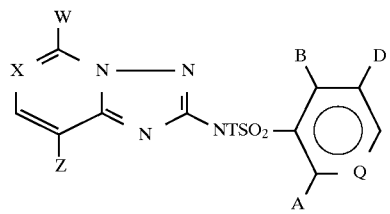

| Cpd. No. | X | W | Z | T | Q | A | B | D | Form | Melting Point, °C | Elem. Anal. Calc./Found % C | % H | % N |
|---|---|---|---|---|---|---|---|---|---|---|---|---|---|
| 118 | N | OCH₃ | Br | H | C—H | OCH₃ | H | F | solid white powder | 221–223 | 36.4 36.1 36.1 | 2.95 2.57 2.64 | 15.6 16.2 16.0 |
| 119 | N | OCH₃ | I | H | C—H | OCH₃ | H | Cl | pink powder | 223–225 | 31.5 32.8 | 2.24 2.45 | 14.1 13.1 |
| 120 | N | OCH₃ | Cl | H | C—H | OCH₃ | H | Cl | white powder | 203–205 | 3836 3838 | 2.74 2.85 | 17.3 16.7 |
| 121 | N | OCH₃ | Cl | H | C—H | OCH₃ | H | F | white powder | 217–219 | 40.3 39.7 | 2.86 2.54 | 18.1 17.9 |
| 122 | N | OCH₃ | Cl | H | C—H | OCH₃ | H | CH₃ | white powder | 195–196 | 43.8 43.0 | 3.68 4.61 | 18.3 18.0 |
| 123 | N | OCH₃ | OCH₃ | H | C—H | OCH₃ | H | F | pink powder | 205–207 (d) | 43.9 42.8 | 3.68 3.57 | 18.3 16.8 |
| 124 | N | OCH₃ | OCH₃ | H | C—H | SCH₃ | H | CH₃ | tan powder | 217–219 | 45.6 46.0 | 4.33 5.12 | 17.7 17.8 |
| 125 | N | OCH₃ | OCH₃ | H | C—H | SCH₃ | H | Cl | white powder | 216–218 | 40.4 40.5 | 3.39 3.39 | 16.8 16.7 |
| 126 | N | OCH₃ | OCH₃ | H | C—H | CH₃ | H | CH₃ | white powder | 218–220 | 49.6 49.6 | 4.72 4.65 | 19.3 19.0 |
| 127 | N | OCH₃ | OCH₃ | H | C—H | OCH₂CH₂F | H | CH₃ | white powder | 117–119 (d) | 46.7 44.9 | 4.41 4.72 | 17.0 15.9 |
| 128 | N | OCH₃ | OCH₃ | H | C—H | OCH₂CF₃ | H | CH₃ | white powder | 202–204 | 43.0 43.0 | 3.60 3.86 | 15.7 15.5 |
| 129 | N | OCH₃ | OCH₃ | H | C—H | OC₂H₅ | H | Cl | white powder | 233–234 (d) | 43.5 43.5 | 3.90 4.51 | 16.9 16.5 |
| 130 | N | OCH₃ | OCH₃ | H | C—H | CO₂CH₃ | H | F | white solid | 196–198 | 43.8 43.9 | 3.43 3.54 | 17.0 17.0 |
| 131 | N | OCH₃ | I | H | C—H | OCH₃ | H | CH₃ | white solid | 230–232 (d) | 35.4 35.6 | 2.97 3.06 | 14.7 14.3 |
| 132 | N | OCH₃ | OCH₃ | H | C—H | CO₂CH₃ | H | CH₃ | tan solid | 193–195 (d) | 47.2 47.2 | 4.21 4.35 | 17.2 17.2 |
| 133 | N | OCH₃ | OCH₃ | H | C—H | OCH₂OCH₃ | H | CH₃ | tan solid | 163–165 (d) | 47.0 46.7 | 4.68 4.51 | 17.1 16.2 |
| 134 | N | OCH₃ | OCH₃ | H | C—H | OCH₃ | OCH₃ | Cl | white powder | 233–234 | 41.9 41.7 | 3.75 3.91 | 16.3 16.1 |
| 135 | N | OCH₃ | OCH₃ | H | C—H | Cl | CH₃ | Cl | white powder | 180–182 | 40.2 38.3 | 3.13 3.50 | 16.7 15.4 |
| 136 | N | OCH₃ | OCH₃ | H | C—H | OCH₃ | Cl | Cl | white powder | 227–228 | 38.7 38.6 | 3.02 3.25 | 16.1 15.9 |
| 137 | N | OCH₃ | OCH₃ | H | C—H | OCH₃ | CO₂CH₃ | Cl | white powder | 236–238 (d) | 42.0 42.0 | 3.52 3.52 | 15.3 15.0 |
| 138 | N | OCH₃ | OCH₃ | H | C—H | OCH₃ | OCH₃ | CH₃ | tan solid | 228–230 (d) | 46.9 47.0 | 4.68 4.60 | 17.1 17.1 |
| 139 | N | OCH₃ | OCH₃ | H | C—H | OCH₃ | F | CH₃ | tan solid | 205–208 (d) | 45.3 45.4 | 4.06 4.07 | 17.6 17.3 |
| 140 | N | OCH₃ | Cl | H | C—H | OCH₃ | OCH₃ | CH₃ | tan solid | 223–225 (d) | 43.5 43.3 | 3.90 3.90 | 16.9 16.6 |
| 141 | N | OCH₃ | OCH₃ | H | N | OCH₃ | H | H | tan powder | 242–244 (d) | 42.6 42.6 | 3.85 3.82 | 22.9 21.6 |
| 142 | N | OCH₃ | OCH₃ | H | N | OCH₃ | CF₃ | H | white powder | 214–216 | 38.7 38.5 | 3.02 3.15 | 19.4 19.4 |
| 143 | C—H | H | OCH₃ | H | C—H | OCH₃ | H | H | lt tan powder | 249–250 (d) | 50.3 50.4 | 4.22 4.10 | 16.8 16.8 |
| 144 | C—H | OCH₃ | H | H | C—H | OCH₃ | H | H | off-wht powder | 249–250 (d) | 50.3 50.4 | 4.22 3.93 | 16.8 16.8 |
| 145 | C—H | OC₂H₅ | H | H | C—H | OCH₃ | H | H | lt tan powder | 250–251 (d) | 51.7 51.8 | 4.63 4.65 | 16.1 16.2 |
| 146 | N | OCH₃ | Cl | H | C—H | OCH₃ | F | CH₃ | tan solid | 196–198 | 41.9 41.6 | 3.26 3.39 | 17.4 17.6 |
| 147 | N | OCH₃ | OCH₃ | H | C—H | F | OCH₃ | CH₃ | lt red | 165–168 | 45.3 | 4.06 | 17.6 |

TABLE 1-continued

SULFONAMIDE COMPOUNDS

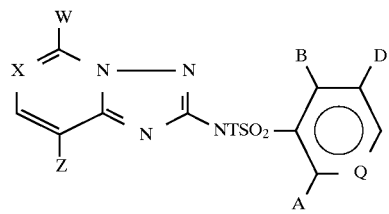

| Cpd. No. | X | W | Z | T | Q | A | B | D | Form | Melting Point, °C | %C | %H | %N |
|---|---|---|---|---|---|---|---|---|---|---|---|---|---|
| 148 | N | OCH₃ | Cl | H | C—H | F | OCH₃ | CH₃ | tan solid | 176–178 | 45.3 41.9 41.5 | 4.06 3.26 3.27 | 17.6 17.4 17.3 |
| 149 | N | OCH₃ | OCH₃ | H | C—H | CF₃ | OCH₃ | CH₃ | tan solid | 183–185 | | | |
| 150 | N | OCH₃ | OCH₃ | H | C—H | OCH₃ | OCH₂CH₂—OCH₃ | H | white solid | 173–175 | 46.5 46.5 | 4.82 4.87 | 15.9 15.9 |
| 151 | N | OCH₃ | Cl | H | C—H | OCH₃ | CH₂OC₃H₇(i) | H | white solid | 224–226 | 46.2 45.9 | 4.56 4.46 | 15.9 15.5 |
| 152 | N | OCH₃ | SCH₃ | H | C—H | Cl | Cl | H | tan solid | 207–209 | 37.2 37.2 | 2.64 2.56 | 16.7 16.5 |
| 153 | N | OCH₃ | SCH₃ | H | C—H | OCH₃ | CF₃ | H | tan solid | 215–217 | 40.1 40.0 | 3.14 3.18 | 15.5 15.4 |
| 154 | N | OCH₃ | Cl | H | C—H | OCF₃ | H | CH₃ | tan solid | 182–184 | 38.4 38.1 | 2.53 2.39 | 15.0 15.6 |
| 155 | N | OCH₃ | OCH₃ | H | N | OCH₃ | Cl | H | white powder | 227–228 | 39.0 38.7 | 3.27 3.14 | 21.0 20.9 |
| 156 | N | OCH₃ | OCH₃ | H | N | OCH₃ | OCH₃ | H | tan powder | 223–225 | 42.4 41.8 | 4.07 3.96 | 21.2 20.5 |
| 157 | C—H | OC₂H₅ | OCH₃ | H | C—H | OCH₃ | OCH₃ | H | white solid | 241–243 (d) | 50.0 49.9 | 4.94 4.80 | 13.7 13.6 |
| 158 | C—H | Cl | OCH₃ | H | C—H | OCH₃ | Cl | H | white solid | 264–266 (d) | 41.7 41.7 | 3.00 2.97 | 13.9 13.9 |
| 159 | C—H | OCH₃ | OCH₃ | H | C—H | OCH₃ | Cl | H | white solid | 246–248 (d) | 45.2 45.3 | 3.79 3.69 | 14.1 14.0 |
| 160 | C—H | Cl | OCH₃ | H | C—H | OCH₃ | H | CH₃ | white solid | 245–247 (d) | 47.1 47.0 | 3.95 3.93 | 14.6 14.4 |
| 161 | C—H | OCH₃ | OCH₃ | H | C—H | OCH₃ | H | CH₃ | white solid | 258–260 (d) | 50.8 49.9 | 4.79 4.48 | 14.8 14.2 |
| 162 | C—H | Cl | OCH₃ | H | C—H | OCH₃ | H | Cl | white solid | 207–211 (d) | 41.7 41.8 | 3.00 2.90 | 13.9 13.7 |
| 163 | C—H | OCH₃ | OCH₃ | H | C—H | OCH₃ | H | Cl | white solid | 228–230 (d) | 45.2 45.2 | 3.79 3.84 | 14.1 14.0 |
| 164 | C—H | Br | OCH₃ | H | C—H | OCH₃ | OCH₃ | H | white solid | 243–245 (d) | 40.6 40.6 | 3.41 3.38 | 12.6 12.5 |
| 165 | C—Cl | H | OCH₃ | H | C—H | OCH₃ | OCH₃ | H | white solid | 268–270 (d) | 45.2 45.1 | 3.79 3.82 | 14.1 14.0 |
| 166 | N | OCH₃ | Cl | H | C—H | OCH₃ | Cl | Cl | tan powder | 217–219 | 35.6 35.5 | 2.30 2.44 | 16.0 15.6 |
| 167 | N | OCH₃ | OCH₃ | H | C—H | OCH₂CH₂F | CF₃ | H | white powder | 233–235 | 41.3 41.4 | 3.25 3.09 | 15.1 14.9 |
| 168 | N | OCH₃ | OCH₃ | H | C—H | OCH₂OCH₃ | CF₃ | H | white solid | 181–183 (d) | 41.5 41.6 | 3.48 3.42 | 15.1 15.0 |
| 169 | C—H | OCH₃ | OCH₃ | H | C—H | OCH₃ | CO₂CH₃ | H | white solid | 224–226 | 44.7 44.5 | 3.75 3.68 | 12.3 12.3 |
| 170 | N | OCH₃ | Cl | H | C—H | CO₂CH₃ | H | CH₃ | off-wht solid | 174–176 | 43.8 43.5 | 3.43 3.33 | 17.0 16.8 |
| 171 | N | OCH₃ | Cl | H | C—H | OCH₂OCH₃ | H | CH₃ | off-wht solid | 199–201 | 43.5 43.2 | 3.90 3.87 | 16.9 16.7 |
| 172 | C—H | OCH₃ | OCH₃ | H | N | OCH₃ | CF₃ | H | white solid | 226–227 | 41.6 41.7 | 3.26 3.24 | 16.2 15.9 |
| 173 | N | OCH₃ | Cl | H | N | OCH₃ | CF₃ | H | white powder | 238–240 | 35.7 35.9 | 2.07 2.22 | 19.2 19.2 |
| 174 | N | OCH₃ | OCH₃ | H | N | Cl | OCH₃ | H | white powder | 228–229 (d) | 39.0 38.8 | 3.26 3.13 | 21.0 21.7 |
| 175 | C—H | OCH₃ | OCH₃ | H | C—H | OCH₃ | CO₂C₂H₅ | H | tan solid | 204–206 (d) | 49.5 49.3 | 4.62 4.53 | 12.8 12.6 |
| 176 | C—H | OCH₃ | OCH₃ | H | C—H | OC₄H₉(i) | OC₄H₉(i) | H | tan solid | 145–147 | 52.6 52.5 | 6.10 6.08 | 14.6 14.4 |
| 177 | N | OCH₃ | OCH₃ | H | C—H | OC₃H₇(n) | CF₃ | H | white | 202–204 | 44.3 | 3.93 | 15.2 |

TABLE 1-continued

SULFONAMIDE COMPOUNDS

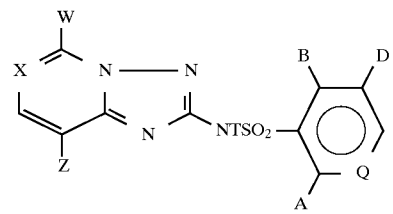

| Cpd. No. | X | W | Z | T | Q | A | B | D | Form | Melting Point, °C | %C | %H | %N |
|---|---|---|---|---|---|---|---|---|---|---|---|---|---|
| 178 | N | OCH₃ | Cl | H | C—H | OCH₃ | Cl | H | tan powder | >250 | 44.1 | 3.81 | 15.0 |
| 179 | N | OCH₃ | Cl | H | C—H | OC₂H₅ | H | CH₃ | tan powder | 214–216 | 45.3 / 45.0 | 4.05 / 3.86 | 17.6 / 17.3 |
| 180 | C—H | Br | OCH₃ | H | C—H | OC₂H₅ | OC₂H₅ | H | white solid | 244–246 | 43.3 / 43.3 | 4.06 / 3.90 | 11.9 / 11.9 |
| 181 | C—OCH₃ | H | OCH₃ | H | C—H | OCH₃ | OCH₃ | H | white powder | 274–276 | 48.7 / 48.7 | 4.60 / 4.50 | 14.2 / 14.1 |
| 182 | N | OCH₃ | Cl | H | C—H | OC₃H₇(i) | OC₃H₇(i) | H | tan solid | 174–176 | 47.4 / 47.5 | 4.86 / 4.90 | 15.4 / 15.3 |
| 183 | C—H | OCH₃ | OCH₃ | H | C—H | OC₂H₅ | OC₂H₅ | H | purple solid | 243–245 | 51.2 / 50.2 | 5.25 / 5.11 | 13.3 / 12.9 |
| 184 | N | OCH₃ | OCH₃ | H | C—H | OCH₂CH₂—OCH₃ | CF₃ | H | off-wht solid | 233–235 | 42.8 / 42.7 | 3.80 / 3.69 | 14.7 / 14.7 |
| 185 | N | OCH₃ | OCH₃ | H | C—H | OCH₂CF₃ | CF₃ | H | white solid | 211–213 | 38.3 / 38.3 | 2.61 / 2.59 | 14.0 / 13.9 |
| 186 | N | OCH₃ | OCH₃ | H | C—H | OCH₂CN | CF₃ | H | off-wht solid | 211–213 | 41.9 / 41.6 | 2.86 / 2.88 | 18.3 / 17.6 |
| 187 | N | OCH₃ | OCH₃ | H | C—H | OCH—(CH₂F)₂ | CF₃ | H | white solid | 229–231 | 40.1 / 41.0 | 3.24 / 3.12 | 14.1 / 14.0 |
| 188 | N | OCH₃ | OCH₃ | H | C—H | OCH₂—OC₂H₅ | CF₃ | H | white solid | 152–157 | 42.8 / 42.6 | 3.80 / 3.70 | 14.7 / 13.4 |
| 189 | N | OCH₃ | OCH₃ | H | C—H | OCH₂—CF₂CF₃ | CF₃ | H | white solid | 209–211 | 37.0 / 36.8 | 2.38 / 2.23 | 12.7 / 12.5 |
| 190 | N | OCH₃ | OCH₃ | H | C—H | OCH₂CHF₂ | CF₃ | H | tan solid | 223–224 | 39.8 / 39.5 | 2.92 / 2.74 | 14.5 / 14.3 |
| 191 | N | OCH₃ | OCH₃ | H | C—H | OCH₂CH₂F | H | F | white solid | 195–199 | | | |
| 192 | N | OCH₃ | OCH₃ | H | C—H | OCH₂OCH₃ | H | F | off-wht solid | 155–165 | | | |
| 193 | N | OCH₃ | OCH₃ | H | C—H | OCH₂OCH₃ | H | Cl | off-wht solid | 185–190 | 41.9 / 41.9 | 3.72 / 3.70 | 16.3 / 15.9 |
| 194 | N | OCH₃ | OCH₃ | H | C—H | OC₃H₇(i) | CF₃ | H | tan solid | 232–234 | 44.3 / 44.2 | 3.93 / 3.93 | 15.2 / 15.0 |
| 195 | N | OCH₃ | OCH₃ | H | C—H | OC₄H₉(n) | CF₃ | H | white solid | 185–187 | 45.5 / 45.2 | 4.24 / 4.27 | 14.7 / 14.6 |
| 196 | N | OCH₃ | OCH₃ | H | C—H | OCH₂OCH₃ | H | H | tan solid | 167–169 | 45.6 / 45.2 | 4.33 / 4.20 | 17.7 / 16.9 |
| 197 | N | OCH₃ | OCH₃ | H | C—H | OCH₂CH₂F | H | H | white solid | 203–205 | 45.3 / 44.4 | 4.06 / 3.93 | 17.6 / 17.2 |
| 198 | N | OCH₃ | OCH₃ | H | C—H | OCH₂CF₃ | H | H | white solid | 209–211 | 41.6 / 41.6 | 3.26 / 3.28 | 16.2 / 16.0 |
| 199 | N | OCH₃ | OCH₃ | H | C—H | OC₄H₉(i) | CF₃ | H | tan solid | 217–219 | 45.4 / 45.2 | 4.24 / 4.17 | 14.7 / 14.5 |
| 200 | N | OCH₃ | OCH₃ | H | C—H | CF₃ | OCH₂O | | white solid | 193–195 | 40.3 / 40.2 | 2.70 / 2.74 | 15.7 / 15.4 |
| 201 | N | OCH₃ | OCH₃ | H | C—H | OCH—(CH₂F)₂ | H | H | white solid | 203–204 | 44.8 / 44.9 | 3.99 / 3.91 | 16.3 / 16.2 |
| 202 | N | OCH₃ | OCH₃ | H | C—H | OC₄H₉(s) | CF₃ | H | tan solid | 186–188 | 45.5 / 45.4 | 4.24 / 4.20 | 14.7 / 14.7 |
| 203 | N | OCH₃ | OCH₃ | H | C—H | OCH₂—CH₂Cl | CF₃ | H | off-wht solid | 230–231 | 39.9 / 39.8 | 3.14 / 3.07 | 14.5 / 14.4 |
| 204 | N | OCH₃ | CH₃ | H | C—H | OCH₃ | CF₃ | H | white powder | 135–137 | 43.2 / 43.0 | 3.38 / 3.33 | 16.8 / 16.5 |
| 205 | N | OCH₃ | Br | H | C—H | OCH₂OCH₃ | CF₃ | H | white powder | 197–199 | 35.2 / 35.3 | 2.56 / 2.46 | 13.7 / 13.6 |
| 206 | N | OCH₃ | OC₂H₅ | H | C—H | OCH₂OCH₃ | CF₃ | H | white powder | 175–176 | 41.3 / 42.5 | 3.90 / 3.63 | 15.0 / 14.4 |
| 207 | N | OCH₃ | OCH₃ | H | C—H | OCH₂OCH₃ | CF₃ | H | white | 181–183 | 41.5 | 3.48 | 15.1 |

TABLE 1-continued

SULFONAMIDE COMPOUNDS

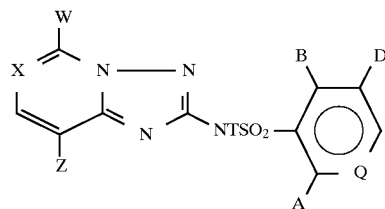

| Cpd. No. | X | W | Z | T | Q | A | B | D | Form | Melting Point, °C | %C | %H | %N |
|---|---|---|---|---|---|---|---|---|---|---|---|---|---|
| 208 | N | OCH₃ | OCH₃ | H | N | OC₂H₅ | CF₃ | H | solid off-wht solid | (d) 211–213 | 41.6 40.2 40.4 | 3.42 3.37 3.33 | 15.0 18.7 18.5 |
| 209 | N | OCH₃ | OCH₃ | H | N | OCH₂CH₂F | CF₃ | H | tan solid | 226–228 | 38.6 38.5 | 3.03 2.88 | 18.0 17.9 |
| 210 | N | OCH₃ | OCH₃ | H | N | OCH₂—CH=CH₂ | CF₃ | H | white solid | 166–168 | 41.7 41.6 | 3.28 3.22 | 18.3 18.0 |
| 211 | N | OCH₃ | OCH₃ | H | N | OC₃H₇(i) | CF₃ | H | white solid | 219–221 | 41.6 41.6 | 3.71 3.66 | 18.2 18.1 |
| 212 | N | OCH₃ | OCH₃ | H | N | OCH₃ | H | CH₃ | white powder | 141–142 | 44.2 43.5 | 4.24 4.07 | 22.1 21.0 |
| 213 | N | OCH₃ | Br | H | N | OCH₃ | CF₃ | H | tan powder | 235–237 (d) | 32.3 32.3 | 2.06 2.06 | 17.4 17.2 |
| 214 | C—H | Br | OCH₃ | H | N | OCH₃ | CF₃ | H | white solid | 241–243 | 34.9 35.0 | 2.30 2.20 | 14.5 14.3 |
| 215 | C—H | OCH₃ | OCH₃ | H | C—H | OC₂H₅ | CO₂CH₃ | H | yellow solid | 197–198 | 49.5 50.0 | 4.62 4.83 | 12.8 12.2 |
| 216 | N | OCH₃ | OCH₃ | SO₂CH₃ | C—H | OCH₃ | CO₂CH₃ | H | tan powder | 230–231 | 39.3 40.3 | 3.91 3.76 | 14.3 13.3 |
| 217 | C—H | OCH₃ | OCH₃ | SO₂CH₃ | C—H | OCH₃ | CO₂CH₃ | H | tan powder | 248–249 (d) | | | |
| 218 | N | OCH₃ | Cl | H | C—H | F | CF₃ | H | tan solid | 191–193 | 36.7 36.7 | 1.89 1.80 | 16.5 16.3 |
| 219 | N | OCH₃ | Cl | H | C—H | OCH₂OCH₃ | CF₃ | H | lt tan solid | 161–163 (d) | 38.5 38.0 | 2.80 2.67 | 15.0 13.8 |
| 220 | N | OCH₃ | OCH₃ | COCH₃ | C—H | OCH₂CH₂F | CF₃ | H | tan powder | 217–220 | 42.6 42.2 | 3.38 3.33 | 15.0 13.6 |
| 221 | N | OCH₃ | OCH₃ | H | C—H | CO₂CH₃ | CF₃ | H | | | | | |
| 222 | N | OCH₃ | OCH₃ | H | C—H | OCF₃ | CF₃ | H | | | | | |
| 223 | N | OCH₃ | OCH₃ | H | C—H | Br | CF₃ | H | | | | | |
| 224 | N | OCH₃ | OCH₃ | H | C—H | OCH₂—CH=CH₂ | CF₃ | H | | | | | |
| 225 | N | OCH₃ | OCH₃ | H | C—H | OCH₂SCH₃ | CF₃ | H | | | | | |
| 226 | N | OCH₃ | OCH₃ | H | C—H | CH₂OCH₃ | CF₃ | H | | | | | |
| 227 | N | OCH₃ | OCH₃ | H | C—H | OC₃H₇(i) | CH₂CF₃ | H | | | | | |
| 228 | N | OCH₃ | OCH₃ | H | C—H | OCH₃ | OCF₂OCH₃ | H | | | | | |
| 229 | N | OCH₃ | OCH₃ | H | C—H | O(CH₂)₃F | CF₃ | H | | | | | |
| 230 | N | OCH₃ | OCH₃ | H | C—H | OCH₂CH₂F | CO₂CH₃ | H | | | | | |
| 231 | N | OCH₃ | OCH₃ | H | C—H | OCF₃ | OCH₂CH₂F | H | | | | | |
| 232 | N | OCH₃ | OCH₃ | H | C—H | OCF₃ | OCH—(CH₂F)₂ | H | | | | | |
| 233 | N | OCH₃ | OCH₃ | H | C—H | OCH-(CH₂Cl)₂ | CF₃ | H | | | | | |
| 234 | N | OCH₃ | OCH₃ | H | C—H | OCH2-CHCl₂ | CF₃ | H | | | | | |
| 235 | N | OCH₃ | OCH₃ | H | C—H | H₃C⧖(O—)(O—) | CF₃ | H | | | | | |
| 236 | N | OCH₃ | OCH₃ | SO₂CH₃ | C—H | OCH₂CH₂F | CF₃ | H | | | | | |
| 237 | N | OCH₃ | OCH₃ | COCH₃ | C—H | OCH₂CH₂F | CF₃ | H | | | | | |
| 238 | N | OCH₃ | OCH₃ | CH₂CH₂—CO₂CH₃ | C—H | OCH₂CH₂F | CF₃ | H | | | | | |
| 239 | N | OCH₃ | OCH₃ | H | C—H | OCH₂CH₂F | H | Cl | | | | | |
| 240 | N | OCH₃ | OCH₃ | H | C—H | OCH₂CF₃ | H | Cl | | | | | |
| 241 | N | OCH₃ | OCH₃ | H | C—H | OCH₃ | H | CH₂F | | | | | |
| 242 | N | OCH₃ | OCH₃ | H | C—H | OCH₃ | CF₃ | Cl | | | | | |

TABLE 1-continued

SULFONAMIDE COMPOUNDS

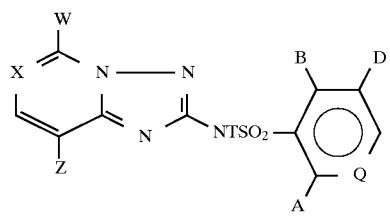

| Cpd. No. | X | W | Z | T | Q | A | B | D | Form | Melting Point, °C | Elem. Anal. Calc./Found % C | % H | % N |
|---|---|---|---|---|---|---|---|---|---|---|---|---|---|
| 243 | N | OCH₃ | OCH₃ | H | C—H | Cl | CF₃ | OCH₃ | | | | | |
| 244 | N | OCH₃ | OCH₃ | H | N | CF₃ | OCH₃ | H | | | | | |
| 245 | N | OCH₃ | OCH₃ | H | N | OCH₃ | CO₂CH₃ | H | | | | | |
| 246 | N | OCH₃ | OCH₃ | H | N | OCH₃ | H | Cl | | | | | |
| 247 | N | OCH₃ | OCH₃ | H | N | OCH₂OCH₃ | CF₃ | H | | | | | |
| 248 | N | OCH₃ | OCH₃ | H | C—H | OCH₃ | CH₂F | H | | | | | |
| 249 | N | OCH₃ | OCH₃ | H | C—H | OCH₃ | SCF₃ | H | | | | | |

The compounds of Formula I wherein T represents hydrogen can be prepared by the reaction of a substituted 2-amino [1,2,4]triazoloazine compound of Formula II:

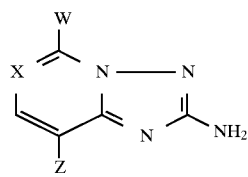

with a benzenesulfonyl chloride or pyridine-3-sulfonyl chloride compound of Formula III:

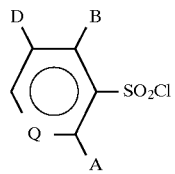

wherein A, B, D, Q, W, X, and Z are as defined herein-above for compounds of Formula I. The reaction can be carried out by combining approximately equal molar amounts of the two compounds in a polar, aprotic solvent, such as acetonitrile, and adding pyridine and a catalytic amount (5 to 25 molar percent of the sulfonyl chloride compound) of dimethyl sulfoxide at room temperature. Additional sulfonyl chloride compound, pyridine, and dimethyl sulfoxide are added, if necessary, to complete the reaction. The reactions take from a few hours to several days to go to completion. Means to exclude moisture, such as a dry nitrogen blanket, are employed. The compounds of Formula I obtained, which are solids with low solubility in many common organic solvents and in water, can be recovered using conventional means.

The condensation reaction of sulfonyl chloride compounds of Formula III and 2-amino[1,2,4]triazoloazine compounds of Formula II can be carried out advantageously by first converting the 2-amino[1,2,4]triazoloazine compound of Formula II into an N-trialkylsilyl derivative of Formula IV:

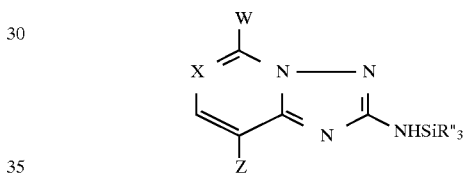

wherein W, X, and Z are as defined for compounds of Formula I and R" represents $C_1$–$C_4$ alkyl. N-Trimethyl-silyl and N-triethylsilyl derivatives are typical. The method is related to those disclosed in U.S. Pat. Nos. 4,910,306 and 4,666,501, but differs in that it generally requires a fluoride ion facilitator.

The conversion of a 2-amino[1,2,4]triazoloazine compound of Formula II to an N-trialkylsilyl derivative of Formula IV can be carried out by preparing a mixture of a chlorotrialkylsilane compound with sodium or potassium iodide in a solvent, such as acetonitrile, under anhydrous conditions and then adding the 2-amino-[1,2,4]triazoloazine compound and a trialkylamine compound, such as triethylamine, typically at ambient temperatures and with agitation. Approximately equimolar amounts of the chlorotrialkylsilane and 2-amino[1,2,4]-triazoloazine compounds are generally employed. The reaction requires from a few hours to a day depending on the specific trialkylamine and 2-amino[1,2,4]triazoloazine compounds involved. The N-trialkylsilyl derivatives prepared can be recovered by diluting the resulting mixture with a non-polar solvent, such as ether or 1,2-dichloroethane, removing the insoluble salts by filtration, and removing the volatile components by evaporation under reduced pressure. Compounds of Formula IV are unstable in the presence of water and must be kept dry.

The 2-(trialkylsilylamino)[1,2,4]triazoloazine derivatives of Formula IV obtained as described above or in other ways can be condensed, with or without further purification, with a sulfonyl chloride compound of Formula III. The condensation is typically carried out in a solvent, such as acetonitrile, in the presence of an approximately equimolar amount of a pyridine or methyl-pyridine base, an approximately equimolar amount of a fluoride ion facilitator, such as cesium fluoride or a tetraalkylammonium fluoride, and a catalytic amount (about 3 to about 20 percent of the sulfonyl chloride compound) of dimethyl sulfoxide. The condensation, which is typically carried out at temperatures of from about 10° C. to about 60° C. under anhydrous conditions with agitation, is generally complete in about 2 to 18 hours. The N-(triazoloazinyl)arylsulfonamide compounds of Formula I obtained can be recovered by conventional means, such as by filtration to collect the solids and extraction of the solids obtained to remove the water-soluble salts and/or soluble organic components.

N-(triazoloazinyl)arylsulfonamide compounds of Formula I wherein T represents other than hydrogen can be prepared from the corresponding compounds of Formula I wherein T represents hydrogen by acylation under reaction conditions known in the art for related sulfonamide acylation reactions. Suitable acylating agents include alkanoyl chloride compounds, such as propionyl chloride or trifluoroacetyl chloride; chloroformate ester compounds, such as 2-methoxyethyl chloroformate; carbamoyl chloride compounds, such as N',N'-diallyl-carbamoyl chloride, and alkyl isocyanate compounds, such as 2-chloroethyl isocyanate.

Compounds of Formula I wherein W represents chloro can be converted into corresponding compounds of Formula I whereby W represents fluoro, bromo, iodo, $O(C_1-C_3$ alkyl), or $S(C_1-C_3$ alkyl) by treatment with an appropriate nucleophile using the general methods for such replacements known in the art. Chloro substituents in the 5-position (X) are generally more easily replaced than are chloro substituents in the 6-position (Y) or the 8-position (Z) and can be selectively replaced.

Many 2-amino[1,2,4]triazolo[1,5-a]pyridine compounds of Formula II (X represents C—Y) can be prepared by the reaction of appropriately substituted N-(2-pyridinyl)-N'-carboethoxythiourea compounds of the formula:

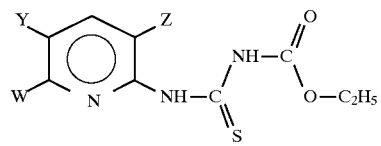

with hydroxylamine. The reaction is typically carried out in a solvent such as ethanol and requires heating for a few hours. The hydroxylamine is typically generated by neutralization of the hydrochloride with a hindered tertiary amine, such as diisopropylethylamine, or an alkali metal alkoxide, such as sodium ethoxide. The desired compounds of Formula II can be recovered by conventional means, such as by removal of the volatile components of the reaction mixture by evaporation, and can be purified by conventional means, such as by extraction with water and/or other solvents in which they are sparingly soluble. The N-(2-pyridinyl)-N'-carboethoxythiourea compound starting materials for this method can be obtained by treatment of appropriately substituted 2-aminopyridine compounds with ethoxycarbonyl isothiocyanate. The reaction is generally carried out in an inert organic solvent at ambient temperatures. The overall method is further described in U.S. Pat. No. 5,571,775.

The substituted 2-aminopyridine compound starting materials for the method described above are known in the art or can be prepared by the methods disclosed herein or by general methods known in the art.

Compounds of Formula II wherein X represents C—Y can also be prepared from appropriately substituted 2-cyanoaminopyridine compounds by the method disclosed by B. Vercek et al. in *Monatshefte fur Chemie,* 114, 789–798 (1983). Additional methods of preparation of such compounds were disclosed by K. T. Potts et al. in *Journal of Organic Chemistry,* 31, 265–273 (1966).

Compounds of Formula I wherein X represents N (2-amino[1,2,4]triazolo[1,5-c]pyrimidine compounds) can be prepared from 4-hydrazinopyrimidine compounds of the formula:

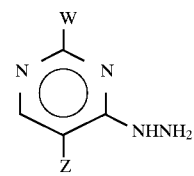

wherein W represents methylthio, hydrogen, or chloro and Z represents hydrogen, halogen, alkoxy, or alkylthio. The hydrazinopyrimidine compound is first treated with cyanogen bromide to produce the hydrobromide of a 3-amino-8-substituted-5-substituted[1,2,4]triazolo-[4,3-c]pyrimidine compound of the formula:

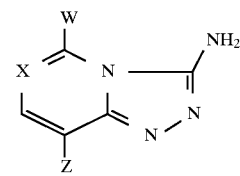

wherein W represents methylthio, hydrogen, or chloro and Z represents hydrogen, halogen, alkoxy, or alkylthio. The reaction is generally carried out in an organic solvent, such as isopropyl alcohol, at ambient temperature. The products can be recovered by conventional means, such as by adding a non-polar solvent, for example diethyl ether, and collecting the solid that forms by filtration. The above intermediates wherein W represents methylthio can then be converted into the desired compounds of Formula II wherein W represents an alkoxy group by treatment with an alkali metal alcoholate, such as sodium methylate or potassium ethylate, and ethyl acrylate in the corresponding alcohol as a solvent. The compound rearranges and the methylthio moiety is replaced by the alkoxy moiety derived from the alcohol of the medium. The reaction is generally carried out at temperatures below 25° C. The desired compounds of Formula II can be recovered by neutralizing with acetic acid and collecting the solids that form by filtration or other conventional means. Compounds of Formula II wherein X represents N and W represents hydrogen or chloro can be obtained from the corresponding [4,3-c] intermediate wherein W represents hydrogen or chloro by isomerization with a trialkylamine base. The 4-hydrazinopyrimidine compound starting materials for these methods can be prepared from the corresponding 4-chloropyrimidine compounds, which are well-known in the art, by reaction with hydrazine.

Other methods of preparation of compounds of Formula II wherein X represents N are disclosed by G. W. Miller, et al., *J. Chemical Society,* 1965, page 3357 and 1963, page 5642.

Compounds of Formula II wherein X represents N are a further embodiment of the invention. Thus, the invention includes 2-amino[1,2,4]triazolo[1,5-c]-pyrimidine compounds of the formula:

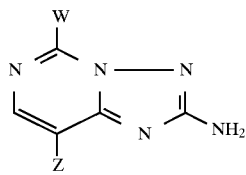

wherein W represents O(C$_1$–C$_3$ alkyl), Cl, Br, F, or H and Z represents O(C$_1$–C$_3$ alkyl), H, F, Cl, Br, I, S(C$_1$–C$_3$ alkyl), or CH 3 optionally substituted with up to three fluorine atoms; with the proviso that at least one of W and Z represents O(C$_1$–C$_3$ alkyl). Compounds of this type wherein one of W and Z represents methoxy and the other represents fluoro, chloro, bromo, methyl, methoxy, or ethoxy are often preferred and such compounds wherein W represents methoxy and Z represents methoxy, fluoro, chloro, or bromo are often more preferred.

The substituted benzenesulfonyl chloride and pyridinesulfonyl chloride starting materials of Formula III can be prepared by the methods disclosed herein or by general or specific methods known in the art. Many such compounds, such as 2-methoxy-6-(trifluoromethyl)benzene-sulfonyl chloride and 2-methoxy-4-(trifluoromethyl)-3-pyridinesulfonyl chloride, can be prepared by lithiation of the corresponding benzene or pyridine compound (e.g., 3-(trifluoromethyl)anisole or 2-methoxy-4-(trifluoromethyl)pyridine with butyl lithium, reaction of the phenyl or pyridinyl lithium compound obtained with dipropyl disulfide, and then chloroxidation of the resulting propylthio compound. In each of these reaction steps conditions generally known for such processes were used. Many propyl or benzylthiobenzenes and pyridines can also be prepared by alkylation of the corresponding thiophenol or 3-pyridinethiol compound using standard methods and subsequent chloroxidation. Phenyl and pyridinyl lithium compounds, such as that derived from 1,3-dimethoxybenzene can be converted directly to the corresponding desired sulfonyl chloride compounds by reaction with sulfur dioxide and sulfuryl chloride in the presence of N,N,N',N'-tetramethylethylenediamine. Other of the required sulfonyl chloride compounds, such as 2-(1,1,2,2-tetrafluoroethoxy)benzenesulfonyl chloride, can be prepared by diazotization of the corresponding aniline or 3-aminopyridine compounds in the presence of sulfur dioxide, copper chlorides, and concentrated aqueous hydrochloric acid. Benzenesulfonyl chloride compounds, such as 2-methoxy-5-methylbenzenesulfonyl chloride, can be prepared by direct chlorosulfonation of appropriate benzene compounds. 3-Alkylthiopyridine compounds having chloro substituents in the 2-and/or 4-positions can be converted to the corresponding compounds having other halo or alkoxy substituents by conventional nucleophilic displacement processes before chloroxidation to produce other pyridine-3-sulfonyl chloride compounds.

Compounds of Formula III wherein Q represents N, including substituted pyridine-3-sulfonyl chloride compounds of the formula:

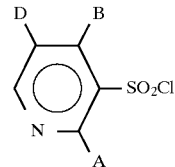

wherein A represents H, F, Cl, Br, or I, or CO$_2$(C$_1$–C$_4$ alkyl) or represents C$_1$–C$_3$ alkyl, O(C$_1$–C$_4$ alkyl), O(C$_3$–C$_4$ alkenyl), O(C$_3$–C$_4$ alkynyl), or S(C$_1$–C$_3$ alkyl) each optionally substituted with one O(C$_1$–C$_3$ alkyl), S(C$_1$–C$_3$ alkyl), chloro, bromo, or cyano substituent or with up to the maximum possible number of fluorine atoms, or represents a 2-methyl-1,3-dioxolan 2-yl moiety; B represents H, F, Cl, Br, I, NO$_2$, CN, CO$_2$(C$_1$–C$_4$ alkyl), NH(C$_1$–C$_3$ alkyl), or N(C$_1$–C$_3$ alkyl) 2 or represents O(C$_1$–C$_4$ alkyl), O(C$_3$–C$_4$ alkenyl), O(C$_3$–C$_4$ alkynyl), C$_1$–C$_3$ alkyl, S(C$_1$–C$_3$ alkyl), SO(C$_1$–C$_3$ alkyl), SO 2(C$_1$–C$_3$ alkyl), S(C$_3$–C$_4$ alkenyl), SO(C$_3$–C$_4$ alkenyl), SO 2(C$_3$–C$_4$ alkenyl), S(C$_3$–C$_4$ alkynyl), SO(C$_3$–C$_4$ alkynyl), or SO 2(C$_3$–C$_4$ alkynyl) each optionally substituted with one O(C$_1$–C$_3$ alkyl), S(C$_1$–C$_3$ alkyl), chloro, bromo, or cyano substituent or with up to the maximum possible number of fluorine atoms; with the proviso that at least one of A and B represents O(C$_1$–C$_4$ alkyl), O(C$_3$–C$_4$ alkenyl), or O(C$_3$–C$_4$ alkynyl) each optionally substituted with one O(C$_1$–C$_3$ alkyl), S(C$_1$–C$_3$ alkyl), chloro, or bromo substituent or with up to the maximum possible number of fluorine atoms; with the proviso that A and B do not simultaneously represent H; and D represents H, F, Cl, Br, I, C$_1$–C$_3$ alkyl, OCH$_3$, OC$_2$H$_5$, or CF$_3$; or B and D together represent a fragment of the formula O—CH$_2$—O, optionally substituted with one or two F or CH$_3$, are further embodiments of the invention. Pyridine-3-sulfonyl chloride compounds of Formula III wherein A represents methoxy, ethoxy, propoxy, 1-methylethoxy, methoxymethoxy, methoxyethoxy, 2-fluoroethoxy, 2-chloro-ethoxy, 2,2-difluoroethoxy, 1-(fluoromethyl) 2-fluoroethoxy, trifluoromethoxy, chloro, or fluoro; B represents hydrogen, methoxy, ethoxy, propoxy, 1-methylethoxy, methoxymethyl, methylthio, methyl, trifluoromethyl, trifluoromethoxy, fluoro, chloro, or methoxycarbonyl; and D represents hydrogen, fluoro, chloro, bromo, or methyl are typically preferred. Such compounds wherein B represents methoxy and D represents hydrogen; wherein A represents methoxy and D represents hydrogen, methyl, or chloro; or wherein B represents trifluoromethyl and D represents hydrogen are often more preferred. Compounds of Formula III wherein Q represents N and A represents methoxy, ethoxy, propoxy, 1-methylethoxy, methoxymethoxy, methoxyethoxy, 2-fluoroethoxy, 2-chloroethoxy, 2,2-difluoroethoxy, or 1-(fluoromethyl) 2-fluoroethoxy; B represents hydrogen, methoxy, ethoxy, propoxy, 1-methylethoxy, trifluoromethyl, or methoxycarbonyl; and D represents hydrogen or methyl are usually most preferred.

While it is possible to utilize the N-(triazoloazinyl) arylsulfonamide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloro-ethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, N-methyl 2-pyrrolidinone, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or non-ionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzene-sulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalenesulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; poly-ethylene glycol esters of fatty acids, such as poly-ethylene glycol stearate; block copolymers of ethylene oxide and propylene oxide; and salts of mono and dialkyl phosphate esters.

Other adjuvants commonly utilized in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions can also contain other compatible components, for example, other herbicides, herbicide safeners, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The compounds of Formula I have been found to be useful preemergence (including pre-plant) and post-emergence herbicides. Postemergence applications are generally preferred. The compounds are effective in the control of both broadleaf and grassy weeds. While each of the N-(triazoloazinyl) arylsulfonamide compounds encompassed by Formula I is within the scope of the invention, the degree of herbicidal activity, the crop selectivity, and the spectrum of weed control obtained varies depending upon the substituents and other features present. The compounds can be employed at higher, non-selective rates of application to control essentially all of the vegetation in an area. Compounds 10, 13, 14, 15, 18, 23, 26, 27, 28, 36, 37, 38, 39. 41, 50, 53, 54, 60, 63, 65, 77, 80, 81, 92, 105, 106, and 139 are among the compounds that are of special interest for this purpose. In many cases, the compounds can also be employed at lower, selective rates of application for the control of undesirable vegetation in grass crops, such as corn, sorghum, wheat, barley, and rice as well as in broadleaf crops, such as oil-seed rape, soybeans, and cotton. Their use in the control of selective grassy weeds, such as blackgrass and wild oats, and some broadleaf weeds in small grain crops, such as wheat and barley, is of special interest. Compounds 28, 34, 53, 96, 98, 105, and 142 are among the better compounds for this purpose. Many of the compounds can be used to remove broadleaf weeds from small grain crops, such as wheat. Compounds of special interest for this purpose include compounds 1, 2, 21, 32, 43, 46, 52, 95, 109, 120, 122, and 126. Many of the compounds are also useful for the control of many broadleaf and grassy weeds in rice. Compounds of special interest for this purpose include compounds 167, 177, 184, 185, 187, 188, 190, 194, 195, 203, 209, 210, 220, 229, & 233. Undesirable vegetation can be removed from rice that is either direct seeded or transplanted and is grown either in paddies or upland. The selectity to rice can often be improved by the use of safeners. Some of the compounds, such as compounds 55 and 106, can be employed to remove broadleaf and grassy weeds from oil-seed rape.

The term herbicide is used herein to mean an active ingredient which controls or adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation are meant to include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I post-emergence to relatively immature plants to achieve the maximum control of weeds.

Application rates of about 0.001 to about 1 Kg/Ha are generally employed in postemergence operations; for preemergence applications, rates of about 0.01 to about 2 Kg/Ha are generally employed. The higher rates designated generally give non-selective control of a broad variety of undesirable vegetation. The lower rates typically give selective control and, by judicious election of compounds, timing, and rates of application, can be employed in the locus of crops.

The compounds of the present invention (Formula I) are often applied in conjunction with one or more other herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed beneficially in combination with the compounds of the present invention include substituted triazolopyrimidinesulfonamide compounds, such as N-(2,6-dichlorophenyl)-5-ethoxy-7-fluoro[1,2,4]triazolo[1,5-c]pyrimidine 2-sulfonamide (diclosulam), N-(2-methoxycarbonyl-6-chlorophenyl)-5-ethoxy-7-fluoro[1,2,4]triazolo[1,5-c]pyrimidine-2-sulfonamide (cloransulam-methyl), and N-(2,6-difluoro-phenyl)-5-methyl[1,2,4]triazolo[1,5-a]pyrimidine 2-sulfonamide (flumetsulam). Other herbicides such as acifluorfen, bentazon, chlorimuron, clomazone, lactofen, carfentrazone-methyl, fumiclorac, fluometuron, fomesafen, imazaquin, imazethapyr, linuron, metribuzin, fluazifop, haloxyfop, glyphosate, glufosinate, 2,4-D, acetochlor, metolachlor, sethoxydim, nicosulfuron, clopyralid, fluroxypyr, metsulfuron-methyl, amidosulfuron, tribenuron, and others can also be employed. It is generally preferred to use the compounds in conjunction with other herbicides that have a similar crop selectivity. It is further usually preferred to apply the herbicides at the same time, either as a combination formulation or as a tank mix.

The compounds of the present invention can generally be employed in combination with a wide variety of known herbicide safeners, such as cloquintocet, mefenpyr, furilazole, dichlormid, benoxacor, flurazole, fluxofenim, daimuron, dimepiperate, thiobencarb, and fenclorim, to enhance their selectivity. Herbicide safeners that act by modifying the metabolism of herbicides in plants by enhancing the activity of cytochrome P-450 oxidases are usually especially effective. This is often a preferred embodiment of the invention. The compounds can additionally be employed to control undesirable vegetation in many crops that have been made tolerant to or resistant to herbicides by genetic manipulation or by mutation and selection. For example, corn, wheat, rice, soybean, sugarbeet, cotton, canola, and other crops that have been made tolerant or resistant to herbicides in general or to herbicides that inhibit the enzyme acetolactate synthase in sensitive plants can be treated.

EXAMPLES

The following Examples are presented to illustrate the various aspects of this invention and should not be construed as limitations to the claims.

1. Preparation of 2-Propylthio-3-(trifluoromethyl)-anisole

A solution of 30 mL (milliliter) (208 mmol) (millimole) of 3-(trifluoromethyl)anisole in 500 mL of dry tetrahydrofuran was cooled to −70° C. under a nitrogen blanket and 100 mL (250 mmol) of 2.5M butyl lithium in hexane was added slowly with stirring and cooling. The reddish solution was stirred at −70° C. for 1 hour and then 42 mL (270 mmol) of dipropyl disulfide was added slowly with stirring and cooling. The resulting mixture was allowed to warm to ambient temperature over an 18-hour period. The mixture was quenched with 250 mL of saturated aqueous ammonium chloride. The organic phase was recovered, dried over magnesium sulfate, and concentrated by evaporation under reduced pressure. The yellow oil residue was fractionally distilled in a Vigreux column at 0.2 mm Hg (millimeters of mercury) (27 Pascals) to obtain 37 g (gram) (71 percent of theory) of a clear liquid product fraction boiling at 92° C. This fraction was found to be 82 percent the title compound, 10 percent the isomer 2-propylthio-5-(trifluoromethyl) anisole.

Elemental Analysis $C_{11}H_{13}F_3OS$ Calc.: %C, 52.8; %H, 5.24; %S, 12.8 Found: %C, 52.7; %H, 5.11; %S, 11.9

NMR: $^1H$ (CDCl$_3$): 7.02(m, 3H), 3.96(s, 3H), 2.83(t, 2H, J=7.4), 1.54–1.04(m, 2H), 0.93(t, 3H, J=7.4).

2. Preparation of 2-(Benzylthio)anisole

A solution of 25.0 g (178 mmol) of 2-methoxy-thiophenol in 50 mL of dry tetrahydrofuran was added dropwise to a mixture of 22.0 g (196 mmol) of potassium t-butoxide and 100 mL of tetrahydrofuran at 0° C. with stirring. A solution of 25 mL (214 mmol) of benzyl chloride in 50 mL of tetrahydrofuran was added to this with stirring and cooling and the mixture was then allowed to warm to ambient temperature and was stirred for 18 hours. The resulting mixture was concentrated by evaporation under reduced pressure and the residue was diluted with 300 mL of dichloromethane. The solution obtained was washed with water, dried over magnesium sulfate, and concentrated by evaporation under reduced pressure. The residue was the title compound, a white solid melting at 69°–70° C.

Elemental Analysis $C_{14}H_{14}OS$ Calc.: %C, 73.0; %H, 6.13; %S, 13.9 Found: %C, 73.0; %H, 6.13; %S, 13.7

NMR: $^1H$ (CDCl$_3$): 7.2(m, 7H), 6.8(m, 2H), 4.1(s, 2H), 3.90(s, 3H).

3. Preparation of Methyl 2-Propylthio-3-methoxybenzoate

A solution of 65.3 g (318 mmol) of 3-(4,4-dimethyloxazolin 2-yl)anisole in 400 mL of dry tetrahydrofuran was cooled to −70° C. and then 165.5 mL (414 mmol) of 2.5M butyl lithium was added with cooling and stirring. The burgundy solution was warmed to −40° C. with stirring for 90 min. It was then cooled to −70° C. and a solution of 62.2 g (414 mmol) of dipropyl disulfide in 100 mL of dry tetrahydrofuran was added dropwise with stirring and cooling. The resulting mixture was allowed to warm to ambient temperature over a 90-min period and the pink, milky suspension obtained was neutralized with 300 mL of saturated aqueous ammonium chloride. The phases were separated and the organic phase was dried over magnesium sulfate, filtered, and concentrated by evaporation under reduced pressure. The residual gold oil was fractionally distilled at 0.6 mm Hg (80 Pascals) in a 2×10 cm (centimeter) Vigreux column to obtain 76.0 g (86 percent of theory) of 2-propylthio-3-(4,4-dimethyloxazolin 2-yl) anisole as a light yellow oil boiling at 155°–157° C. (0.6 mm Hg).

NMR: $^1H$ (CDCl$_3$): 7.25(t, 1H, J=7.8), 7.06(dd, 1H, J=7.6, 1.3), 6.90(dd, 1H, J=8.3, 1.2), 4.09(s, 2H), 3.87(s, 3H), 2.76(t, 2H, J=7.2), 1.44(m, 2H), 1.37(s, 6H), 0.89(t, 3H, J=7.4).

A suspension of 58.2 g (209 mmol) of 2-propyl-thio-3-(4,4-dimethyloxazolin 2-yl)anisole in 6N aqueous hydrochloric acid was heated at reflux with stirring for 18 hours. The resulting homogeneous solution was extracted with 3×100 mL of diethyl ether and the combined extracts were dried over magnesium sulfate, filtered, and concentrated by evaporation under reduced pressure. The resulting amber oil was purified by flash chromatography on a silica gel column eluting with mixtures of hexane and ethyl acetate. The product-containing fractions were combined and concentrated by evaporation under reduced pressure to obtain 38.7 g (82 percent of theory of 2-propylthio-3-methoxybenzoic acid as a viscous gold oil.

NMR: $^1$H (CDCl$_3$): 12.3(brs, 1H), 7.55(dd, 1H, J=7.8, 1.1), 7.33(t, 1H, J=8.1), 7.0(dd, 1H, J=8.3, 0.9), 3.88(s, 3H), 2.80(t, 2H, J=7.5), 1.49(m, 2H), 0.90(t, 3H, J=7.3).

A suspension of 38.1 g (169 mmol) of 2-propyl-thio-3-methoxybenzoic acid in 100 g (843 mmol) of thionyl chloride was prepared and stirred at ambient temperature for 18 hours. The resulting solution was concentrated by evaporation under reduced pressure to obtain 39.7 g of crude acid chloride. A 8.7 g (36 mmol) portion of this was dissolved in 100 mL of dry methanol, the solution was cooled to 0° C., and 4.7 g (46 mmol) of triethylamine was added with stirring and cooling. The mixture was allowed to warm to ambient temperature over 18 hours with stirring. The resulting mixture was concentrated by evaporation under reduced pressure and the dark, oily residue was dissolved in 250 mL of diethyl ether. The ethereal solution was washed with 2×200 mL of water, dried over magnesium sulfate, filtered, and concentrated by evaporation under reduced pressure to obtain 8.4 g (99 percent of theory) of the title compound as a dark oil.

NMR: $^1$H (CDCl$_3$): 7.26(t, 1H, J=8.2), 7.03(d, 1H, J=8.4), 6.92(d, 1H, J=8.2), 3.87(s, 3H), 2.77(t, 2H, J=7.4), 1.45(m, 2H), 0.89(t, 3H, J=7.4).

4. Preparation of 2-Methoxy-3-propylthio-4-(trifluoromethyl)pyridine

A solution prepared by adding 110 mL (154 mmol) of 1.4M methyl lithium in diethyl ether to 70 mL of dry tetrahydrofuran under a nitrogen blanket was cooled with a dry ice/acetone bath and to it was added with cooling and stirring 12.4 g (70 mmol) of 2-methoxy-4-(trifluoro-methyl) pyridine and 0.92 mL (7 mmol) of diisopropylamine. The mixture was allowed to warm to −40° C. was then recooled in a dry ice/acetone bath. Dipropyl disulfide (33 mL, 210 mmol) was added dropwise with stirring and cooling. The resulting mixture was allowed to warm to ambient temperature and was then diluted with 150 mL of water and extracted with diethyl ether. The ethereal extract was dried over magnesium sulfate and concentrated by evaporation under reduced pressure. The tan oil residue was purified by chromatography on silica gel eluting with a mixture of hexane and ethyl acetate to obtain 14.1 g (80 percent of theory) of the title compound as a light yellow oil. Elemental Analysis C$_{10}$H$_{12}$NF$_3$OS Calc.: %C, 47.8; %H, 4.81; %N, 5.57; %S, 12.8 Found: %C, 48.1; %H, 5.33; %N, 5.33; %S, 12.7

NMR: $^1$H (CDCl$_3$) : 8.18(d, 1H, J=5.7), 7.12(d, 1H, J=5.7), 4.00(s, 3H), 2.85(t, 2H, J=7.4), 1.47–1.46(m, 2H), 0.93(t, 3H, J=7.2).

The following 3-propylthiopyridine compounds were prepared similarly:

2-Methoxy-3-propylthiopyridine—a colorless oil boiling at 80° C. under 0.3 mm Hg (40 Pascals) pressure;

Elemental Analysis C$_9$H$_{13}$OS Calc.: %C, 59.0; %H, 7.15 Found: %C, 59.1; %H, 7.12;

2Chloro-4-methoxy-3-propylthiopyridine—a clear oil;

NMR: $^1$H (CDCl$_3$): 8.21(d, 1H, J=5.6), 6.77(d, 1H, J=5.6), 3.97(s, 3H), 2.85(t, 2H, J=7.5), 1.57–1.50(m, 2H), 0.99(t, 3H, J=7.3); and 4-Chloro 2-methoxy-3-propylthiopyridine—a yellow oil;

NMR: $^1$H (CDCl$_3$): 7.96(d, 1H, J=5.2), 6.98(d, 1H, J=5.6), 4.02(s, 3H), 2.88(t, 2H, J=7.3), 1.54–1.51(m, 2H), 0.96(t, 3H, J=7.8).

5. Preparation of 2-Methoxy-6-(trifluoromethyl)benzenesulfonyl Chloride

A mixture containing 20.0 g (80 mmol) of an 82:10:8 mixture of 2-propylthio-3-(trifluoromethyl)-anisole: 2-propylthio-5-(trifluoromethyl)anisole: unknown, 250 mL of chloroform, and 125 mL of water was cooled to 0° C. with an ice bath and 21.6 g (305 mmol) of chlorine gas was added slowly with stirring. After 2.5 hours the organic phase was separated, dried over magnesium sulfate, and concentrated by evaporation under reduced pressure. The residual clear oil was mixed with 100 mL of pentane and the mixture was allowed to stand at ambient temperature for 18 hours and under refrigeration for 3 hours to crystallize the oil. The solids were collected by filtration to obtain 11.9 g (54 percent of theory) of the title compound as white crystals melting at 86°–88° C.

NMR: $^1$H (CDCl$_3$): 7.8(dd, 1H, J=7.9, 8.6), 7.53(d, 1H, J=7.9), 7.46(d, 1H, J=8.6), 4.1(s, 3H).

6. Preparation of 2-Methoxybenzenesulfonyl Chloride

A solution of 34.1 g (149 mmol) of 2-(benzyl-thio)anisole in 300 mL of chloroform was combined with 150 mL of water and the mixture cooled with an ice bath. Chlorine gas (39 g, 550 mmol) was added to this with cooling and stirring at a rate such that the temperature remained below 5° C. The ice bath was then removed and the yellow mixture was allowed to warm to ambient temperature and stir for 18 hours. The layers were then separated and the chloroform layer was dried over magnesium sulfate and concentrated by evaporation under reduced pressure. The residue was an oil that on standing formed 21.3 g (69 percent of theory) of white crystals of the title compound melting at 52°–53° C.

NMR: $^1$H (CDCl$_3$): 7.93–7.76(m, 1H), 7.70–7.65(m, 1H), 7.13–7.06(m, 1H), 4.0(s, 3H).

7. Preparation of Methyl 2-Chlorosulfonyl-3-methoxybenzoate

A mixture of 7.8 g (32 mmol) of methyl 3-methoxy 2-propylthiobenzoate, 2.3 g (130 mmol) of water, and 30 mL of glacial acetic acid was prepared and warmed to 45° C. Chlorine gas (7.6 g, 107 mmol) was added with stirring. The dark mixture turned light orange and the temperature rose to 75° C. After 1 hour the mixture was poured into 600 mL of ice and water and stirred until all of the ice melted. The solids present were recovered by filtration and dissolved in 500 mL of diethyl ether. The ether solution was dried over magnesium sulfate, filtered, and concentrated by evaporation under reduced pressure. The tan solid residue was flash chromatographed on silica gel eluting with a mixture of hexane and ethyl acetate. The product-containing fractions were combined and concentrated by evaporation under reduced pressure to obtain 5.32 g (62 percent of theory) of the title compound as a light pink solid melting at 106.5°–108.5° C.

Elemental Analysis C$_9$H$_9$ClO$_5$S Calc.: %C, 40.8; %H, 3.43; %S, 12.1 Found: %C, 40.7; %H, 3.62; %S, 11.8

NMR: $^1$H (CDCl$_3$) : 7.68(t, 1H, J=8.0), 7.21(d, 1H, J=8.7) 7.03(d, 1H, J=7.5), 4.05(s, 3H), 3.90(s, 3H).

8. Preparation of 2,6-Dimethoxybenzenesulfonyl Chloride

A solution of 15.0 g (108 mmol) of 1,3-dimethoxybenzene and 13.8 g (119 mmol) of N,N,N',N'-tetramethylethylenediamine in 225 mL of dry petroleum ether was prepared and cooled to 0° C. and then 47.5 mL (119 mmol) of 2.5M butyl lithium in hexane was added with cooling and stirring. After 1 hour the mixture was cooled to about −72° C. and about 70 g (1 mol) of sulfur dioxide was added with stirring as a saturated solution in 100 mL of dry diethyl ether. The resulting light yellow mixture was warmed to 10° C. over a 2-hour period and then the sticky yellow solids present were collected by filtration and washed with several portions of dry diethyl ether. The solids were suspended in 400 mL of dry hexane, the suspension cooled to 0° C., and 14.6 g (108 mmol) of sulfuryl chloride as a solution in 200 mL of dry hexane was added with stirring and cooling. After 45 min at 0° C. the resulting pink solids were collected by filtration, washed with cold hexane, and dissolved in diethyl ether. The resulting solution was washed with 3×150 mL of cold water, dried over magnesium sulfate, filtered, and concentrated by evaporation under reduced pressure to obtain 19.4 g (76 percent of theory) of the title compound as a light yellow crystalline solid melting at 89°–91° C.

NMR: $^1$H (CDCl$_3$): 7.51(t, 1H, J=8.5), 6.64(d, 2H, J=8.5), 3.92(s, 6H).

The following compound was prepared similarly: 2,4-Dimethoxypyridine-3-sulfonyl chloride—a tan solid melting at 118°–120° C.;

NMR: $^1$H (CDCl$_3$): 8.26(d, 1H, J=5.9), 6.66(d, 1H, J=5.9), 4.11(s, 3H), 4.05(s, 3H).

9. Preparation of 2-Ethoxy-5-methylbenzenesulfonyl Chloride

A solution of 6.8 g (50 mmol) of 4-ethoxy-toluene in 20 mL of dichloromethane was added to a solution of 10 mL (150 mmol) of chlorosulfonic acid in 10 mL of dichloromethane at 0° C. with cooling and stirring. The mixture was stirred 1 hour at 0° C. and was then warmed to ambient temperature and stirred another hour. The resulting tan solution was poured into 200 mL of ice water and the mixture was extracted with dichloromethane. The extract was dried over magnesium sulfate and concentrated by evaporation under reduced pressure. The residual 7.9 g (68 percent of theory) of light tan solid melting at 59°–61° C. was the title compound.

NMR: $^1$H (CDCl$_3$): 7.71(d, 1H, J=2.2), 7.4(dd, 1H, J=8.5, 2.2), 6.95(d, 1H, J=8.5), 4.23q, 2H, J=7.0), 1.49(t, 3H, j=7.0).

10. Preparation of 2-Methoxy-4-(trifluoromethyl)-pyridine-3-sulfonyl Chloride

Fifty mL of water was combined with a solution of 7.0 g (28 mmol) of 2-methoxy-3-propylthio-4-(trifluoromethyl) pyridine in 100 mL of dichloromethane and the mixture was cooled with an ice bath. Chlorine gas (5.1 mL, 112 mmol) was added slowly with stirring and cooling. The mixture was then allowed to warm to ambient temperature and stir for 3 hours. The layers were separated and the organic layer was dried over magnesium sulfate and concentrated by evaporation under reduced pressure. The yellow oil residue was purified by chromatography on silica gel eluting with a mixture of hexane and ethyl acetate. The fractions containing product were combined and concentrated by evaporation under reduced pressure to obtain 4.9 g (64 percent of theory) of the title compound as a light yellow oil.

NMR: $^1$H (CDCl$_3$): 8.6(d, 1H, J=5.4), 7.4(d, 1H, J=5.4), 4.2(s, 3H). The mass spectrum had a parent peak M$^+$275.

The following pyridine-3-sulfonyl chloride compounds were prepared similarly:
4-Chloro 2-methoxypyridine-3-sulfonyl chloride;

NMR: $^1$H (CDCl$_3$): 8.23(d, 1H, J=5.6), 7.11(d, 1H, J=5.2), 4.17(s, 3H); mass spectrum parent peak M$^+$275;
2-Chloro-4-methoxypyridine-3-sulfonyl chloride—a tan crystalline solid;

NMR: $^1$H (CDCl$_3$): 8.47(d, 1H, J=5.9), 7.03(d, 1H, J=5.9), 4.13(s, 3H) ; and 2-Methoxypyridine-3-sulfonyl chloride—a clear oil;

NMR: $^1$H (CDCl$_3$): 8.46–8.44(dd, 1H, J=1.9, 4.9), 8.22–8.19(dd, 1H, J=1.9, 7.8), 7.08–7.04(dd, 1H, J=4.9, 7.8), 4.16(s, 3H).

11. Preparation of 2-(1,1,2,2-Tetrafluoroethoxy)benzenesulfonyl Chloride

A solution containing 3.8 g (55 mmol) of sodium nitrite in 6 mL of water was added slowly with cooling and stirring to a mixture of 12.3 g (50 mmol) of 2-(1,1,2,2-tetrafluoroethoxy)aniline, 18 mL of concentrated aqueous hydrochloric acid, and 5 mL of acetic acid that was precooled to −10° C. After 45 min, the resulting mixture was added in portions to a −10° C. solution of 1.3 g (18 mmol) of cuprous chloride and 0.5 g (4 mmol) of cupric chloride in 50 mL of acetic acid saturated with sulfur dioxide (more than 12 g). The mixture was then warmed to ambient temperature and stirred for 90 min after which it was poured onto ice. The mixture obtained was extracted with diethyl ether and the extract was washed with water, dried over magnesium sulfate, and concentrated by evaporation under reduced pressure. The residue was chromatographed on silica gel eluting with a mixture of hexane and ethyl acetate. The fractions containing product were combined and concentrated by evaporation under reduced pressure to obtain 11.0 g (75 percent of theory) of the title compound as a yellow oil. NMR: $^1$H (CDCl$_3$): 8.07(dd, 1H, J=1.7, 8.0), 7.76(ddd, 1H, J=1.7, 7.8, 8.1), 7.59(dd, 1H, J=1.2, 8.1), 7.45(ddd, 1H, J=1.2, 7.8, 8.0), 6.05(tt, 1H, J=4.0, 53.0). The mass spectrum had a parent peak M$^+$292.

12. Preparation of 3-Amino-8-chloro-5-methylthio[1,2,4]-triazolo[4,3-c]pyrimidine Hydrobromide A solution of 40 mL (120 mmol) of 3 molar cyanogen bromide in dichloromethane was combined with 19.0 g (100 mmol) of 5-chloro-4-hydrazino 2-methylthio-pyrimidine and 200 mL of dry isopropyl alcohol at ambient temperature with stirring. The resulting mixture was stirred for 18 hours and then diluted with 500 mL of diethyl ether. The solids that formed were recovered by filtration and dried to obtain the theoretical amount of the title compound as a yellow solid melting above 250° C.

Elemental Analysis C$_6$H$_7$N$_5$BrClS Calc.: %C, 24.3; %H, 2.38; %N, 23.6; %S, 10.8 Found: %C, 26.1; %H, 2.69; %N, 24.0; %S, 12.2;

NMR: $^1$H (DMSO-d6): 7.80(s, 1H), 2.67(s, 3H); $^{13}$C: 150.96, 147.90, 143.10, 138.38, 113.16, 14.22.

The following 3-amino[1,2,4]triazolo[4,3-c]pyrimidine compounds were prepared similarly:
3-Amino-8-fluoro-5-methylthio[1,2,4]triazolo[4,3-c]-pyrimidine hydrobromide—a yellow solid melting at 168°–170° C.;

Elemental Analysis C$_6$H$_7$N$_5$BrFS Calc.: %C, 25.7; %H, 2.51; %N, 25.0; %S, 11.4 Found: %C, 25.7; %H, 2.52; %N, 25.0; %S, 11.5;

3-Amino-8-methoxy-5-methylthio[1,2,4]triazolo[4,3-c]-pyrimidine hydrobromide—a tan solid melting at 180°–182° C.;

Elemental Analysis C$_7$H$_{10}$N$_5$BrOS Calc.: %C, 28.8; %H, 3.45; %N, 24.0; %S, 11.0 Found: %C, 29.0; %H, 3.44; %N, 23.9; %S, 11.1;

3-Amino-8-iodo-5-methylthio[1,2,4]triazolo[4,3-c]-pyrimidine hydrobromide—a yellow solid melting at 197°–199° C.;

Elemental Analysis C$_6$H$_7$N$_5$BrIS Calc.: %C, 18.6; %H, 1.82; %N, 18.1; %S, 8.26 Found: %C, 19.0; %H, 2.28; %N, 18.0; %S, 8.54;

3-Amino-8-bromo-5-methylthio[1,2,4]triazolo[4,3-c]-pyrimidine hydrobromide—a yellow solid melting at 193°–195° C.;

Elemental Analysis C$_6$H$_7$N$_5$Br$_2$S Calc.: %C, 21.1; %H, 2.07; %N, 20.5; %S, 9.40 Found: %C, 21.3; %H, 2.14; %N, 20.6; %S, 9.33;

3-Amino-8-methyl-5-methylthio[1,2,4]triazolo[4,3-c]-pyrimidine hydrobromide—a yellow solid melting at 234°–236° C.;

Elemental Analysis C$_7$H$_{10}$N$_5$BrS Calc.: %C, 30.6; %H, 3.30; %N, 25.5; %S, 11.7 Found: %C, 30.7; %H, 3.52; %N, 25.3; %S, 11.5;

3-Amino-8-ethoxy-5-methylthio[1,2,4]triazolo[4,3-c]-pyrimidine hydrobromide—a yellow powder melting at 160°–163° C.; and 3-Amino-5-methylthio[1,2,4]triazolo[4,3-c]pyrimidine hydrobromide—a tan solid;

NMR: $^1$H (DMSO-d6): 7.52(d, 1H, J=6.6), 7.13(d, 1H, J=6.7), 6.08(s, 2H), 2.61(s, 3H).

13. Preparation of 2-Amino-8-chloro-5-methoxy[1,2,4]-triazolo[1,5-c]pyrimidine

A mixture of 15.0 g (51 mmol) of 3-amino-8-chloro-5-methylthio[1,2,4]triazolo[4,3-c]pyrimidine hydrobromide, 8.2 mL (76 mmol) of ethyl acrylate, and 150 mL of methanol was prepared and cooled in an ice bath. A solution of 17 mL (76 mmol) of 4.5 molar sodium methoxide in methanol was added to this slowly with cooling and stirring. When the addition was complete, the mixture was allowed to warm to ambient temperature and was stirred for 18 hours. It was then neutralized with 2.0 mL of acetic acid. The solids that formed were recovered by filtration, washed with diethyl ether, and dried to obtain 7.7 g (75 percent of theory) of the title compound as a tan powder melting above 250° C.

Elemental Analysis C$_6$H$_6$N$_5$ClO Calc.: %C, 36.1; %H, 3.03; %N, 35.1% Found: %C, 36.1; %H, 3.19; %N, 34.8%

NMR: $^1$H (DMSO-d6): 8.0(s, 1H), 6.6(brs, 2H), 4.1 (s, 3H); $^{13}$C 166.40, 151.65, 147.73, 140.95, 108.57, 56.12.

The following 2-amino[1,2,4]triazolo[1,5-c]pyrimidine compounds were prepared similarly:

2-Amino-8-fluoro-5-methoxy[1,2,4]triazolo[1,5-c]-pyrimidine—tan needles melting above 230° C.;

Elemental Analysis C$_6$H$_6$N$_5$FO Calc.: %C, 39.4; %H, 3.30; %N, 38.2% Found: %C, 39.5; %H, 3.28; %N, 37.7%;

2-Amino-5,8-dimethoxy[1,2,4]triazolo[1,5-c] pyrimidine—a tan powder melting at 201°–203° C.;

Elemental Analysis C$_7$H$_9$N$_5$O$_2$ Calc.: %C, 43.1; %H, 4.65; %N, 35.9% Found: %C, 43.2; %H, 4.67; %N, 35.6%;

2-Amino-7-fluoro-5-methoxy[1,2,4]triazolo[1,5-c]-pyrimidine—a tan powder melting above 250° C.;

Elemental Analysis C$_6$H$_6$N$_5$FO Calc.: %C, 39.4; %H, 3.30; %N, 38.2% Found: %C, 39.6; %H, 3.31; %N, 38.2%;

2-Amino-8-iodo-5-methoxy[1,2,4]triazolo[1,5-c] pyrimidine—a tan solid melting above 250° C.;

Elemental Analysis C$_6$H$_6$N$_5$IO Calc.: %C, 24.8; %H, 2.08; %N, 24.1% Found: %C, 25.0; %H, 1.96; %N, 23.8%;

2-Amino-8-methyl-5-methoxy[1,2,4]triazolo[1,5-c]-pyrimidine—a tan solid melting above 250° C.;

Elemental Analysis C$_7$H$_9$N$_5$O Calc.: %C, 46.9; %H, 5.06; %N, 39.1% Found: %C, 46.7; %H, 4.84; %N, 39.1%;

2-Amino-8-ethoxy-5-methoxy[1,2,4]triazolo[1,5-c]-pyrimidine—a light tan solid melting at 190°–191° C.; and 2-Amino-5-methoxy[1,2,4]triazolo[1,5-c]pyrimidine—a tan solid melting above 250° C.;

NMR: $^1$H (DMSO-d6): 7.82(d, 1H, J=6.3), 7.03(d, 1H, J=6.1), 6.31(s, 2H), and 4.12(s, 3H).

14. Preparation of 2-(N-Trimethylsilylamino)-8-chloro-5-methoxy[1,2,4]triazolo[1,5-c]pyrimidine A mixture of 12.7 g (85 mmol) of sodium iodide in 425 mL of dry acetonitrile was prepared under nitrogen in a predried 2 L flask and to this mixture 9.25 g (10.8 mL, 85 mmol) of chlorotrimethylsilane was added by means of a syringe at ambient temperature with stirring. After 10 min, 17.0 g (85 mmol) of 2-amino-8-chloro-5-methoxy-[1,2,4] triazolo[1,5-c]pyrimidine and 8.62 g (11.9 mL, 85 mmol) of triethylamine were added with stirring. The mixture was allowed to react for 12 hours at ambient temperature with stirring and was then diluted with 500 mL of dry diethyl ether. The salts that precipitated were removed by filtration on a dry scintered glass filter and the filtrate was concentrated by evaporation under reduced pressure. The residue was diluted with another 500 mL of dry diethyl ether the salt removal procedure was repeated. The title compound was obtained as the solid residue and amounted to 19.5 g (84 percent of theory).

15. Preparation of (N-(8-Chloro-5-methoxy[1,2,4]-triazolo [1,5-c]pyrimidin 2-yl)-2-methoxy-6-(trifluoro-methyl) benzenesulfonamide A solution of 19.5 g (72 mmol) of 2-(N-trimethylsilylamino)-8-chloro-5-methoxy[1,2,4]triazolo-[1,5-c]pyrimidine dissolved in 150 mL of dry acetonitrile was prepared and 27.5 g (100 mmol) of 2-methoxy-6-(trifluoromethyl)benzenesulfonyl chloride was added at ambient temperature under nitrogen with stirring. To this was added sequentially with stirring 6.7 g (6.9 mL, 85 mmol) of dry pyridine, 0.66 g (0.60 mL, 8.5 mmol) of dry dimethyl sulfoxide, and 13.7 g (85 mmol) of cesium fluoride. The mixture was allowed to react for 8 hours and then the solids present were recovered by filtration. These solids were slurried in 100 mL of 0.38 percent aqueous hydrochloric acid and recovered by filtration and then slurried in 100 mL of methanol and recovered by filtration. The white solid recovered was dried to obtain 21.3 g (68 percent of theory) of the title compound melting at 216°–217° C.

Elemental Analysis C$_{14}$H$_{11}$N$_5$ClF$_3$O$_4$S Calc.: %C, 38.4; %H, 2.53; %N, 16.0 Found: %C, 38.6; %H, 2.50; %N, 16.1

16. Preparation of (N-(8-Chloro-5-methoxy[1,2,4]triazolo [1,5-c]pyrimidin 2-yl)-2,6-dimethoxybenzenesulfonamide A suspension of 0.80 g (4.0 mmol) of 2-amino-8-chloro-5-methoxy[1,2,4]triazolo[1,5-c]pyrimidine in 15 mL of dry acetonitrile was prepared and 1.90 g (8.0 mmol of 2,6-dimethoxybenzenesulfonyl chloride, 0.63 g (8.0 mmol) of dry pyridine, and 0.08 g (1 mmol) of dry dimethyl sulfoxide were added with stirring at ambient temperature, keeping the system dry. After 18 hours another 0.32 g of dry pyridine was added and after another 18 hours another 0.08 g of dry dimethyl sulfoxide was added. After 1 more hour the mixture was diluted with 350 mL of dichloromethane and the resulting mixture was washed with 3×150 mL of water, dried over magnesium sulfate, filtered, and concentrated by evaporation under reduced pressure. The orange oil residue was triturated with diethyl ether to obtain the title compound as a light yellow solid which, after drying, amounted to 1.41 g (88 percent of theory) and melted at 215.5–217.5.

Elemental Analysis C$_{14}$H$_{14}$N$_5$ClO$_5$S Calc.: %C, 42.1; %H, 3.53; %N, 17.5; %S, 8.02 Found: %C, 42.2; %H, 3.62; %N, 17.1; %S, 7.70

NMR: $^1$H (DMSO-d6): 11.74(S, 1H), 8.10(s, 1H), 7.44(t, 1H, J=8.5), 6.75(d, 2H, J=8.4), 4.11(s, 3H), 3.88(s, 3H), 3.77(s, 6H).

17. Preparation of 2-Carbomethoxy-6-methoxy-(N-(5,8-dimethoxy[1,2,4]triazolo[1,5-c]pyrimidin 2-yl)benzene-sulfonamide A suspension of 0.70 g (3.5 mmol) of 2-amino-5,8-dimethoxy[1,2,4]triazolo[1,5-c]pyrimidine in 15 mL of dry acetonitrile was prepared and 1.84 g (7.0 mmol of methyl 2-chlorosulfonyl-3-methoxybenzoate, 0.55 g (7.0 mmol) of dry pyridine, and 0.07 g (0.9 mmol) of dry dimethyl sulfoxide were added with stirring at ambient temperature, keeping the system dry. After 18 hours another 0.92 g of dry pyridine and 0.07 g of dry dimethyl sulfoxide were added, after another 36 hours another 0.92 g of dry pyridine was added, and after another 18 hours another 0.92 g of dry pyridine and another 0.07 g of dry dimethyl sulfoxide were added. After 18 more hours the mixture was diluted with 300 mL of dichloromethane. The organic phase was recovered and washed with 2×200 mL of water and 2×200 mL of 2N aqueous hydrochloric acid, dried over magnesium sulfate, filtered, and concentrated by evaporation under reduced pressure. The tan solid residue was triturated with diethyl ether to obtain the title compound as an 80 percent purity white solid. This solid was chromatographed twice on a silica gel column, eluting with a dichloromethane/ethanol/acetic acid mobile phase (which was largely unsuccessful) and was then recrystallized from hot methanol. The product obtained was 0.274 g (19 percent of theory) of shiny white needles melting at 215°–217° C.

Elemental Analysis $C_{16}H_{17}N_5O_7S$ Calc.: %C, 45.4; %H, 4.05; %N, 16.5; %S, 7.57 Found: %C, 44.7; %H, 3.96; %N, 16.2; %S, 7.93

NMR: $^1$H (DMSO-d6): 11.76(s, 1H), 7.60(t, 1H, J=8.3), 7.28(d, 1H, J=8.3), 7.05(d, 1H, J=7.6), 4.07(s, 3H), 3.88(s, 3H), 3.81(s, 3H), 3.78(s, 3H).

18. Preparation of 2,6-Dimethoxy-(N-(5,8-dimethoxy-[1,2,4]triazolo[1,5-c]pyrimidin 2-yl)benzenesulfonamide A suspension of 0.80 g (4.1 mmol) of 2-amino-5,8-dimethoxy[1,2,4]triazolo[1,5-c]pyrimidine in 15 mL of dry acetonitrile was prepared and 1.94 g (8.2 mmol of 2,6-dimethoxybenzenesulfonyl chloride, 0.65 g (8.2 mmol) of dry pyridine, and 0.08 g (1 mmol) of dry dimethyl sulfoxide were added at ambient temperature with stirring, keeping the system dry. After 24 hours the mixture was diluted with 200 mL of dichloromethane. The organic phase was recovered and washed with 2×200 mL of water and 2×200 mL of 2N aqueous hydrochloric acid, dried over magnesium sulfate, filtered, and concentrated by evaporation under reduced pressure. The orange solid residue was dissolved in 5 mL of dichloromethane and then diethyl ether was added dropwise with stirring. The gray solid that formed was recovered by filtration, washed with ether, and dried at 50° C. under reduced pressure to obtain 1.11 g (68 percent of theory) of title compound as an off-white solid melting at 239°–240.5° C.

Elemental Analysis $C_{15}H_{17}N_5O_6S$ Calc.: %C, 45.6; %H, 4.33; %N, 17.7% Found: %C, 45.7; %H, 4.19; %N, 17.6%

NMR: $^1$H (DMSO-d6): 11.54(s, 1H), 7.55(s, 1H), 7.44(t, 1H, J=8.4), 6.74(d, 2H, J=8.4), 4.06(s, 3H), 3.88(s, 3H), 3.76(s, 6H).

19. Preparation of 2-Methoxy-5-methyl-(N-(5,8-dimethoxy-[1,2,4]triazolo[1,5-c]pyrimidin 2-yl)benzenesulfonamide A mixture of 1.0 g (5.1 mmol) of 2-amino-5,8-dimethoxy [1,2,4]triazolo[1,5-c]pyrimidine, 2.1 g (10 mmol) of 2-methoxy-5-methylbenzenesulfonyl chloride, and 15 mL of dry acetonitrile was prepared and to this was added at ambient temperature with stirring and means to keep the system dry 0.8 mL (10 mmol) of dry pyridine and 71 microliters (1.0 mmol) of dry dimethyl sulfoxide. The mixture was allowed to stir for 18 hours and then another 1.0 g (5.0 mmol) of 2-methoxy-5-methylbenzenesulfonyl chloride was added. Stirring was continued another 24 hours at which time another 0.4 mL of dry pyridine and 35 microliters of dry dimethyl sulfoxide were added. After stirring another 9 days, the volatiles were removed by evaporation under reduced pressure. The dark residue was diluted with 50 mL of water and 50 mL of diethyl ether and the solids were recovered by filtration. The solids were slurried in dichloromethane and after 2 hours of stirring were recovered by filtration to obtain 1.2 g (63 percent of theory) of the title compound as a white powder melting at 217°–219° C.

Elemental Analysis $C_{15}H_{17}N_5O_5S$ Calc.: %C, 47.5; %H, 4.52; %N, 18.5; %S, 8.45 Found: %C, 47.7; %H, 4.61; %N, 18.3; %S, 8.80

NMR: $^1$H (DMSO-d6): 12.0(brs, 1H), 8.1(s, 1H), 7.7(t, 1H, J=8.2), 7.56–7.52(m, 2H), 4.06(s, 3H), 4.1(s, 3H), 3.9(s, 3H).

20. Preparation of N-(5,8-Dimethoxy[1,2,4]triazolo-[1,5-c] pyrimidin 2-yl)-2-methoxy-4-(trifluoromethyl)-3-pyridinesulfonamide A mixture of 0.75 g (93.8 mmol) of 2-amino-5,8-dimethoxy[1,2,4]triazolo[1,5-c]pyrimidine, 2.1 g (7.6 mmol) of 2-methoxy-4-(trifluoromethyl)pyridine-3-sulfonyl chloride, and 10 mL of dry acetonitrile was prepared and to this was added at ambient temperature with stirring and means to exclude moisture from the system 0.61 mL (7.6 mmol) of dry pyridine, 43 microliters (0.6 mmol) of dry dimethyl sulfoxide, and a small quantity of dry 4A molecular sieves. The mixture was stirred for 5 days. Another 1.0 g (3.4 mmol) of 2-methoxy-4-(trifluoromethyl) pyridine-3-sulfonyl chloride and 0.30 mL (3.5 mmol) of dry pyridine were added and the mixture stirred another 2 days. Another 0.30 mL (3.5 mmol) of dry pyridine was added and stirring continued for 4 more days. The mixture was then diluted with 100 mL of dichloromethane and the resulting mixture was washed with 2×100 mL of 2N aqueous hydrochloric acid, dried over magnesium sulfate, and concentrated by evaporation under reduced pressure. The tan solid residue was chromatographed on silica gel eluting with a mixture of dichloromethane and ethanol to obtain 0.90 g (54 percent of theory) of the title compound as a white solid melting at 214°–216° C.

Elemental Analysis $C_{14}H_{13}N_6F_3O_5S$ Calc.: %C, 38.7; %H, 3.02; %N, 19.4; %S, 7.38 Found: %C, 38.5; %H, 3.15; %N, 19.4; %S, 7.43

NMR: $^1$H (DMSO-d6): 12.3(brs, 1H), 8.64(d, 1H, J=5.3), 7.60–7.58(m, 2H), 4.06(s, 3H), 3.95(s, 3H), 3.86(s, 3H).

21. Preparation of 2-Methoxycarbonyl-6-methoxy-(N-(5-chloro-8-methoxy[1,2,4]triazolo[1,5-a]pyridin 2-yl)-benzenesulfonamide A mixture of 0.90 g (4.5 mmol) of 2-amino-5-chloro-8-methoxy[1,2,4]triazolo[1,5-a]pyridine and 35 mL of dry acetonitrile was prepared and 2.39 g (9.06 mmol) of methyl 2-chlorosulfonyl-3-methoxybenzoate, 0.72 g (9.1 mmol) of dry pyridine, and 0.071 g (0.91 mmol) of dimethyl sulfoxide were added with stirring at ambient temperature keeping the system dry. After 16 hours another 0.35 g (4.5 mmol) of dry pyridine was added and after an additional 48 hours the volatile components of the mixture were removed by evaporation under reduced pressure. The residue obtained was diluted with 50 mL of dichloromethane and 50 mL of 2N aqueous hydrochloric acid and the mixture was stirred vigorously for 72 hours. The solids present were recovered by filtration and washed with 3×25 mL of water, 3×10 mL of dichloromethane, and 3×10 mL of diethyl ether to obtain the title compound as a white solid. The total filtrate and washes were combined and were diluted with 25 mL of dichloromethane and 25 mL of 2N aqueous hydrochloric acid in a separatory funnel. The phases were separated and the organic phase was washed with 3×50 mL of 2N aqueous hydrochloric acid. It was then dried over sodium sulfate, filtered, and concentrated by evaporation under reduced pressure to obtain a yellow solid. This was suspended in 5.0 mL of dichloromethane and the solids were recovered by filtration and washed quickly with 2×5.0 mL of dichloromethane and 2×15 mL of diethyl ether to obtain additional title compound as a white solid. The combined title compound amounted to 1.09 g (56 percent of theory) and melted at 290°–292° C. with decomposition.

Elemental Analysis $C_{16}H_{15}N_4ClO_6S$ Calc.: %C, 45.0; %H, 3.45; %N, 13.1; %S, 7.51 Found: %C, 44.9; %H, 3.39; %N, 12.8; %S, 7.79

NMR: $^1$H (DMSO-d6): 11.60(s, 1H), 7.62(t, 1H, J=7.69), 7.24(m, 2H), 7.05(m, 2H), 3.92(s, 3H), 3.83(s, 3H), 3.77(s, 3H).

22. Preparation of 2-Methoxycarbonyl-6-methoxy-(N-(5,8-dimethoxy[1,2,4]triazolo[1,5-a]pyridin 2-yl)benzenesulfonamide A 0.871 g (2.04 mmol) sample of 2-methoxy-carbonyl-6-methoxy-(N-(5-chloro-8-methoxy[1,2,4]triazolo-[1,5-a]pyridin 2-yl)benzenesulfonamide was placed in a dry, closed flask with rubber and glass stoppers. This was dissolved in 20 mL of dry dimethyl sulfoxide added by means of a cannula and 1.39 mL of 6.12M sodium methoxide in methanol was added by means of a syringe with stirring at ambient temperature. After 16 hours another 0.050 mL of sodium methoxide solution was added and the reaction was allowed to proceed another 18 hours. Sufficient glacial acetic acid was added to make the mixture acidic and then the mixture was poured into 250 mL of dichloro-methane. The resulting mixture was washed with 6×200 mL of water, dried over sodium sulfate, filtered, and concentrated by evaporation under reduced pressure. The white solid residue obtained was dissolved in 600 mL of dichloromethane and purified by silica gel column chromatography, eluting with mixtures of dichloromethane and ethanol starting with a 99:1 v/v mixture and increasing the amount of ethanol with time. The fractions containing product were combined and concentrated by evaporation under reduced pressure to obtain 496 mg (57 percent of theory) of the title compound as an off-white solid melting at 274°–276° C. with decomposition.

Elemental Analysis $C_{17}H_{18}N_4O_7S$ Calc.: %C, 48.3; %H, 4.30; %N, 13.3; %S, 7.59 Found: %C, 48.6; %H, 4.26; %N, 13.1; %S, 7.83

NMR: $^1$H (DMSO-d6): 11.33(s, 1H), 7.61(t, 1H, J=8.06), 7.28(d, 1H, J=8.51), 7.02(d, 2H, J=7.94), 6.42(d, 1H, J=8.55), 3.98 (s, 3H), 3.85(s, 3H), 3.82 (s, 3H), 3.75 (s, 3H)

23. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hr photo-period which was maintained at about 23°–29° C. during the day and 22°–28° C. during the night. Nutrients and water were added on a regular basis and supplemental lighting was provided with overhead metal halide 1000 Watt lamps as necessary. The plants were employed for testing when they reached the first or second true leaf stage.

A weighed amount of each test compound, determined by the highest rate to be tested, was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The concentrated stock solutions obtained were diluted with an aqueous mixture containing acetone, water, isopropyl alcohol, dimethyl sulfoxide, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kiloPascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 2.

TABLE 2

POSTEMERGENCE HERBICIDAL ACTIVITY

| Cpd. No. | Rate ppm | BWCHK | BWCKB | BWLMQ | BWMGL | BWPIG | BWVEL | BWVIO | BWWBK | GWBLG | GWGFT | GWROX | GWWOT |
|---|---|---|---|---|---|---|---|---|---|---|---|---|---|
| 1 | 125 | — | 100 | 99 | 100 | 95 | 99 | — | 83 | 50 | 85 | — | 55 |
| 2 | 62.5 | — | 100 | 95 | 100 | 95 | 75 | — | 83 | 80 | 93 | — | 70 |
| 3 | 125 | — | 90 | 85 | 99 | 95 | 70 | — | 80 | 20 | 70 | — | 0 |
| 4 | 125 | 90 | 97 | 97 | 83 | 90 | 80 | — | 70 | 10 | 93 | — | 0 |
| 5 | 31.3 | — | 85 | 80 | 85 | 100 | 80 | 80 | 80 | 60 | 75 | — | 75 |
| 6 | 15.6 | — | 98 | 98 | 85 | 100 | 90 | — | 90 | 70 | 50 | — | 70 |
| 7 | 62.5 | — | 100 | 98 | 85 | 80 | 90 | — | — | 70 | 50 | — | 99 |
| 8 | 125 | — | 98 | 95 | 90 | 80 | 95 | — | 80 | 75 | 78 | — | 90 |
| 9 | 125 | — | 100 | 90 | 98 | 90 | 85 | — | — | 85 | 75 | — | 75 |
| 10 | 1.95 | 100 | 98 | 95 | 70 | 100 | 85 | 80 | — | 60 | 75 | 90 | 98 |
| 11 | 31.3 | 80 | 100 | 88 | 90 | 90 | 90 | 75 | 85 | 80 | 75 | 78 | 98 |
| 12 | 31.3 | 90 | 95 | 90 | 80 | 85 | 90 | 85 | 85 | 30 | 75 | 85 | 50 |
| 13 | 3.9 | 85 | 100 | 65 | 88 | 80 | 90 | 80 | 85 | 85 | 85 | 90 | 85 |
| 14 | 15.6 | 100 | 90 | 85 | 90 | 95 | 75 | 85 | 90 | 75 | 85 | 90 | 90 |
| 15 | 7.8 | 75 | 100 | 85 | 90 | 100 | 55 | 85 | 80 | 90 | 90 | 90 | 90 |
| 16 | 125 | 98 | 98 | 75 | 88 | 100 | 98 | 60 | 88 | 75 | 75 | 90 | 90 |
| 17 | 15.6 | 90 | 100 | 100 | 75 | 98 | — | 75 | 65 | 15 | 0 | 78 | 0 |
| 18 | 3.9 | 85 | 100 | 85 | 88 | 95 | 85 | 75 | 90 | 95 | 80 | 93 | 78 |
| 19 | 7.8 | 100 | 100 | 65 | 80 | 100 | 65 | 75 | 80 | 75 | 85 | 90 | 88 |
| 20 | 250 | — | 90 | 95 | 75 | 85 | 100 | — | 80 | 70 | 60 | 85 | 98 |
| 21 | 31.3 | — | 100 | 99 | 75 | 97 | 75 | — | 80 | 30 | 0 | — | 20 |
| 22 | 7.8 | 90 | 90 | — | 98 | 100 | 95 | 90 | 99 | 50 | 70 | 90 | 60 |
| 23 | 15.6 | — | 100 | 99 | 97 | 97 | 99 | — | 80 | 50 | 40 | 60 | 78 |
| 24 | 31.3 | 98 | 100 | 70 | 90 | 90 | 99 | 85 | 90 | 75 | 95 | 90 | 95 |
| 25 | 31.3 | 75 | 100 | 85 | 80 | 90 | 75 | 75 | 90 | 50 | 90 | 80 | 80 |
| 26 | 2.0 | 90 | 98 | 100 | 78 | 100 | 80 | 78 | 85 | 65 | 75 | 95 | 80 |
| 27 | 7.8 | 88 | 100 | 78 | 80 | 95 | 95 | 70 | 75 | 75 | 50 | 95 | 90 |
| 28 | 1.0 | 80 | 100 | 100 | 78 | 98 | 80 | 80 | 93 | 85 | 78 | 98 | 90 |
| 29 | 125 | 85 | 98 | — | 80 | 100 | 90 | 80 | 80 | 93 | — | 70 | 75 |
| 30 | 7.8 | 70 | 100 | 80 | 95 | 90 | 85 | 75 | 20 | 50 | 40 | 85 | 50 |
| 31 | 15.6 | 100 | 100 | 80 | 95 | 80 | 90 | 58 | 80 | 40 | 80 | 85 | 80 |
| 32 | 31.3 | 95 | 98 | — | 85 | 95 | 90 | 85 | 80 | 75 | 40 | 80 | 80 |
| 33 | 7.8 | 90 | 95 | 95 | 90 | 95 | 95 | 95 | 60 | 0 | 0 | 30 | 98 |
| 34 | 7.8 | 100 | 100 | 65 | 90 | 95 | 88 | 85 | 85 | 60 | 80 | 85 | 0 |
| 35 | 125 | 90 | 100 | 95 | 75 | 95 | 98 | 85 | 100 | 90 | 50 | 80 | 78 |
| 36 | 3.9 | 90 | 10.0 | 100 | 98 | 100 | 70 | 70 | 100 | 60 | 30 | 90 | 95 |
| 37 | 15.6 | 95 | 90 | 95 | 78 | 100 | 98 | 78 | 75 | 60 | 95 | 80 | 90 |
| 38 | 3.9 | 98 | 78 | 78 | 95 | 100 | 70 | 95 | 80 | 78 | 98 | 95 | 98 |
| 39 | 3.9 | 95 | 95 | 100 | 80 | 90 | 90 | 78 | 90 | 85 | 60 | 98 | 78 |
| 40 | 15.6 | 95 | 100 | 100 | 80 | 95 | 70 | 80 | 80 | 70 | 60 | 80 | 78 |
| 41 | 7.8 | 98 | 90 | 100 | 90 | 95 | 90 | 78 | 78 | 65 | 80 | 78 | 80 |
| 42 | 15.6 | 100 | 100 | 95 | 85 | 95 | 90 | 50 | 90 | 85 | 90 | 98 | 75 |
| 43 | 31.3 | 95 | 100 | 78 | 90 | 95 | 90 | 95 | 78 | 75 | 40 | 20 | 80 |
| 44 | 3.9 | 95 | 100 | 30 | 90 | 90 | 95 | 60 | 80 | 50 | 75 | 30 | 55 |
| 45 | 7.8 | 90 | 100 | 55 | 95 | 98 | 78 | 75 | 78 | 45 | 20 | 35 | 60 |
| 46 | 62.5 | 100 | 100 | 75 | 90 | 100 | 60 | 95 | 80 | 35 | 50 | 45 | 0 |
| 47 | 7.8 | 85 | 95 | 100 | 80 | 95 | 80 | 60 | 85 | 70 | 90 | 80 | 55 |

TABLE 2-continued

POSTEMERGENCE HERBICIDAL ACTIVITY

| Cpd. No. | Rate ppm | BWCHK | BWCKB | BWLMQ | BWMGL | BWPIG | BWVEL | BWVIO | BWWBK | GWBLG | GWGFT | GWROX | GWWOT |
|---|---|---|---|---|---|---|---|---|---|---|---|---|
| 48 | 62.5 | 95 | 100 | 78 | 90 | 95 | 98 | 95 | 50 | 90 | 20 | 90 | 30 |
| 49 | 15.6 | 95 | 95 | 100 | 80 | 90 | 90 | 90 | 90 | 65 | 30 | 70 | 90 |
| 50 | 2.0 | 100 | 90 | 70 | 90 | 100 | 70 | 90 | 85 | — | 40 | 95 | 85 |
| 51 | 62.5 | 95 | 90 | 70 | 78 | 95 | 50 | 85 | 90 | 90 | 100 | 95 | 100 |
| 52 | 7.8 | 100 | 100 | 65 | 75 | 95 | 95 | 78 | 95 | 78 | 45 | 0 | 70 |
| 53 | 31.3 | — | 95 | 60 | 85 | 100 | 90 | 90 | 78 | 90 | 95 | 95 | 95 |
| 54 | 15.6 | 100 | 90 | 80 | 85 | 100 | 90 | 90 | 90 | 100 | 80 | 95 | 95 |
| 55 | 0.5 | 85 | 100 | 100 | 78 | 98 | 55 | 70 | 80 | 45 | 60 | 75 | 80 |
| 56 | 62.5 | 90 | 100 | 80 | 75 | 95 | 75 | 85 | 90 | 80 | 78 | 95 | 90 |
| 57 | 125 | 95 | 100 | 65 | 85 | 85 | 90 | 45 | 80 | 85 | 50 | 80 | 55 |
| 58 | 62.5 | 100 | 85 | 78 | 80 | 100 | 80 | 90 | 80 | 95 | 78 | 95 | 95 |
| 59 | 7.8 | 95 | 100 | 78 | 85 | 100 | 90 | 95 | 95 | 70 | 25 | 95 | 90 |
| 60 | 2.0 | 95 | 100 | 65 | 60 | 90 | 90 | 60 | 78 | 70 | 80 | 80 | 70 |
| 61 | 250 | 80 | 95 | 90 | 78 | 70 | 85 | 85 | 85 | 78 | 20 | 30 | 20 |
| 62 | 31.3 | 80 | 90 | 95 | 90 | 100 | 95 | 80 | 85 | 90 | 90 | 90 | 90 |
| 63 | 31.3 | 95 | 90 | 95 | 90 | 100 | 78 | 78 | 85 | 70 | 90 | 95 | 90 |
| 64 | 31.3 | 65 | 85 | 95 | 80 | 90 | 65 | 90 | 90 | 78 | 85 | 70 | 80 |
| 65 | 15.6 | 95 | 95 | 100 | 90 | 100 | 95 | 90 | 90 | 90 | 90 | 95 | 100 |
| 66 | 62.5 | 95 | 95 | 85 | 78 | 90 | 90 | 85 | 80 | 90 | 80 | 90 | 90 |
| 67 | 31.3 | 100 | 60 | 95 | 90 | 85 | 90 | 90 | 80 | 85 | 70 | 90 | 85 |
| 68 | 62.5 | 90 | 70 | 100 | 90 | 100 | 85 | 85 | 78 | 80 | 90 | 90 | 85 |
| 69 | 31.3 | 65 | 70 | 60 | 55 | 85 | 70 | 40 | 90 | 65 | 60 | 65 | 60 |
| 70 | 7.8 | 80 | 55 | 78 | 90 | 95 | 95 | 95 | 70 | 95 | 70 | 90 | 80 |
| 71 | 7.8 | 80 | 100 | 95 | 90 | 90 | 90 | 80 | 70 | 80 | 60 | 90 | 60 |
| 72 | 15.6 | 75 | 95 | 95 | 50 | 90 | 78 | 75 | 90 | 90 | 80 | 90 | 78 |
| 73 | 15.6 | 90 | 95 | 80 | 70 | 70 | 80 | 75 | 78 | 70 | 65 | 95 | 75 |
| 74 | 2.0 | 95 | 80 | 100 | 85 | 100 | 80 | 70 | 90 | 78 | 75 | 85 | 78 |
| 75 | 2.0 | 90 | 80 | 95 | 90 | 90 | 80 | 70 | 78 | 70 | 50 | 70 | 75 |
| 76 | 31.3 | 75 | 100 | 95 | 78 | 100 | 95 | 85 | 90 | 85 | 50 | 100 | 90 |
| 77 | 15.6 | 78 | 90 | 70 | 78 | 95 | 90 | 90 | 85 | 95 | 95 | 95 | 95 |
| 78 | 15.6 | 95 | 90 | 80 | 90 | 100 | 85 | 95 | 95 | 78 | 30 | 80 | 90 |
| 79 | 250 | 90 | 78 | 100 | 78 | 95 | 75 | 80 | 95 | 80 | 100 | 85 | 70 |
| 80 | 1.0 | 65 | 80 | 80 | 85 | 100 | 80 | 78 | 90 | 70 | 90 | 60 | 90 |
| 81 | 3.9 | 95 | 95 | 95 | 95 | 100 | 90 | 75 | 90 | 78 | 80 | 80 | 95 |
| 82 | 31.3 | 90 | 90 | 75 | 90 | 85 | 90 | 90 | 80 | 80 | 0 | 78 | 78 |
| 83 | 15.6 | 95 | 85 | 80 | 90 | 90 | 90 | 20 | 80 | 0 | 20 | 10 | 0 |
| 84 | 7.8 | 90 | 98 | 80 | 80 | 50 | 35 | 78 | 80 | 70 | 45 | 60 | 78 |
| 85 | 7.8 | 80 | 95 | 95 | 85 | 100 | 85 | 70 | 90 | 78 | 30 | 30 | 80 |
| 86 | 31.3 | 95 | 95 | 60 | 75 | 80 | 90 | 70 | 90 | 65 | 0 | 78 | 78 |
| 87 | 31.3 | 90 | 80 | 95 | 80 | 85 | 70 | 85 | 90 | 80 | 70 | 75 | 90 |
| 88 | 125 | 95 | 85 | 80 | 78 | 90 | 80 | 80 | 78 | 75 | 40 | 60 | 40 |
| 89 | 125 | 85 | 70 | 60 | 90 | 95 | 80 | 80 | 95 | 85 | 80 | 80 | 70 |
| 90 | 62.5 | 90 | 90 | 80 | 65 | 90 | 80 | 90 | 90 | 75 | 20 | 80 | 75 |
| 91 | 125 | 90 | 78 | 70 | 78 | 90 | 80 | 78 | 80 | 80 | 65 | 90 | 0 |
| 92 | 3.9 | 90 | 85 | 90 | 90 | 95 | 75 | 70 | 80 | 70 | 70 | 90 | 78 |
| 93 | 31.3 | 95 | 85 | 95 | 90 | 95 | 65 | 70 | 85 | 60 | 80 | 85 | 80 |
| 94 | 15.6 | 85 | 85 | 95 | 90 | 95 | 85 | 78 | 90 | 78 | 90 | 90 | 75 |
| 95 | 31.3 | 90 | 100 | 30 | 95 | 95 | 95 | 80 | 90 | 78 | 40 | 30 | 45 |

TABLE 2-continued

POSTEMERGENCE HERBICIDAL ACTIVITY

| Cpd. No. | Rate ppm | BWCHK | BWCKB | BWLMQ | BWMGL | BWPIG | BWVEL | BWVIO | BWWBK | GWBLG | GWGFT | GWROX | GWWOT |
|---|---|---|---|---|---|---|---|---|---|---|---|---|
| 96 | 31.3 | 95 | 95 | 60 | 90 | 100 | 90 | 78 | 90 | 90 | 60 | 78 | 80 |
| 98 | 62.5 | 95 | 70 | 60 | 85 | 95 | 90 | 90 | 90 | 90 | 95 | 95 | 95 |
| 99 | 62.5 | 100 | 100 | 100 | 80 | 100 | 80 | 80 | 85 | 78 | 90 | 80 | 78 |
| 100 | 15.6 | 98 | 100 | 100 | 90 | 78 | 60 | 70 | 78 | 50 | 60 | 50 | 40 |
| 101 | 250 | 90 | 20 | 70 | 78 | 90 | 70 | 50 | 85 | 0 | 0 | 0 | 0 |
| 102 | 62.5 | 85 | 90 | 90 | 78 | 98 | 80 | 60 | 78 | 0 | 50 | 55 | 20 |
| 103 | 125 | 45 | 75 | 85 | 78 | 78 | 65 | 60 | 90 | 0 | 50 | 75 | 25 |
| 104 | 125 | 95 | 100 | 95 | 88 | 90 | 95 | 60 | 95 | 88 | 30 | 40 | 20 |
| 105 | 15.6 | 90 | 100 | 100 | 88 | 100 | 90 | 88 | 85 | 90 | 90 | 90 | 90 |
| 106 | 15.6 | 90 | 95 | 80 | 70 | 90 | 75 | 85 | 80 | 70 | 85 | 90 | 90 |
| 107 | 250 | 80 | 95 | 88 | 60 | 95 | 40 | 75 | 80 | 85 | 50 | 88 | 85 |
| 108 | 62.5 | 90 | 100 | 90 | 65 | 85 | 85 | 80 | 80 | 10 | 70 | 88 | 90 |
| 109 | 31.3 | 90 | 100 | 75 | 85 | 90 | 85 | 70 | 75 | 20 | 20 | 85 | 0 |
| 110 | 31.3 | 95 | 98 | 40 | 90 | 70 | 80 | 55 | 70 | 90 | 0 | 55 | 30 |
| 111 | 15.6 | 85 | 100 | — | 40 | 100 | 80 | 90 | 85 | 90 | 50 | 90 | 83 |
| 112 | 250 | 83 | 100 | — | 50 | 100 | 88 | 88 | 80 | 90 | 50 | 90 | 90 |
| 113 | 250 | 78 | 100 | 90 | 70 | 95 | 60 | 83 | 50 | 70 | 30 | 80 | 75 |
| 114 | 15.6 | 80 | 100 | — | 75 | 100 | 50 | 75 | 95 | 88 | 85 | 85 | 88 |
| 115 | 250 | 88 | 98 | — | 50 | 100 | 83 | 88 | 88 | 88 | 20 | 90 | 88 |
| 116 | 250 | 78 | 90 | 98 | 85 | 100 | 75 | 90 | 70 | 65 | 25 | 90 | 60 |
| 117 | 7.8 | 90 | 100 | — | 80 | 95 | 75 | 88 | 80 | 80 | 25 | 88 | 90 |
| 118 | 15.6 | 90 | 100 | 100 | 78 | 98 | 93 | 65 | 95 | 85 | 15 | 85 | 80 |
| 119 | 125 | 90 | 100 | — | 70 | 80 | 80 | 90 | 90 | 60 | 20 | 90 | 80 |
| 120 | 31.3 | 85 | 95 | 95 | 80 | 100 | 85 | 85 | 90 | 80 | 50 | 85 | 90 |
| 121 | 7.8 | 99 | 100 | 100 | 70 | 95 | 78 | 70 | 99 | 55 | 40 | 78 | 80 |
| 122 | 15.6 | 85 | 100 | — | 70 | 100 | 80 | 95 | 80 | 50 | 0 | 85 | 75 |
| 123 | 15.6 | 95 | 100 | 90 | 70 | 95 | 85 | 90 | 85 | 75 | 95 | 90 | 60 |
| 124 | 250 | 78 | — | 80 | 50 | 90 | 50 | 60 | 70 | 50 | 30 | 85 | 25 |
| 125 | 125 | 85 | 100 | 100 | 50 | 100 | 20 | 50 | 80 | 30 | 30 | 85 | 95 |
| 126 | 15.6 | 85 | 90 | 95 | 80 | 100 | 75 | 70 | 78 | 0 | 0 | 55 | 65 |
| 127 | 7.8 | 95 | 100 | 95 | 35 | 95 | 55 | 75 | 90 | 80 | 0 | 90 | 40 |
| 128 | 15.6 | 100 | 90 | 65 | 0 | 95 | 25 | 50 | 70 | 78 | 60 | 70 | 10 |
| 129 | 7.8 | 100 | 95 | 100 | 0 | 95 | 50 | 50 | 80 | 78 | 0 | 65 | 75 |
| 130 | 62.5 | 95 | 90 | 95 | 80 | 95 | 85 | 80 | 85 | 78 | 50 | 85 | 30 |
| 131 | 15.6 | 80 | 95 | 100 | 75 | 95 | 95 | 75 | 99 | 78 | 55 | 90 | 78 |
| 132 | 31.3 | 95 | 100 | 95 | 78 | 95 | 78 | 90 | 95 | 90 | 20 | 90 | 75 |
| 133 | 15.6 | 95 | 85 | 100 | 70 | 100 | 80 | 75 | 78 | 78 | 50 | 85 | 60 |
| 134 | 7.8 | 98 | 100 | 95 | 78 | 90 | 99 | 85 | 90 | 95 | 30 | 90 | 90 |
| 135 | 31.3 | 85 | 90 | 98 | 100 | 100 | — | 88 | 75 | 0 | 50 | 85 | 90 |
| 136 | 7.8 | 95 | 100 | — | 90 | 100 | 70 | 78 | 90 | 35 | 0 | 55 | 95 |
| 137 | 125 | 90 | 80 | 60 | 75 | 95 | 65 | 50 | 85 | 95 | 60 | 70 | 0 |
| 138 | 15.6 | 95 | 90 | 90 | 90 | 95 | 90 | 85 | 80 | 55 | 0 | 65 | 60 |
| 139 | 3.9 | 100 | 70 | 100 | 90 | 95 | 90 | 95 | 90 | 80 | 50 | 85 | 80 |
| 140 | 125 | 95 | 90 | 80 | 95 | 100 | 95 | 85 | 90 | 85 | 55 | 90 | 65 |
| 141 | 31.3 | 85 | 88 | 95 | 90 | 100 | 78 | 85 | 78 | 85 | 20 | 80 | 90 |
| 142 | 3.9 | 95 | 95 | 100 | 80 | 95 | 95 | 95 | 80 | 78 | 40 | 88 | 85 |
| 143 | 62.5 | 90 | 90 | 100 | 90 | 100 | 95 | 78 | 90 | 75 | 50 | 50 | 75 |
| 144 | 62.5 | 90 | 40 | 95 | 78 | 100 | 78 | 60 | 75 | 85 | 80 | 80 | 80 |
| | | | | | | | | | | 80 | 90 | 80 | 75 |

TABLE 2-continued

| | | POSTEMERGENCE HERBICIDAL ACTIVITY | | | | | | | | | | | |
|---|---|---|---|---|---|---|---|---|---|---|---|---|---|
| Cpd. No. | Rate ppm | BWCHK | BWCKB | BWLMQ | BWMGL | BWPIG | BWVEL | BWVIO | BWWBK | GWBLG | GWGFT | GWROX | GWWOT |
| 145 | 250 | 60 | 50 | 80 | 90 | 100 | 80 | — | 80 | 78 | 75 | 78 | 70 |
| 146 | 7.8 | 95 | 40 | 40 | 78 | 80 | 90 | 90 | 85 | 20 | 10 | 70 | 0 |
| 147 | 31.3 | 90 | 85 | 50 | 85 | 70 | 90 | 85 | 80 | 0 | 40 | 90 | 60 |
| 148 | 31.3 | 90 | 90 | 50 | 80 | 70 | 90 | 90 | 70 | 0 | 0 | 0 | 0 |
| 149 | 31.3 | 70 | 90 | 20 | 80 | 30 | 90 | 85 | 85 | 50 | 0 | 50 | 15 |
| 150 | 3.9 | 100 | 80 | 60 | 85 | 90 | 90 | 90 | 75 | 90 | 90 | 70 | 78 |
| 151 | 62.5 | 90 | 80 | 20 | 55 | 65 | 70 | 55 | 75 | 78 | 60 | 78 | 60 |
| 152 | 125 | 80 | 60 | 20 | 20 | 60 | 20 | 0 | 20 | 10 | 20 | 0 | 20 |
| 153 | 250 | — | 45 | — | 80 | 80 | 85 | 0 | 80 | 40 | 70 | 50 | 0 |
| 154 | 125 | 80 | 90 | 45 | 70 | 80 | 65 | 50 | 80 | 0 | 0 | 30 | 0 |
| 155 | 31.3 | 95 | 85 | 90 | 78 | 95 | 90 | 95 | 100 | 70 | 100 | 90 | 95 |
| 156 | 7.8 | 80 | 90 | 75 | 78 | 80 | 80 | 80 | 90 | 95 | 100 | 100 | 95 |
| 157 | 31.3 | 50 | 80 | 50 | 70 | 95 | 20 | 70 | 60 | 50 | 70 | 80 | 60 |
| 158 | 15.6 | 95 | 90 | 60 | 80 | 80 | 85 | 75 | 95 | 55 | 40 | 55 | 60 |
| 159 | 15.6 | 95 | 90 | 75 | 78 | 100 | 90 | 70 | 90 | 78 | 100 | 95 | 85 |
| 160 | 62.5 | 85 | 90 | 50 | 40 | 90 | 90 | 70 | 90 | 60 | 50 | 80 | 20 |
| 161 | 31.3 | 85 | 70 | 80 | 30 | 60 | 50 | 90 | 80 | 70 | 30 | 90 | 80 |
| 162 | 62.5 | 90 | 85 | 60 | 20 | 80 | 65 | 78 | 95 | 50 | 20 | 70 | 0 |
| 163 | 62.5 | 95 | 80 | 60 | 20 | 95 | 70 | 70 | 80 | 90 | 78 | 90 | 0 |
| 164 | 31.3 | 90 | 80 | 90 | 80 | 100 | 75 | 85 | 80 | 75 | 70 | 90 | 90 |
| 165 | 31.3 | 90 | 95 | 85 | 60 | 90 | 78 | 75 | 85 | 70 | 30 | 95 | 90 |
| 168 | 156 | 85 | 90 | 60 | 70 | 85 | 90 | 80 | 95 | 60 | 30 | 0 | 80 |
| 169 | 125 | 30 | 70 | 60 | 40 | 90 | 70 | 70 | 70 | 80 | 30 | 90 | 10 |
| 172 | 15.6 | 98 | 85 | 60 | 75 | 85 | 80 | 80 | 90 | 80 | 80 | 90 | 80 |
| 175 | 15.6 | — | 85 | 90 | 75 | 85 | 55 | 70 | 70 | 95 | 30 | 70 | 45 |
| 177 | 15.6 | 98 | 100 | 85 | 90 | 100 | 90 | 95 | 90 | 75 | — | 70 | 90 |
| 181 | 31.3 | 70 | 85 | — | 75 | 95 | 70 | 75 | 100 | 70 | 80 | 50 | 25 |
| 182 | 16.5 | 70 | 85 | 85 | 85 | 30 | 85 | 70 | 75 | 65 | 0 | 75 | 20 |
| 183 | 31.3 | 90 | 95 | 0 | 85 | 100 | 90 | 40 | 40 | 80 | 70 | 65 | 75 |
| 184 | 7.8 | 95 | 95 | 85 | 90 | 100 | 100 | 95 | 85 | 70 | — | 95 | 75 |
| 185 | 2.0 | 85 | 100 | 95 | 75 | 90 | 75 | 80 | 90 | 30 | 0 | 0 | 0 |
| 186 | 125 | 75 | 85 | 70 | 80 | 75 | 45 | 70 | 80 | 90 | 45 | 70 | 30 |
| 187 | 1.0 | 95 | 100 | 90 | 75 | 95 | — | 0 | 55 | 0 | 65 | 0 | 0 |
| 188 | 31.3 | 80 | 100 | 55 | 80 | 78 | 100 | 80 | 75 | 30 | 30 | 40 | 20 |
| 189 | 31.3 | — | 100 | 95 | 75 | 95 | 75 | 75 | 75 | 0 | 20 | 0 | 0 |
| 190 | 31.3 | 70 | 90 | 85 | 60 | 85 | 85 | 75 | 100 | 40 | 80 | 10 | 30 |
| 191 | 7.8 | 80 | 95 | 80 | 80 | 95 | 20 | 75 | 90 | 90 | 75 | 90 | 90 |
| 192 | 31.3 | — | 95 | 78 | 55 | 100 | 15 | 20 | 80 | 60 | 30 | 45 | 78 |
| 193 | 62.5 | — | 95 | 100 | 25 | 85 | 25 | 20 | 80 | 45 | 30 | 75 | 75 |
| 194 | 2.0 | 80 | 100 | 80 | 80 | 85 | 65 | 75 | 75 | 30 | 25 | 0 | 0 |
| 195 | 7.8 | 75 | 100 | 90 | 90 | 100 | 85 | 80 | 95 | 0 | 75 | 30 | 30 |
| 196 | 7.8 | 100 | 95 | 75 | 75 | 100 | 70 | 75 | 95 | 80 | 70 | 95 | 0 |
| 197 | 2.0 | 80 | 95 | 75 | 80 | 100 | 65 | 60 | 80 | 95 | 100 | 95 | 20 |
| 198 | 3.9 | 90 | 100 | 95 | 70 | 100 | 0 | 80 | 80 | 85 | 30 | 80 | 80 |
| 199 | 2.0 | 75 | 100 | 80 | 80 | 100 | 70 | 80 | 80 | 20 | 20 | 0 | 0 |
| 200 | 3.9 | 100 | 95 | 100 | 90 | 100 | 80 | 95 | 90 | 60 | 80 | 95 | 90 |
| 201 | 15.6 | — | 95 | 100 | 60 | 100 | 45 | 75 | 85 | 90 | 75 | 95 | 80 |
| 202 | 15.6 | 95 | 100 | 100 | 100 | 95 | 90 | 85 | 90 | 25 | 40 | 0 | 35 |

TABLE 2-continued

POSTEMERGENCE HERBICIDAL ACTIVITY

| Cpd. No. | Rate ppm | BWCHK | BWCKB | BWLMQ | BWMGL | BWPIG | BWVEL | BWVIO | BWWBK | GWBLG | GWGFT | GWROX | GWWOT |
|---|---|---|---|---|---|---|---|---|---|---|---|---|---|
| 203 | 3.9 | 95 | 95 | 75 | 55 | 95 | 60 | 25 | 100 | 25 | 0 | 0 | 0 |
| 204 | 7.8 | 100 | 100 | 95 | 80 | 75 | 100 | 80 | 65 | 90 | 55 | 45 | 45 |
| 205 | 15.6 | 95 | 95 | 95 | 95 | 100 | 95 | 80 | 100 | 40 | 20 | 15 | 0 |
| 206 | 62.5 | 95 | 100 | 40 | 85 | 100 | 100 | 85 | 85 | 50 | 0 | 60 | 15 |
| 208 | 15.6 | 100 | 100 | 100 | 85 | 100 | 90 | 100 | 100 | 70 | 70 | 25 | 15 |
| 209 | 31.3 | 100 | 90 | — | 70 | 95 | 80 | 85 | 90 | 40 | — | 0 | 0 |
| 210 | 62.5 | 95 | 95 | 100 | 90 | 100 | 95 | 100 | 90 | 70 | — | 55 | 55 |
| 211 | 7.8 | 95 | 90 | 90 | 80 | 90 | 70 | 90 | 90 | 0 | — | 0 | 0 |
| 212 | 3.9 | 100 | 85 | 100 | 40 | 90 | 70 | 90 | 85 | 100 | 70 | 100 | 90 |
| 215 | 31.3 | 80 | 95 | — | 95 | 100 | 80 | 75 | 85 | 70 | 80 | 100 | 95 |
| 216 | 250 | 60 | 40 | 40 | 70 | 70 | 70 | 75 | 80 | 90 | 85 | 90 | 85 |
| 218 | 31.3 | 95 | 95 | 95 | 80 | 95 | 85 | 45 | 85 | 60 | 98 | 85 | 80 |

BWCHK = chickweed (Stellaria media)
BWCKB = cocklebur (Xanthium strumarium)
BWLMQ = lambsquarters (Chenopodium album)
BWMGL = morningglory (Ipomoea hederacea)
BWPIG = pigweed (Amaranthus retroflexus)
BWVEL = velvetleaf (Abutilion theophrasti)
BWVIO = viola (Viola tricolor)
BWWBK = wild buckwheat (Polygonum convolvulus)
GWBLG = blackgrass (Alopecurus myosuroides)
GWGFT = giant foxtail (Setaria faberi)
GWROX = Rox Orange sorghum (Sorghum bicolor)
GWWOT = wild Oats (Avena fatua)

24. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 8 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture. A highest application rate of 4.48 Kg/Ha is achieved when 50 mg of test compound is employed.

The treated pots and control pots were placed in a greenhouse with an approximately 15 hr photoperiod which was maintained at about 23°–29° C. during the day and 22°–28° C. during the night. Nutrients and water were added on a regular basis and supplemental lighting was provided with overhead metal halide 1000 Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Table 3.

TABLE 3

| | | PREEMERGENCE HERBICIDAL ACTIVITY | | | | | | | | | | | |
|---|---|---|---|---|---|---|---|---|---|---|---|---|---|
| Cpd. No. | Rate, Kg/Ha | BWCKB | BWLMQ | BWMGL | BWPIG | BWVEL | BWWPT | GWBLG | GWBRN | GWCRB | GWGFT | GWROX | GWWOT |
| 1 | 0.28 | — | — | 70 | 100 | 50 | — | 60 | 40 | — | 95 | — | 70 |
| 2 | 0.28 | — | — | 60 | 95 | 40 | — | 70 | 100 | — | 95 | — | 60 |
| 3 | 0.28 | — | — | 30 | 100 | 0 | — | 0 | 70 | — | 50 | — | 30 |
| 4 | 0.28 | — | — | 40 | 95 | 40 | — | 0 | 60 | — | 90 | — | 0 |
| 5 | 0.14 | 95 | 98 | 90 | 98 | 90 | — | 75 | 90 | 85 | 95 | 95 | 80 |
| 6 | 0.14 | — | — | 80 | 98 | 95 | — | 90 | 70 | — | 90 | — | 60 |
| 7 | 0.14 | — | — | 60 | 98 | 85 | — | 80 | 90 | — | 60 | — | 50 |
| 8 | 0.14 | — | — | 90 | 90 | 60 | — | 40 | 70 | — | 30 | — | 50 |
| 9 | 0.14 | — | — | 90 | 95 | 85 | — | 70 | 90 | — | 80 | — | 50 |
| 10 | 0.018 | 90 | 90 | 90 | 95 | 90 | — | 100 | 100 | 100 | 95 | 100 | 85 |
| 11 | 0.070 | — | 95 | 90 | 95 | 90 | — | 70 | 90 | 95 | 80 | 98 | 50 |
| 12 | 0.035 | 80 | 100 | 70 | 100 | 80 | — | 90 | 98 | 90 | 98 | 95 | 70 |
| 13 | 0.018 | 85 | 98 | 85 | 98 | 80 | — | 95 | 98 | 100 | 98 | 100 | 90 |
| 14 | 0.018 | 90 | 98 | 85 | 95 | 80 | — | 98 | 98 | 95 | 95 | 98 | 98 |
| 15 | 0.035 | 88 | 98 | 80 | 99 | 80 | — | 98 | 95 | 95 | 75 | 90 | 95 |
| 16 | 0.28 | 90 | — | 80 | 90 | 85 | — | 75 | 80 | 50 | 95 | 100 | 50 |
| 17 | 0.28 | 80 | 99 | 75 | 100 | 90 | — | 80 | 98 | 98 | 90 | 98 | 85 |
| 18 | 0.035 | 85 | — | 90 | 95 | 85 | — | 95 | 99 | 95 | 85 | 95 | 75 |
| 19 | 0.009 | 70 | — | 70 | 98 | 85 | — | 95 | 78 | 90 | 85 | — | 80 |
| 21 | 0.28 | — | 90 | 95 | 95 | 90 | — | 90 | 95 | — | 95 | 100 | 90 |
| 22 | 0.14 | 90 | — | 90 | 98 | 98 | — | 95 | 98 | 98 | 90 | — | 80 |
| 23 | 0.035 | — | 90 | 90 | 95 | 85 | — | 95 | 98 | 85 | 95 | 99 | 80 |
| 24 | 0.035 | 75 | 98 | 90 | 99 | 85 | — | 85 | 90 | 80 | 85 | 100 | 80 |
| 25 | 0.14 | 80 | 98 | 85 | 90 | 70 | — | 85 | 80 | 95 | 90 | 100 | 90 |
| 26 | 0.018 | 75 | 95 | 80 | 98 | 85 | — | 90 | 95 | 95 | 95 | 100 | 80 |
| 27 | 0.070 | 85 | 100 | 80 | 95 | 90 | — | 90 | 98 | 90 | 95 | 100 | 90 |
| 28 | 0.009 | 60 | 100 | 80 | 80 | 80 | — | 90 | 90 | 90 | 78 | 80 | 80 |
| 29 | 0.28 | 78 | 90 | 75 | 85 | 85 | — | 78 | 78 | 55 | 55 | 90 | 85 |
| 30 | 0.070 | 30 | 95 | 90 | 98 | 90 | 80 | 90 | 80 | 95 | 85 | 95 | 55 |
| 31 | 0.14 | 65 | 95 | 75 | 100 | 85 | — | 100 | 95 | 100 | 95 | 100 | 80 |
| 32 | 0.28 | 70 | — | 95 | 95 | 80 | — | — | 70 | 60 | 80 | 95 | 95 |
| 33 | 0.14 | 70 | 100 | 85 | 95 | 78 | — | 100 | 90 | 95 | 95 | 95 | 90 |
| 34 | 0.018 | 75 | 78 | 90 | 80 | 85 | — | 90 | 70 | 98 | 85 | 90 | 80 |
| 35 | 0.28 | 95 | 98 | 80 | 90 | 90 | — | 80 | 85 | 70 | 78 | 95 | 80 |
| 36 | 0.14 | 50 | 100 | 80 | 98 | 80 | — | 90 | 90 | 100 | 90 | 100 | 80 |
| 37 | 0.035 | 65 | 90 | 80 | 85 | 85 | — | 90 | 98 | 78 | 98 | 100 | 90 |
| 38 | 0.14 | 75 | 85 | 80 | 95 | 90 | — | 95 | 65 | 70 | 70 | 90 | 80 |
| 39 | 0.009 | 78 | 95 | 75 | 80 | 78 | — | 95 | 65 | 55 | 65 | 70 | 85 |
| 40 | 0.14 | 85 | 98 | 90 | 95 | 95 | — | 95 | 100 | 80 | 90 | 100 | 55 |
| 41 | 0.070 | 75 | 100 | 90 | 90 | 90 | — | 85 | 100 | 100 | 95 | 100 | 80 |
| 42 | 0.035 | 80 | 90 | 90 | 95 | 85 | — | 90 | 95 | 65 | 80 | 70 | 95 |
| 43 | 0.14 | 90 | 100 | 80 | 100 | 95 | — | 65 | 78 | 55 | 90 | 78 | 90 |
| 44 | 0.14 | 90 | 100 | 80 | 95 | 95 | — | 80 | 80 | 65 | 75 | 85 | 80 |
| 45 | 0.28 | 95 | 100 | 80 | 100 | 90 | — | 80 | 95 | 70 | 95 | 70 | 98 |
| 46 | 0.14 | 70 | 85 | 90 | 75 | 78 | — | 78 | 98 | 70 | 80 | 98 | 78 |
| 47 | 0.035 | 70 | 80 | 90 | 90 | 78 | — | 85 | 90 | 95 | 90 | 98 | 70 |
| 48 | 0.28 | 80 | 80 | 75 | 75 | 85 | — | 75 | 75 | 65 | 78 | 98 | 80 |

TABLE 3-continued

PREEMERGENCE HERBICIDAL ACTIVITY

| Cpd. No. | Rate, Kg/Ha | BWCKB | BWLMQ | BWMGL | BWPIG | BWVEL | BWWPT | GWBLG | GWBRN | GWCRB | GWGFT | GWROX | GWWOT |
|---|---|---|---|---|---|---|---|---|---|---|---|---|---|
| 50 | 0.005 | 75 | 95 | 80 | 65 | 78 | 78 | 95 | 85 | 78 | 65 | 85 | 90 |
| 51 | 0.070 | 70 | 78 | 75 | 70 | 78 | — | 100 | 85 | 70 | 90 | 100 | 90 |
| 52 | 0.070 | 90 | — | 80 | 95 | 100 | 80 | 95 | 95 | 60 | 60 | 78 | 78 |
| 53 | 0.070 | 55 | 75 | 50 | 65 | 55 | — | 100 | 95 | 45 | 75 | 100 | 95 |
| 54 | 0.070 | 75 | 100 | 90 | 90 | 90 | — | 100 | 100 | 90 | 95 | 95 | 85 |
| 56 | 0.14 | 70 | 90 | 90 | 95 | 75 | 80 | 70 | 40 | 65 | 60 | 100 | 80 |
| 57 | 0.28 | 20 | 85 | 50 | 30 | 50 | 75 | 100 | 95 | 0 | 55 | 60 | 60 |
| 58 | 0.28 | 65 | 100 | 75 | 65 | 85 | 80 | 90 | 90 | 50 | 75 | 100 | 95 |
| 59 | 0.035 | 90 | 100 | 85 | 100 | 95 | 85 | 90 | 100 | 78 | 90 | 100 | 90 |
| 60 | 0.035 | 85 | 100 | 78 | 90 | 80 | 90 | 90 | 20 | 65 | 80 | 100 | 85 |
| 61 | 0.28 | 45 | 78 | 85 | 65 | 90 | 20 | 65 | 100 | 35 | 35 | 90 | 50 |
| 62 | 0.070 | 85 | 100 | 80 | 85 | 85 | 95 | 80 | 70 | 55 | 85 | 100 | 90 |
| 63 | 0.070 | 50 | 78 | 90 | 85 | 75 | 85 | 90 | 55 | 65 | 85 | 95 | 70 |
| 64 | 0.14 | 100 | 60 | 95 | 60 | 65 | 78 | 60 | 98 | 20 | 90 | 99 | 70 |
| 65 | 0.035 | 70 | 90 | 70 | 98 | 85 | 80 | 95 | 90 | 100 | 70 | 95 | 80 |
| 66 | 0.14 | 10 | 99 | 50 | 100 | 90 | 70 | 85 | 95 | 65 | 90 | 100 | 80 |
| 67 | 0.28 | 80 | 100 | 90 | 100 | 90 | 90 | 95 | 75 | 100 | 55 | 95 | 90 |
| 68 | 0.070 | 10 | 50 | 20 | 95 | 85 | 80 | 20 | 45 | 40 | 95 | 60 | 20 |
| 69 | 0.14 | 100 | 80 | 85 | 60 | 65 | 50 | 95 | 100 | 70 | 55 | 90 | 75 |
| 70 | 0.035 | 70 | 90 | 90 | 80 | 75 | 78 | 90 | 80 | 60 | 75 | 90 | 85 |
| 71 | 0.14 | 80 | 90 | 60 | 90 | 90 | 85 | 95 | 85 | 100 | 65 | 90 | 90 |
| 72 | 0.070 | 60 | 90 | 60 | 90 | 80 | 90 | 95 | 95 | 100 | 90 | 100 | 85 |
| 74 | 0.018 | 75 | 95 | 80 | 98 | 80 | 88 | 95 | 95 | 75 | 78 | 100 | 90 |
| 83 | 0.070 | 100 | 100 | 90 | 95 | 90 | — | 85 | 95 | 95 | 90 | 95 | 85 |
| 84 | 0.070 | 78 | 85 | 90 | 100 | 90 | — | 98 | 85 | 80 | 90 | 95 | 90 |
| 85 | 0.070 | 75 | 80 | 85 | 95 | 90 | 85 | 90 | 95 | 80 | 55 | 95 | 80 |
| 99 | 0.14 | 78 | 95 | 90 | 85 | 80 | — | 95 | 85 | 78 | 85 | 90 | 85 |
| 100 | 0.28 | 80 | 100 | 90 | 85 | 78 | — | 78 | 80 | 80 | 80 | 90 | 70 |
| 101 | 0.28 | 0 | 90 | 0 | 65 | 40 | — | 40 | 0 | 0 | 20 | 0 | 0 |
| 102 | 0.28 | 45 | 95 | 78 | 95 | 75 | — | 75 | 55 | 70 | 90 | 80 | 50 |
| 104 | 0.28 | 65 | — | 70 | — | 80 | 85 | 45 | 65 | 60 | — | 75 | 75 |
| 105 | 0.070 | 90 | 99 | 85 | 98 | 95 | — | 95 | 90 | 95 | 95 | 98 | 90 |
| 106 | 0.018 | 75 | 95 | 65 | 98 | 65 | — | 98 | 93 | 90 | 60 | 90 | 88 |
| 107 | 0.28 | 70 | 90 | 75 | 95 | 20 | — | 90 | 80 | 50 | 75 | 85 | 85 |
| 108 | 0.070 | 75 | 100 | 75 | 100 | 75 | — | 90 | 95 | 85 | 70 | 95 | 85 |
| 109 | 0.28 | 85 | 98 | 85 | 98 | 85 | — | 75 | 95 | 70 | 60 | 95 | 70 |
| 110 | 0.28 | 75 | 98 | 85 | 95 | 90 | — | 90 | 85 | 75 | 78 | 90 | 80 |
| 111 | 0.035 | 90 | 98 | 65 | 95 | 78 | — | 75 | 90 | 70 | 78 | 98 | 85 |
| 112 | 0.070 | 70 | 100 | 50 | 95 | 50 | — | 90 | 90 | 20 | 40 | 90 | 80 |
| 113 | 0.28 | 0 | 50 | 0 | 70 | 20 | — | 85 | 0 | 0 | 20 | 0 | 0 |
| 114 | 0.070 | 90 | 95 | 80 | 95 | 80 | — | 50 | 95 | 95 | 95 | 95 | 50 |
| 115 | 0.28 | 55 | 90 | 0 | 90 | 50 | — | 85 | 70 | 20 | 50 | 90 | 40 |
| 116 | 0.070 | 70 | — | 70 | 90 | 78 | — | 95 | 78 | 40 | 78 | 85 | 85 |
| 117 | 0.28 | 80 | 100 | 80 | 90 | 90 | — | — | 90 | 78 | 85 | 95 | 80 |
| 118 | 0.070 | 30 | — | 75 | 100 | 60 | — | — | 90 | 75 | 85 | 98 | 90 |
| 119 | 0.28 | 78 | — | 50 | 90 | 100 | — | 90 | 78 | 45 | 40 | 60 | 40 |
| 120 | 0.28 | 80 | 100 | 80 | 95 | 60 | — | — | 85 | 80 | 78 | 95 | 85 |
| 121 | 0.14 | 70 | 100 | 90 | 95 | 85 | — | 90 | 90 | 95 | 90 | 98 | 85 |

TABLE 3-continued

| | | PREEMERGENCE HERBICIDAL ACTIVITY | | | | | | | | | | | |
|---|---|---|---|---|---|---|---|---|---|---|---|---|---|
| Cpd. No. | Rate, Kg/Ha | BWCKB | BWLMQ | BWMGL | BWPIG | BWVEL | BWWPT | GWBLG | GWBRN | GWCRB | GWGFT | GWROX | GWWOT |
| 122 | 0.28 | 80 | 100 | 90 | 100 | 85 | — | 90 | 98 | 90 | 80 | 100 | 80 |
| 123 | 0.070 | 80 | — | 85 | 95 | 90 | — | — | 98 | 95 | 90 | 98 | 90 |
| 124 | 0.29 | 70 | 100 | 65 | 100 | 70 | — | 80 | 90 | 30 | 60 | 100 | 50 |
| 125 | 0.28 | 75 | 80 | 50 | 95 | 80 | — | 85 | 65 | 60 | 20 | 100 | 78 |
| 126 | 0.28 | 78 | 100 | 90 | 100 | 85 | — | 78 | 95 | 80 | 70 | 100 | 50 |
| 127 | 0.14 | 90 | 100 | 90 | 90 | 85 | 90 | 100 | 95 | 95 | 90 | 100 | 80 |
| 129 | 0.035 | 78 | 100 | 78 | 95 | 70 | 80 | 100 | 95 | 70 | 55 | 100 | 80 |
| 130 | 0.28 | 65 | — | 75 | 90 | 80 | 80 | 90 | 78 | 30 | 60 | 95 | 90 |
| 134 | 0.035 | 65 | 95 | 78 | 98 | 78 | — | 90 | 90 | 85 | 90 | 95 | 70 |
| 135 | 0.28 | 85 | 100 | 90 | 100 | 90 | — | 50 | 95 | 65 | 78 | 100 | 85 |
| 136 | 0.14 | 80 | — | 85 | 95 | 90 | — | 90 | 95 | 95 | 90 | 95 | 65 |
| 137 | 0.28 | 55 | 99 | 20 | 78 | 75 | — | 95 | 90 | 30 | 80 | 100 | 80 |
| 141 | 0.14 | 78 | 55 | 40 | 90 | 80 | 80 | 90 | 75 | 95 | 90 | 95 | 80 |
| 143 | 0.28 | 90 | 90 | 90 | 95 | 90 | — | 90 | 95 | 95 | 98 | 100 | 95 |
| 144 | 0.28 | 30 | — | 35 | 95 | 78 | — | 60 | 85 | 80 | 78 | 100 | 90 |
| 145 | 0.28 | 20 | 70 | 50 | 90 | 75 | 65 | 55 | 65 | 20 | 60 | 85 | 70 |
| 151 | 0.28 | 55 | 90 | 45 | 78 | 70 | 85 | 95 | 65 | 80 | 98 | 80 | 70 |
| 158 | 0.14 | 85 | 100 | 80 | 70 | 85 | 90 | 100 | 100 | 95 | 100 | 95 | 60 |
| 159 | 0.14 | 80 | 98 | 80 | 100 | 85 | 55 | 100 | 85 | 98 | 100 | 100 | 75 |
| 162 | 0.28 | 80 | 90 | 80 | 95 | 80 | 85 | 75 | 75 | 55 | 40 | 100 | 85 |
| 163 | 0.070 | 90 | 100 | 50 | 100 | 65 | 85 | 85 | 80 | 75 | 85 | 70 | 55 |
| 164 | 0.14 | 100 | 95 | 80 | 100 | 85 | 85 | 100 | 100 | 85 | 100 | 90 | 75 |
| 165 | 0.14 | 80 | 85 | 75 | 90 | 758 | 5 | 95 | 75 | 85 | 90 | 100 | 85 |
| 168 | 0.070 | 90 | 98 | 75 | 100 | 100 | 95 | 95 | 90 | 75 | 85 | 75 | 85 |
| 172 | 0.070 | 95 | 85 | 75 | 90 | 80 | 80 | 85 | 85 | 20 | 100 | 75 | 55 |
| 175 | 0.14 | 80 | 45 | 60 | 100 | 70 | 78 | 100 | 60 | 75 | 50 | 100 | — |
| 177 | 0.070 | 95 | 100 | 80 | 100 | 90 | 80 | 75 | 100 | 40 | 90 | 70 | 70 |
| 181 | 0.14 | 80 | 80 | 70 | 35 | 65 | 75 | 85 | 40 | 80 | 60 | 85 | 70 |
| 182 | 0.070 | 90 | 85 | 90 | 90 | 80 | 80 | 95 | 85 | 50 | 65 | 85 | — |
| 183 | 0.14 | 80 | 100 | 30 | 98 | 75 | 40 | 100 | 100 | 100 | 100 | 100 | — |
| 184 | 0.035 | 80 | 98 | 80 | 95 | 85 | 85 | 70 | 90 | 65 | 65 | 65 | 75 |
| 185 | 0.035 | 80 | 100 | 75 | 100 | 95 | 80 | 75 | 75 | 70 | 70 | 70 | 55 |
| 186 | 0.14 | 90 | 98 | 75 | 100 | 80 | 75 | 85 | 80 | 65 | 85 | 100 | 70 |
| 187 | 0.035 | 75 | 90 | 75 | 100 | 80 | 80 | 70 | 100 | 65 | 100 | 70 | 30 |
| 188 | 0.028 | 80 | 95 | 80 | 100 | 85 | 80 | 80 | 90 | 65 | 85 | 100 | 85 |
| 189 | 0.14 | 95 | 100 | 75 | 100 | 95 | 80 | 80 | 75 | 65 | 60 | 85 | 45 |
| 191 | 0.07 | 75 | 85 | 70 | 98 | 75 | 50 | 60 | 55 | 30 | 65 | 60 | 50 |
| 192 | 0.14 | 85 | 100 | 85 | 100 | 75 | 85 | 100 | 100 | 95 | 100 | 100 | 100 |
| 193 | 0.14 | 75 | 60 | 45 | 100 | 65 | 60 | 85 | 70 | 30 | 35 | 90 | 80 |
| 194 | 0.070 | 75 | 85 | 55 | 100 | 70 | 78 | 70 | 70 | 45 | 60 | 80 | 95 |
| 195 | 0.070 | 95 | 85 | 80 | 95 | 90 | 85 | 45 | 80 | 60 | 75 | 80 | 45 |
| 196 | 0.018 | 80 | 95 | 70 | 95 | 80 | 80 | 70 | 100 | 70 | 100 | 60 | 70 |
| 197 | 0.009 | 80 | 90 | 45 | 80 | 75 | 75 | 85 | 75 | 65 | 85 | 85 | 95 |
| 198 | 0.035 | 78 | 100 | 75 | 100 | 80 | 75 | 80 | 55 | 30 | 60 | 60 | 30 |
| 199 | 0.070 | 80 | 80 | 80 | 98 | 80 | 80 | 60 | 100 | 95 | 100 | 100 | 45 |
| 200 | 0.035 | 75 | 90 | 78 | 95 | 80 | 90 | 100 | 98 | 30 | 35 | 90 | 100 |
| 201 | 0.070 | 75 | 80 | 70 | 100 | 80 | 78 | 100 | 85 | 45 | 75 | 70 | 55 |
| 202 | 0.14 | 90 | 100 | 70 | 100 | 90 | 70 | 90 | 90 | 60 | 50 | 50 | 70 |

TABLE 3-continued

| | | PREEMERGENCE HERBICIDAL ACTIVITY | | | | | | | | | |
|---|---|---|---|---|---|---|---|---|---|---|---|
| Cpd. No. | Rate, Kg/Ha | BWCKB | BWLMQ | BWMGL | BWPIG | BWVEL | BWWPT | GWBLG | GWBRN | GWCRB | GWGFT | GWROX | GWWOT |
| 203 | 0.070 | 70 | 100 | 70 | 100 | 70 | 60 | 95 | 90 | 70 | 85 | 90 | 80 |
| 204 | 0.14 | 95 | 100 | 90 | 95 | 70 | 90 | — | 95 | — | 100 | 95 | 100 |
| 205 | 0.14 | 98 | 95 | 85 | 98 | 85 | 80 | 80 | 75 | 0 | 70 | 75 | 70 |
| 206 | 0.14 | 80 | 95 | 70 | 80 | 80 | 75 | 75 | 60 | 0 | 55 | 80 | 70 |
| 208 | 0.070 | 100 | 100 | 75 | 100 | 85 | 95 | 80 | 100 | 70 | 75 | 70 | 65 |
| 210 | 0.14 | 90 | 90 | 80 | 80 | 75 | 80 | 45 | 70 | 50 | 45 | 70 | 55 |
| 211 | 0.14 | 75 | 95 | 80 | 100 | 80 | 75 | 60 | 80 | 50 | 85 | 60 | 30 |
| 212 | 0.035 | 75 | 100 | 65 | 100 | 75 | 80 | — | 75 | 98 | 100 | 100 | 75 |
| 216 | 0.035 | 75 | 85 | 65 | 75 | 70 | 80 | 100 | 85 | 80 | 100 | 100 | 95 |
| 218 | 0.070 | 80 | 90 | 90 | 100 | 75 | 85 | 95 | 70 | 98 | 100 | 100 | — |

BWCKB = cocklebur (*Xanthium strumarium*)
BWLMQ = lambsquarters (*Chenopodium album*)
BWMGL = morningglory (*Ipomoea hederacea*)
BWPIG = pigweed (*Amaranthus retroflexus*)
BWVEL = velvetleaf (*Abutilon theophrasti*)
BWWPT = wild poinsettia (*Euphorbia heterophylla*)
GWBLG = blackgrass (*Alopecurus myosuroides*)
GWBRN = barnyardgrass (*Echinochloa crus-galli*)
GBCRB = crabgrass (*Digitaria sanguinalis*)
GWGFT = giant foxtail (*Setaria faberi*)
GWROX = Rox orange sorghum (*Sorghum bicolor*)
GWWOT = wild oats (*Avena fatua*)

What is claimed is:

1. An N-(triazoloazinyl)arylsulfonamide compound of the formula:

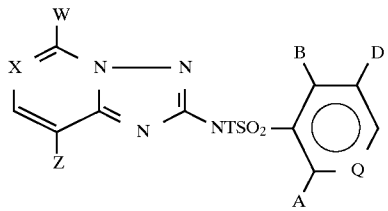

wherein
X represents N;
W represents $O(C_1-C_3$ alkyl), Cl, Br, F, or H;
Y represents H, $OCH_3$, F, Cl, Br, I, or $CH_3$ optionally substituted with up to three fluorine atoms;
Z represents $O(C_1-C_3$ alkyl), H, F, Cl, Br, I, $S(C_1-C_3$ alkyl), or $CH_3$ optionally substituted with up to three fluorine atoms; with the proviso that at least one of W and Z represents $O(C_1-C_3$ alkyl);
Q represents C—H or N;
A represents F, Cl, Br, or I, or $CO_2(C_1-C_4$ alkyl) or represents $C_1-C_3$ alkyl, $O(C_1-C_4$ alkyl), $O(C_3-C_4$ alkenyl), $O(C_3-C_4$ alkynyl), or $S(C_1-C_3$ alkyl) each optionally substituted with one $O(C_1-C_3$ alkyl), $S(C_1-C_3$ alkyl), chloro, bromo, or cyano substituent or with up to the maximum possible number of fluorine atoms, or represents a 2-methyl-1,3-dioxolan 2-yl moiety, and, when Q represents N, H;
B represents H, F, Cl, Br, I, $NO_2$, CN, $CO_2(C_1-C_4$ alkyl), $NH(C_1-C_3$ alkyl), or $N(C_1-C_3$ alkyl)$_2$ or represents $O(C_1-C_4$ alkyl), $O(C_3-C_4$ alkenyl), $O(C_3-C_4$ alkynyl), $C_1-C_3$ alkyl, $S(C_1-C_3$ alkyl), $SO(C_1-C_3$ alkyl), $SO_2$ $(C_1-C_3$ alkyl), $S(C_3-C_4$ alkenyl), $SO(C_3-C_4$ alkenyl), $SO_2(C_3-C_4$ alkenyl), $S(C_3-C_4$ alkynyl), $SO(C_3-C_4$ alkynyl), or $SO_2(C_3-C_4$ alkynyl) each optionally substituted with one $O(C_1-C_3$ alkyl), $S(C_1-C_3$ alkyl), chloro, bromo, or cyano substituent or with up to the maximum possible number of fluorine atoms; with the proviso that A and B do not simultaneously represent H;
D represents H, F, Cl, Br, I, $C_1-C_3$ alkyl, $OCH_3$, $OC_2H_5$, $CH_2F$, $CHF_2$, or $CF_3$; or B and D together represent a fragment of the formula O—$CH_2$—O, optionally substituted with one or two F or $CH_3$;
T represents H, $SO_2R$, C(O)R, C(O)OR, C(O)NR'$_2$, or $CH_2CH_2C(O)OR$;
R represents $C_1-C_4$ alkyl, $C_3-C_4$ alkenyl, or $C_3-C_4$ alkynyl each optionally possessing up to two chloro, bromo, $O(C_1-C_4)$alkyl, or phenyl substituents and up to the maximum possible number of fluoro substituents; and
R' represents H, $C_1-C_4$ alkyl, $C_3-C_4$ alkenyl, or $C_3-C_4$ alkynyl;
and, when T represents H, the agriculturally acceptable salts thereof.

2. A compound according to claim 1 wherein T represents hydrogen.

3. A compound according to claim 1 wherein Q represents C—H.

4. A compound according to claim 1 wherein Q represents N.

5. A compound according to claim 1 wherein one of W and Z represents methoxy and the other represents fluoro, chloro, bromo, methyl, methoxy, or ethoxy.

6. A compound according to claim 5 wherein W represents methoxy and Z represents methoxy, fluoro, chloro, or bromo.

7. A compound according to claim 1 wherein A represents methoxy, ethoxy, propoxy, 1-methylethoxy, methoxymethoxy, methoxyethoxy, 2-fluoroethoxy, 2-chloro-ethoxy, 2,2-difluoroethoxy, 1-(fluoromethyl) 2-fluoro-ethoxy, trifluoromethoxy, chloro, or fluoro; B represents hydrogen, methoxy, ethoxy, propoxy, 1-methylethoxy, methoxymethyl, methylthio, methyl, trifluoromethyl, trifluoromethoxy, fluoro, chloro, or methoxycarbonyl; and D represents hydrogen, fluoro, chloro, bromo, or methyl.

8. A compound according to claim 7 wherein B represents methoxy and D represents hydrogen; wherein A represents methoxy and D represents hydrogen, methyl, or chloro; or wherein B represents trifluoromethyl and D represents hydrogen.

9. A compound according to claim 1 wherein Q represents C—H and A represents methoxy, ethoxy, propoxy, or 1-methylethoxy, methoxymethoxy, methoxyethoxy, 2-fluoroethoxy, 2-chloroethoxy, 2,2-difluoroethoxy, or 1-(fluoromethyl) 2-fluoroethoxy; B represents hydrogen, methoxy, ethoxy, propoxy, 1-methylethoxy, methoxymethyl, trifluoromethyl, fluoro, chloro, or methoxycarbonyl; and D represents hydrogen, chloro, or methyl.

10. A compound according to claim 1 wherein Q represents N and A represents methoxy, ethoxy, propoxy, 1-methylethoxy, methoxymethoxy, methoxyethoxy, 2-fluoro-ethoxy, 2-chloroethoxy, 2,2-difluoroethoxy, or 1-(fluoro-methyl) 2-fluoroethoxy; B represents hydrogen, methoxy, ethoxy, propoxy, 1-methylethoxy, trifluoromethyl, or methoxycarbonyl; and D represents hydrogen or methyl.

11. A compound according to claim 1 which is selected from 2-methoxy-6-(trifluoromethyl)-N-(8-chloro-5-methoxy[1,2,4]triazolo[1,5-c]pyrimidin 2-yl)benzenesulfonamide, 2,6-dimethoxy-N-(5,8-dimethoxy[1,2,4]-triazolo[1,5-c]pyrimidin 2-yl)benzenesulfonamide, 2-methoxy-5-methyl-N-(5,8-dimethoxy[1,2,4]triazolo[1,5-c]pyrimidin-2-yl)benzenesulfonamide, 5-chloro 2-methoxy-N-(5,8-dimethoxy[1,2,4]triazolo[1,5-c]pyrimidin 2-yl) benzene-sulfonamide, 2-methoxy-4-(trifluoromethyl)-N-(5,8-di-methoxy[1,2,4]triazolo[1,5-c]pyrimidin 2-yl)pyridine-3-sulfonamide, 2-(2-fluoroethoxy)-6-(trifluoromethyl)-N-(5,8-dimethoxy[1,2,4]triazolo[1,5-c]pyrimidin 2-yl)-benzenesulfonamide, 2-(2-chloroethoxy)-6-(trifluoromethyl)-N-(5,8-dimethoxy[1,2,4]triazolo[1,5-c]pyrimidin-2-yl)benzenesulfonamide, 2-(2,2-difluoroethoxy)-6-(trifluoromethyl)-N-(5,8-dimethoxy[1,2,4]triazolo-[1,5-c]pyrimidin 2-yl)benzenesulfonamide, and 2-(1-fluoromethyl 2-fluoroethoxy)-6-(trifluoromethyl)-N-(5,8-dimethoxy[1,2,4]triazolo[1,5-c]pyrimidin 2-yl)-benzenesulfonamide.

12. A composition comprising an herbicidal amount of an N-(triazoloazinyl)arylsulfonamide compound of the formula:

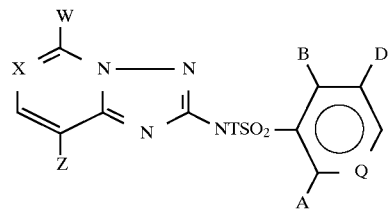

wherein
X represents N;

W represents O($C_1$–$C_3$ alkyl), Cl, Br, F, or H;
Y represents H, OCH$_3$, F, Cl, Br, I, or CH$_3$ optionally substituted with up to three fluorine atoms;
Z represents O($C_1$–$C_3$ alkyl), H, F, Cl, Br, I, S($C_1$–$C_3$ alkyl), or CH$_3$ optionally substituted with up to three fluorine atoms; with the proviso that at least one of W and Z represents O($C_1$–$C_3$ alkyl);
Q represents C—H or N;
A represents F, Cl, Br, or I, or CO$_2$($C_1$–$C_4$ alkyl) or represents $C_1$–$C_3$ alkyl, O($C_1$–$C_4$ alkyl), O($C_3$–$C_4$ alkenyl), O($C_3$–$C_4$ alkynyl), or S($C_1$–$C_3$ alkyl) each optionally substituted with one O($C_1$–$C_3$ alkyl), S($C_1$–$C_3$ alkyl), chloro, bromo, or cyano substituent or with up to the maximum possible number of fluorine atoms, or represents a 2-methyl-1,3-dioxolan 2-yl moiety, and, when Q represents N, H;
B represents H, F, Cl, Br, I, NO$_2$, CN, CO$_2$($C_1$–$C_4$ alkyl), NH($C_1$–$C_3$ alkyl), or N($C_1$–$C_3$ alkyl)$_2$ or represents O($C_1$–$C_4$ alkyl), O($C_3$–$C_4$ alkenyl), O($C_3$–$C_4$ alkynyl), $C_1$–$C_3$ alkyl, S($C_1$–$C_3$ alkyl), SO($C_1$–$C_3$ alkyl), SO$_2$($C_1$–$C_3$ alkyl), S($C_3$–$C_4$ alkenyl), SO($C_3$–$C_4$ alkenyl), SO$_2$($C_3$–$C_4$ alkenyl), S($C_3$–$C_4$ alkynyl), SO($C_3$–$C_4$ alkynyl), or SO$_2$($C_3$–$C_4$ alkynyl) each optionally substituted with one O($C_1$–$C_3$ alkyl), S($C_1$–$C_3$ alkyl), chloro, bromo, or cyano substituent or with up to the maximum possible number of fluorine atoms; with the proviso that A and B do not simultaneously represent H;
D represents H, F, Cl, Br, I, $C_1$–$C_3$ alkyl, OCH$_3$, OC$_2$H$_5$, CH$_2$F, CHF$_2$, or CF$_3$; or B and D together represent a fragment of the formula O—CH$_2$—O, optionally substituted with one or two F or CH$_3$;
T represents H, SO$_2$R, C(O)R, C(O)OR, C(O)NR'$_2$, or CH$_2$CH$_2$C (O) OR;
R represents $C_1$–$C_4$ alkyl, $C_3$–$C_4$ alkenyl, or $C_3$–$C_4$ alkynyl each optionally possessing up to two chloro, bromo, O($C_1$–$C_4$)alkyl, or phenyl substituents and up to the maximum possible number of fluoro substituents; and
R' represents H, $C_1$–$C_4$ alkyl, $C_3$–$C_4$ alkenyl, or $C_3$–$C_4$ alkynyl;
and, when T represents H, the agriculturally acceptable salts thereof in admixture with an agriculturally acceptable adjuvant or carrier.

13. A composition according to claim 12 wherein T represents hydrogen.

14. A composition according to claim 12 wherein Q represents C—H.

15. A composition according to claim 12 wherein Q represents N.

16. A composition according to claim 12 wherein one of W and Z represents methoxy and the other represents fluoro, chloro, bromo, methyl, methoxy, or ethoxy.

17. A composition according to claim 16 wherein W represents methoxy and Z represents methoxy, fluoro, chloro, or bromo.

18. A composition according to claim 12 wherein A represents methoxy, ethoxy, propoxy, 1-methylethoxy, methoxymethoxy, methoxyethoxy, 2-fluoroethoxy, 2-chloroethoxy, 2,2-difluoroethoxy, 1-(fluoromethyl) 2-fluoroethoxy, trifluoromethoxy, chloro, or fluoro; B represents hydrogen, methoxy, ethoxy, propoxy, 1-methylethoxy, methoxymethyl, methylthio, methyl, trifluoro-methyl, trifluoromethoxy, fluoro, chloro, or methoxy-carbonyl; and D represents hydrogen, fluoro, chloro, bromo, or methyl.

19. A composition according to claim 18 wherein B represents methoxy and D represents hydrogen; wherein A represents methoxy and D represents hydrogen, methyl, or chloro; or wherein B represents trifluoro-methyl and D represents hydrogen.

20. A composition according to claim 12 wherein Q represents C—H and A represents methoxy, ethoxy, propoxy, or 1-methylethoxy, methoxymethoxy, methoxyethoxy, 2-fluoroethoxy, 2-chloroethoxy, 2,2-difluoroethoxy, or 1-(fluoromethyl) 2-fluoroethoxy; B represents hydrogen, methoxy, ethoxy, propoxy, 1-methylethoxy, methoxymethyl, trifluoromethyl, fluoro, chloro, or methoxycarbonyl; and D represents hydrogen, chloro, or methyl.

21. A composition according to claim 12 wherein Q represents N and A represents methoxy, ethoxy, propoxy, 1-methylethoxy, methoxymethoxy, methoxyethoxy, 2-fluoro-ethoxy, 2-chloroethoxy, 2,2-difluoroethoxy, or 1-(fluoro-methyl) 2-fluoroethoxy; B represents hydrogen, methoxy, ethoxy, propoxy, 1-methylethoxy, trifluoromethyl, or methoxycarbonyl; and D represents hydrogen or methyl.

22. A composition according to claim 12 wherein the compound is selected from 2-methoxy-6-(tri-fluoromethyl) -N-(8-chloro-5-methoxy[1,2,4]triazolo-[1,5-c]pyrimidin 2-yl)benzenesulfonamide, 2,6-dimethoxy-N-(5,8-dimethoxy[1,2,4]triazolo[1,5-c]pyrimidin 2-yl)-benzenesulfonamide, 2-methoxy-5-methyl-N-(5,8-dimethoxy[1,2,4]-triazolo[1,5-c]pyrimidin 2-yl) benzenesulfonamide, 5-chloro 2-methoxy-N-(5,8-dimethoxy[1,2,4]triazolo-[1,5-c]pyrimidin 2-yl) benzenesulfonamide, and 2-methoxy-4-(trifluoromethyl)-N-(5,8-dimethoxy[1,2,4]triazolo-[1,5-c]pyrimidin 2-yl) pyridine-3-sulfonamide.

23. A method of controlling undesirable vegetation which comprises applying to the vegetation or to the locus thereof an herbicidally effective amount of an N-(triazoloazinyl) arylsulfonamide compound of the formula:

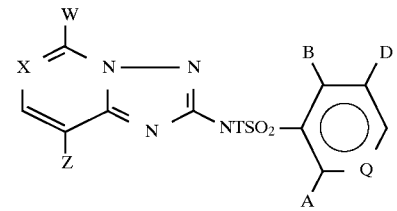

wherein
X represents N;
W represents O($C_1$–$C_3$ alkyl), Cl, Br, F, or H;
Y represents H, OCH$_3$, F, Cl, Br, I, or CH$_3$ optionally substituted with up to three fluorine atoms;
Z represents O($C_1$–$C_3$ alkyl), H, F, Cl, Br, I, S($C_1$–$C_3$ alkyl), or CH$_3$ optionally substituted with up to three fluorine atoms; with the proviso that at least one of W and Z represents O($C_1$–$C_3$ alkyl);
Q represents C—H or N;
A represents F, Cl, Br, or I, or CO$_2$($C_1$–$C_4$ alkyl) or represents $C_1$–$C_3$ alkyl, O($C_1$–$C_4$ alkyl), O($C_3$–$C_4$ alkenyl), O($C_3$–$C_4$ alkynyl), or S($C_1$–$C_3$ alkyl) each optionally substituted with one O($C_1$–$C_3$ alkyl), S($C_1$–$C_3$ alkyl), chloro, bromo, or cyano substituent or with up to the maximum possible number of fluorine atoms, or represents a 2-methyl-1,3-dioxolan 2-yl moiety, and, when Q represents N, H;
B represents H, F, Cl, Br, I, NO$_2$, CN, CO$_2$($C_1$–$C_4$ alkyl), NH($C_1$–$C_3$ alkyl), or N($C_1$–$C_3$ alkyl)$_2$ or represents O(C$_1$–C$_4$ alkyl), O(C$_3$–C$_4$ alkenyl), O(C$_3$–C$_4$ alkynyl), C$_1$–C$_3$ alkyl, S(C$_1$–C$_3$ alkyl), SO(C$_1$–C$_3$ alkyl), SO$_2$(C$_1$–C$_3$ alkyl), S(C$_3$–C$_4$ alkenyl), SO(C$_3$–C$_4$ alkenyl), SO$_2$(C$_3$–C$_4$ alkenyl), S(C$_3$–C$_4$ alkynyl), SO(C$_3$–C$_4$ alkynyl), or SO$_2$(C$_3$–C$_4$ alkynyl) each optionally substituted with one O(C$_1$–C$_3$ alkyl), S(C$_1$–C$_3$ alkyl), chloro, bromo, or cyano substituent or with up to the maximum possible number of fluorine atoms; with the proviso that A and B do not simultaneously represent H;

D represents H, F, Cl, Br, I, C$_1$–C$_3$ alkyl, OCH$_3$, OC$_2$H$_5$, CH$_2$F, CHF$_2$, or CF$_3$; or B and D together represent a fragment of the formula O—CH$_2$—O, optionally substituted with one or two F or CH$_3$;

T represents H, SO$_2$R, C(O)R, C(O)OR, C(O)NR'$_2$, or CH$_2$CH$_2$C(O)OR;

R represents C$_1$–C$_4$ alkyl, C$_3$–C$_4$ alkenyl, or C$_3$–C$_4$ alkynyl each optionally possessing up to two chloro, bromo, O(C$_1$–C$_4$)alkyl, or phenyl substituents and up to the maximum possible number of fluoro substituents; and R' represents H, C$_1$–C$_4$ alkyl, C$_3$–C$_4$ alkenyl, or C$_3$–C$_4$ alkynyl; and, when T represents H, the agriculturally acceptable salts thereof.

24. A method according to claim 23 wherein T represents hydrogen.

25. A method according to claim 23 wherein Q represents C—H.

26. A method according to claim 23 wherein Q represents N.

27. A method according to claim 23 wherein one of W and Z represents methoxy and the other represents fluoro, chloro, bromo, methyl, methoxy, or ethoxy.

28. A method according to claim 27 wherein W represents methoxy and Z represents methoxy, fluoro, chloro, or bromo.

29. A method according to claim 23 wherein wherein A represents methoxy, ethoxy, propoxy, 1-methylethoxy, methoxymethoxy, methoxyethoxy, 2-fluoroethoxy, 2-chloroethoxy, 2,2-difluoroethoxy, 1-(fluoromethyl) 2-fluoroethoxy, trifluoromethoxy, chloro, or fluoro; B represents hydrogen, methoxy, ethoxy, propoxy, 1-methylethoxy, methoxymethyl, methylthio, methyl, trifluoro-methyl, trifluoromethoxy, fluoro, chloro, or methoxy-carbonyl; and D represents hydrogen, fluoro, chloro, bromo, or methyl.

30. A method according to claim 29 wherein B represents methoxy and D represents hydrogen; wherein A represents methoxy and D represents hydrogen, methyl, or chloro; or wherein B represents trifluoromethyl and D represents hydrogen.

31. A method according to claim 23 wherein Q represents C—H and A represents methoxy, ethoxy, propoxy, or 1-methylethoxy, methoxymethoxy, methoxyethoxy, 2-fluoroethoxy, 2-chloroethoxy, 2,2-difluoroethoxy, or 1-(fluoromethyl) 2-fluoroethoxy; B represents hydrogen, methoxy, ethoxy, propoxy, 1-methylethoxy, methoxymethyl, trifluoromethyl, fluoro, chloro, or methoxycarbonyl; and D represents hydrogen, chloro, or methyl.

32. A method according to claim 23 wherein Q represents N and A represents methoxy, ethoxy, propoxy, 1-methylethoxy, methoxymethoxy, methoxyethoxy, 2-fluoro-ethoxy, 2-chloroethoxy, 2,2-difluoroethoxy, or 1-(fluoro-methyl) 2-fluoroethoxy; B represents hydrogen, methoxy, ethoxy, propoxy, 1-methylethoxy, trifluoromethyl, or methoxycarbonyl; and D represents hydrogen or methyl.

33. A method according to claim 23 wherein the compound is selected from 2-methoxy-6-(trifluoromethyl)-N-(8-chloro-5-methoxy[1,2,4]triazolo[1,5-c]pyrimidin 2-yl) benzenesulfonamide, 2,6-dimethoxy-N-(5,8-dimethoxy-[1,2,4]triazolo[1,5-c]pyrimidin 2-yl)benzenesulfonamide, 2-methoxy-5-methyl-N-(5,8-dimethoxy[1,2,4]triazolo[1,5-c]pyrimidin-2-yl)benzenesulfonamide, 5-chloro 2-methoxy-N-(5,8-dimethoxy[1,2,4]triazolo[1,5-c]pyrimidin 2-yl) benzene-sulfonamide, and 2-methoxy-4-(trifluoromethyl)-N-(5,8-dimethoxy[1,2,4]triazolo[1,5-c]pyrimidin 2-yl) pyridine-3-sulfonamide.

34. A method according to claim 23 wherein the compound is applied postemergence.

* * * * *